US010883083B2

(12) United States Patent
Vunjak-Novakovic et al.

(10) Patent No.: US 10,883,083 B2
(45) Date of Patent: Jan. 5, 2021

(54) TISSUE-ENGINEERED THREE-DIMENSIONAL MODEL FOR TUMOR ANALYSIS

(71) Applicant: The Trustees of Columbia University in the City of New York, New York, NY (US)

(72) Inventors: Gordana Vunjak-Novakovic, New York, NY (US); Aranzazu Villasante, New York, NY (US)

(73) Assignee: THE TRUSTEES OF COLUMBIA UNIVERSITY IN THE CITY OF NEW YORK, New York, NY (US)

(*) Notice: Subject to any disclaimer, the term of this patent is extended or adjusted under 35 U.S.C. 154(b) by 0 days.

(21) Appl. No.: 16/016,101

(22) Filed: Jun. 22, 2018

(65) Prior Publication Data

US 2018/0371415 A1 Dec. 27, 2018

Related U.S. Application Data

(63) Continuation of application No. PCT/US2016/068478, filed on Dec. 23, 2016, and a continuation-in-part of application No. 14/908,870, filed as application No. PCT/US2014/049416 on Aug. 1, 2014, now abandoned.

(60) Provisional application No. 62/387,121, filed on Dec. 23, 2015, provisional application No. 61/862,447, filed on Aug. 5, 2013, provisional application No. 61/861,957, filed on Aug. 2, 2013.

(51) Int. Cl.
| | |
|---|---|
| *C12N 5/077* | (2010.01) |
| *C12N 5/09* | (2010.01) |
| *C12N 5/071* | (2010.01) |
| *C12N 5/0775* | (2010.01) |
| *C12N 5/078* | (2010.01) |

(52) U.S. Cl.
CPC ......... *C12N 5/0654* (2013.01); *C12N 5/0643* (2013.01); *C12N 5/0655* (2013.01); *C12N 5/0663* (2013.01); *C12N 5/0693* (2013.01); *C12N 5/0697* (2013.01); *C12N 2502/1142* (2013.01); *C12N 2502/1311* (2013.01); *C12N 2502/1317* (2013.01); *C12N 2502/30* (2013.01); *C12N 2503/04* (2013.01); *C12N 2506/115* (2013.01); *C12N 2506/1353* (2013.01); *C12N 2513/00* (2013.01); *C12N 2533/54* (2013.01); *C12N 2533/80* (2013.01); *C12N 2533/90* (2013.01)

(58) Field of Classification Search
CPC .. C12N 5/0654; C12N 5/0655; C12N 5/0693; C12N 5/0697; C12N 5/0643; C12N 5/0663

See application file for complete search history.

(56) References Cited

U.S. PATENT DOCUMENTS

| | | |
|---|---|---|
| 6,734,000 B2 | 5/2004 | Chin et al. |
| 8,318,479 B2 | 11/2012 | Domansky et al. |
| 8,834,928 B1 | 9/2014 | Truncale et al. |
| 8,916,228 B2 | 12/2014 | Oh et al. |
| 9,925,301 B2 | 3/2018 | Kaplan et al. |
| 2004/0171143 A1 | 9/2004 | Chin et al. |
| 2007/0004035 A1 | 1/2007 | Sitzmann |
| 2010/0324677 A1 | 12/2010 | Zreiqat et al. |
| 2011/0313538 A1 | 12/2011 | Oh et al. |
| 2012/0035742 A1 | 2/2012 | Vunjak-Novakovic et al. |
| 2012/0272347 A1 | 10/2012 | Zhang et al. |
| 2013/0202644 A1 | 8/2013 | Holaday |
| 2014/0038275 A1 | 2/2014 | Gatenholm |
| 2015/0165092 A1 | 6/2015 | Kaplan |
| 2016/0053231 A1 | 2/2016 | Xu |
| 2016/0168542 A1 | 6/2016 | Villasante et al. |
| 2017/0074860 A1 | 3/2017 | Oh |

FOREIGN PATENT DOCUMENTS

| | | |
|---|---|---|
| WO | 2011098402 | 8/2011 |
| WO | 2015017784 | 2/2015 |

OTHER PUBLICATIONS

Villasante et al., "Bioengineered human tumor within a bone niche", Biomaterials, Jul. 2014, 35 (22): 5785-5794 (Year: 2014).*
Clohisy et al., "Osteoclasts are Required for Bone Tumors to Grow and Destroy Bone", J of Orthopaedic Research, 1998, 16 (6): 660-666 (Year: 1998).*
Taylor et al., "Ewing's Sarcoma cells express RANKL and support osteoclastogenesis", J Pathology, 2011, 225, p. 195-202 (Year: 2011).*

(Continued)

*Primary Examiner* — Ruth A Davis
(74) *Attorney, Agent, or Firm* — Lisa A. Chiarini; Reed Smith LLP

(57) ABSTRACT

A 3D decellularized bone scaffold seeded with cancer cells, such as prostate cancer cells or Ewing's sarcoma is provided. The three-dimensional includes Ewing's sarcoma (ES) tumor cells; and an engineered human bone scaffold. The engineered human bone scaffold further includes osteoblasts that secrete substance of the human bone, and osteoclasts that absorb bone tissue during growth and healing. The engineered human bone scaffold includes the tissue engineered three-dimensional model which recapitulates the osteolytic process. The engineered human bone scaffold is engineered by co-culturing of osteoblasts and osteoclasts. The osteoblast is produced by cell differentiation process from mesenchymal stem cells. The osteoclast is produced by cell differentiation from human monocytes, wherein the human monocytes are isolated from buffy coats. The scaffold can be used with cancer cell lines to identify therapeutic targets to slow, stop, and reverse tumor growth and progression as well as to predict the efficacy of potential therapeutics.

20 Claims, 38 Drawing Sheets

(56) References Cited

OTHER PUBLICATIONS

Miller et al., Biology of the Cell, 2013, 105, 289-303, "First identification of Ewing's sarcoma-derived extracellular vesicles and exploration of their biological properties and potential diagnostic implications" (Year: 2013).*

Liebschner et al., Topics in Tissue Engineering, 2003, II Bone, Chapter 6, Optimization of Bone Scaffold Engineering for Load Bearing Applications, Ed: N Ashammakhi and P. Ferretti (Year: 2003).*

Tsugita et al, PLOS One, www.plosone.org, Oct. 2013, vol. 8, Issue 10, e77416, p. 1-9 (Year: 2013).*

Fong et al. Modeling Ewing sarcoma tumors in vitro with 3D scaffolds. Proc Natl Acad Sci U S A. Apr. 2013, vol. 110 (16), p. 6500-6505. Epub 2013.

Moreau et al. Tissue-Engineered Bone Serves as a Target for Metastasis of Human Breast Cancer in a Mouse Model. Cancer Res. 2007, vol. 67(21), p. 10304-10308.

Jones et al. In Vitro Cytotoxic Drug Sensitivity Testing of Human Tumour Xenografts Grown as Multicellular Tumour Spheroids. Br J Cancer. 1982, vol. 46(6). p. 870-879.

Marcos-Campos et al. Bone scaffold architecture modulates the development of mineralized bone matrix by human embryonic stem cells. Biomaterials. 2012, vol. 33(33), p. 8329-8342. Epub Aug. 16, 2012.

Ho et al. Development of Multicellular Tumor Spheroid (MCTS) Culture from Breast Cancer Cell and a High Throughput Screening Method Using the MTTAssay. PLoS One. 2012, vol. 7(9):e44640. Epub Sep. 6, 2012.

Kenny et al. The morphologies of breast cancer cell lines in three-dimensional assays correlate with their profiles of gene expression, Mol Oncol. Jun. 2007 ; 1(1): 84-96.

Ong et al. Engineering a scaffold-free 3D tumor model for in vitro drug penetration studies, Biomaterials 31 (2010) 1180-1190.

Hartman O. et al. Biofunctionalization of Electrospun PCL Based Scaffolds with Perlecan Domain IV Peptide to Create a 3D Pharmacokinetic Cancer Model. Biomaterials 31 (21 )5700-5718, 2010.

Lamhamedi-Cherradi S. et al. 3D Tissue Engineered Model of Ewing's Sarcoma. Advanced Drug Delivery Reviews 79-80:155-171, 2014.

Pathi S. et al. A Novel 3D Mineralized Tumor Model to Study Breast Cancer Bone Metastasis. PLoS One 5(1 )e8849 Jan. 1-10, 2010.

International Search Report cited in PCT/US16/68478 dated Mar. 16, 2017.

International Search Report cited in PCT/US14/049416 dated Jan. 12, 2015.

Detsch et al., "3D-Cultivation of bone marrow stromal cells on hydroxyapatite scaffolds fabricated by dispense-plotting and negative mould technique", (Published online Nov. 7, 2007), J Mater Sci: Mater Med No. 19, pp. 1491-1496.

Oh et al., "Bone marrow absorption and retention properties of engineered scaffolds with micro-channels and nano-pores for tissue engineering: A proof of concept", (Available online Apr. 25, 2013), Ceramics International vol. 39, pp. 8401-8410.

Xiong et al., "A Novel in Vitro Three-Dimensional Macroporous Scaffolds from Bacterial Cellulose for Culture of Breast Cancer Cells, Journal of Biomaterials and Nanobiotechnology", Aug. 2, 2013, vol. 4, pp. 316-326.

Talukdar et al., Engineered 3D silk-based metastasis models: Interactions between human breast adenocarcinoma, mesenchymal stem cells and osteoblast-like cells, 2013, Advanced Functional Materials, 23, 5249-5260 (Year 2013).

Villasante et. al., Recapitulating the Size and Cargo of Tumor Exosomes in a Tissue-Engineered Model, Theranostics 2016, vol. 6, Issue 8.

Villasante et. al., Tissue-Engineered Model of Human Osteolytic Bone Tumor, Tissue Engineering: Part C, vol. 23, No. 2, 2017.

Villasante et. al., Re-expression of silenced Ewing's sarcoma genes in tumor cell lines by an engineered bone microenvironment, Trans. Orthop. Res. Soc. 2013, 27, 0023.

Yamada et al., Modeling Tissue Morphogenesis and Cancer in 3D, Cell 130, Aug. 24, 2007 © 2007 Elsevier Inc.

Lawlor et al., Twenty Years On—What Do We Really Know About Ewing Sarcoma and What Is the Path Forward?, Crit Rev Oncog., 2015.

van der Worp HB, Howells DW, Sena ES, Porritt MJ, Rewell S, et al. (2010) Can Animal Models of Disease Reliably Inform Human Studies? PLoS Med 7(3): e1000245. doi:10.1371/journal.pmed.1000245.

Supplementary European Search Report for EP Application No. 15767864, dated Dec. 12, 2017.

European search opinion for EP Application No. 15767864, dated Dec. 12, 2017.

* cited by examiner

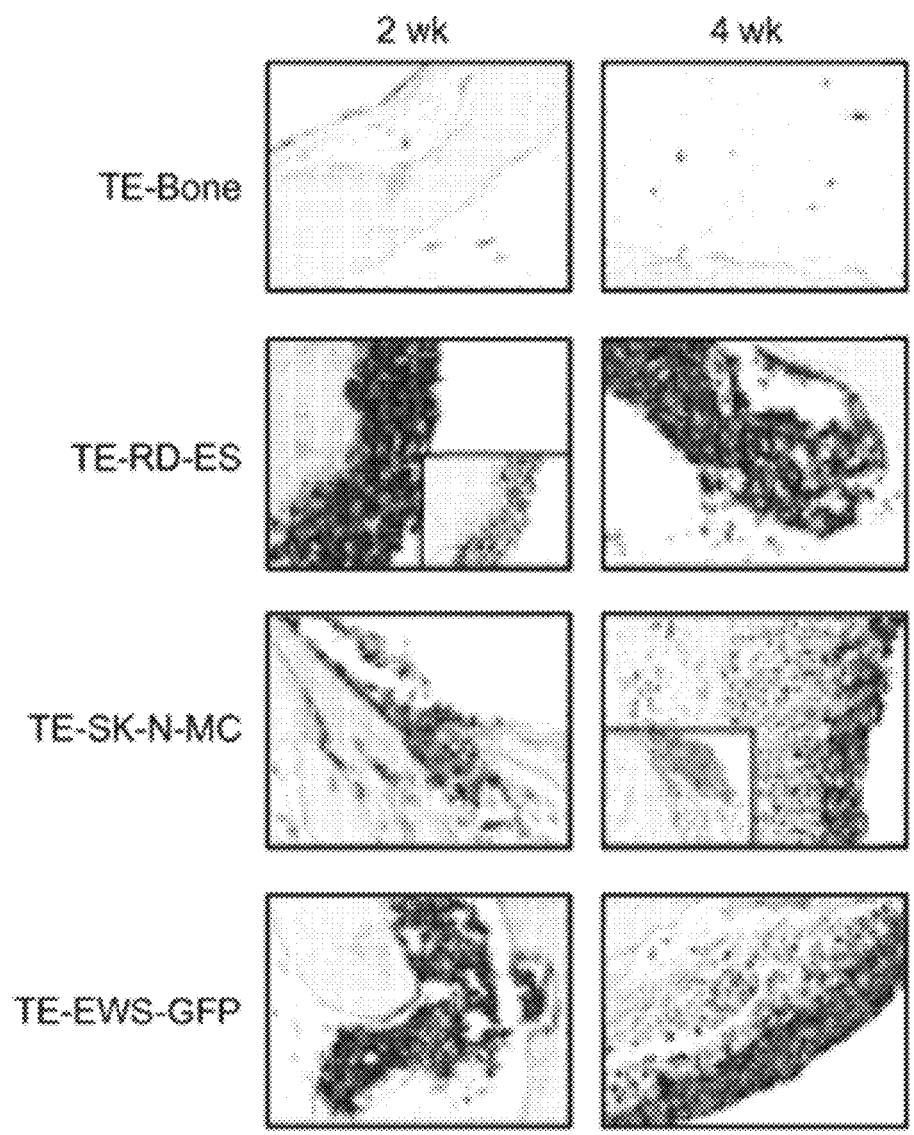

TISSUE-ENGINEERED THREE-DIMENSIONAL MODEL FOR TUMOR ANALYSIS

CROSS-REFERENCE TO RELATED APPLICATIONS

This application is a continuation of International Application No. PCT/US2016/068478, filed Dec. 23, 2016, which claims priority to U.S. Provisional Application No. 62/387,121 filed Dec. 23, 2015, and a continuation-in-part of U.S. application Ser. No. 14/908,870, which is a continuation of International Application No. PCT/US14/49416, filed Aug. 1, 2014, which claims the benefit of U.S. Provisional Application No. 61/861,957, filed Aug. 2, 2013 and claims the benefit of U.S. Provisional Application No. 61/862,447, filed Aug. 5, 2013, all of which are incorporated by reference in their entirety herein.

STATEMENT REGARDING FEDERALLY SPONSORED RESEARCH OR DEVELOPMENT

This invention was made with government support under grants EB002520 and EB17103 awarded by the NIH. The government has certain rights in the invention.

BACKGROUND

Technical Field

The disclosed subject matter relates to providing a three-dimensional decellularized bone scaffold seeded with cancer cells, such as prostate cancer cells and Ewing's sarcoma cells, and bone tissue cells. The embodiments herein generally relate to a three-dimensional tissue engineered model of tumors such as Ewing's sarcoma within a human bone niche. Models include recapitulating the osteolytic process observed in patients, and, more particularly, three-dimensional bone scaffold or bone tissue engineered by co-culturing osteoblasts and osteoclasts, that provides a controlled biomimetic environment for Ewing's sarcoma growth.

Description of the Related Art

Cancer research is experiencing tremendous advances in the development of genome-wide regulatory models and network-based methods that helped discover new cancer genes and new mechanisms of drug action. At the same time, there is a growing notion on how important environmental contributors are to the initiation, progression and suppression of cancer, including the three-dimensionality, other cells, tissue matrix, molecular and physical signaling. The lack of ability to replicate in vitro the complex in vivo milieu of human cancer is a critical barrier to evaluation of the potential therapeutic targets for clinical application.

Current experimental methods and models to study cancer growth and progression mainly utilize in vitro two-dimensional (2D) co-culturing of cancer specific cell lines and other cells found local in the tumor. However, these 2D models fail to capture the true three-dimensional (3D) progression of tumors and are limited in their ability to identify therapeutic targets. The shortcomings are underscored by the fact that most drugs fail to translate observed in vitro effects to in vivo studies and that only about 5% of drugs show effects in clinical trials.

Exosomes are small membrane vesicles of endocytic origin that are released into the extracellular environment and circulate in the blood stream. They contain cell-specific cargo molecules (i.e. proteins, mRNA, miRNA, DNA), membrane proteins, and lipids. Consequently, exosomes are finding application as diagnostic biomarkers in a number of cancers. Also, tumor-derived exosomes were shown to transfer a variety of bioactive molecules to other cells, inducing modifications of their environment and facilitating tumor growth and invasion.

Our knowledge about the putative roles of the microenvironment on tumor exosomes is limited, due to a lack of experimental models that efficiently mimic the human in vivo situation. Animal models used to study the effects of exosomes on cancer development often fail in representing the context of human disease. In vitro, cancer cells are typically cultured under conditions not recapitulating the 3D tumor environment. The absence of physiological cell-cell and cell-matrix-interactions and the currently used non-physiological substrates cause disparity from the in vivo situation and lead to changes in cell morphology, proliferation and cellular processes, such as endo and exocytosis. Despite the growing notion of the importance of cell microenvironment for cancer signaling, supernatants from monolayer cultures still represent the main source of tumor-derived exosomes such that their micro-environmental regulation remains largely unknown. Bioengineering methods are just about starting to bridge the gap between studies in cell monolayers and experimental animals, providing the models of human tumors that enable studies of how the microenvironment modulates cancer biology.

Historically, evaluation of therapeutic targets and anti-cancer drugs has been done mostly in simple cultures of cell monolayers and animal models. Although many drugs showed promise in these systems, most failed to translate into human patients and only ~5% showed anti-tumor activity in clinical trials. This discrepancy is caused by the lack of ability to sufficiently replicate the human microenvironment in these models. Cells in monolayers are known to rapidly lose their native features, while animal models do not recapitulate human tumors. Therefore, there is a real need for more effective cancer therapy, which requires better experimental models.

Ewing's sarcoma (ES) is a rare cancer that typically affects the bones. Most often it is found in the leg and arm bones of children, accounting for 1% of all childhood cancers. Ewing's sarcoma can be treated successfully in 50% to 75% of cases. Ewing's sarcoma is a poorly differentiated tumor of uncertain histogenesis and aggressive biologic behavior characterized by a strong membrane staining for CD99. It is the second most frequent bone tumor affecting children and young adults that generally arises and metastasizes in bone. It is characterized by fast growth and progressive bone destruction by osteolysis. Notably, ES cells are incapable of directly degrading bone matrix. Instead, they orchestrate the process of bone resorption through a vicious cycle of recruitment and activation of osteoclasts that is mediated by osteoblasts. Bone destruction by osteoclasts releases calcium and growth factors from the bone matrix that favor acidosis and tumor growth and thereby the osteoclasts activation and increased bone resorption.

Under physiological conditions, bone is remodeled in a fine-tuned process by which osteoblasts produce new extracellular matrix of the bone and osteoclasts resorb old bone. During this process, minerals (i.e. calcium and phosphorus), growth factors and cytokines are released from the bone matrix to maintain mineral homeostasis and acid-base balance in the body. However, the crosstalk between tumor cells, osteoblasts and osteoclasts disrupts the bone remodeling and initiates either bone destruction (osteolytic tumors) or abnormal bone formation (osteoblastic tumors).

The lack of ability to replicate in vitro the bone osteolysis associated with the ES represents a critical barrier to understanding of the mechanisms underlying tumor progression and evaluating the new therapeutics. Bioengineered tumor models are becoming invaluable tools for cancer research. However, modeling the bone invasion by cancer remains a challenge. Due to the intrinsic biology of osteolytic tumors, it is of paramount importance to include both osteoblasts and osteoclasts into the bone that will be populated by cancer cells, within the mineralized bone matrix.

Most prostate cancer deaths are due to metastasis into bone, and yet there is not a good model of metastatic prostate cancer: in vitro, the cancer cells rapidly lose their cancer phenotype, and in vivo the mouse bone is not permissive for cancer cell invasion.

In the last few decades, a number of 2-dimensional (2D) cultures and animal models of Ewing's sarcoma (ES) have contributed critical information about cancer biology and served as preclinical systems for therapeutic screens. Unfortunately, the existing ES models have failed to faithfully predict human physiology and support the development of effective treatment modalities. In spite of large investments, the use of these models has delayed drug discovery and exposed children to unnecessary chemicals, suggesting that modeling of the tumor progression requires interactions between tumor cells and their surrounding microenvironment.

Numerous two-dimensional (2D) culture studies and in vivo studies have been actively pursued to further understand the complex mechanisms and the molecular pathways in prostate cancer and Ewing's sarcoma. However, these models are not able to mimic the disease. Cells lose relevant properties in 2D due to the loss of physiological extracellular matrix (ECM) when cultured on artificial plastic surfaces at high serum concentrations. Studies in animal models also have their limitations. Prostate cancer and Ewing's sarcoma are human diseases and that are not accurately represented in an animal model. Based on studies in genetically engineered mice and using clinical data, it has been established that mouse bone acts as a barrier to prostate cancer cell invasion, in contrast to the human bone that is permissive to metastasis.

Recently, tissue-engineered models have started to bridge the gap between 2D in vitro cultures (used for discovery and screening) and in vivo animal models (used for efficacy and safety assessment before proceeding to clinical trials) providing a predictive, inexpensive and low time-consuming alternative. However, recapitulating tumor features in vitro is still a major challenge in the field. Therefore, there is a real need for better bioengineered experimental models that can biomimetic human microenvironment.

SUMMARY

In view of the foregoing, an embodiment herein provides a tissue engineered three-dimensional model. The three-dimensional model includes tumor cells such as Ewing's sarcoma (ES) or prostate cancer cells; and an engineered human bone scaffold. The engineered human bone scaffold may further include osteoblasts that secrete substance of the human bone, and osteoclasts that absorb bone tissue during growth and healing.

In one aspect, cancer cells are introduced into bone tissue engineered from human cells and cultured over long periods of time with vascular perfusion, oxygen control, and mechanical loading. Culturing tumor cells in a living bone environment may recapitulate the original in vivo tumor signature.

In accordance with one method, a tissue-engineered model of Ewing's sarcoma is established. A control of oxygen supply and incorporated perfusable vasculature into the engineered ES model is provided.

In accordance with another method, a validation is provided to validate the model by assessing effects of mechanical stress and perfusion on tumor phenotype and focal adhesion genes.

Further, a validation of the advanced bioengineering platform technology for cancer research, in two modifications: (1) for high-throughput screening (96-well format) and advanced studies of tumor biology (24-well format) is provided. The present technology has an unusually high transformative potential; it enables critical advances in several areas central to cancer research and uses pioneering approaches with potential for paradigm-shifting advances, and is based on pilot data.

In one embodiment, a cancer model is provided with a biomimetic microenvironment representing the pathophysiology of this malignancy. This is achieved by using three-dimensional (3D) instead of conventional two-dimensional (2D) cultures, with the aid of bone-engineering technology. In a 3D context, cancer cell lines modify their 2D transcriptional profile, recapitulating better the original tumor phenotype. This novel model is expected to be a powerful tool for predictive testing of anti-cancer and anti-metastatic compounds.

In some embodiments, a three-dimensional cancer model is provided. The model includes a decellularized bone scaffold and a plurality of cells arrayed on the scaffold. In some embodiments, the plurality of cells comprises cancer cells. In some embodiments, the cancer cells are metastatic cancer cells, prostate cancer cells, or Ewing's sarcoma cells. In some embodiments, the cancer cells comprise a plurality of spheroids. In some embodiments, the bone scaffold comprises a plurality of perfusion channels. In some embodiments, the plurality of cells comprises stem cells. In some embodiments, the plurality of cells comprises osteoblasts. In some embodiments, the plurality of cells comprises bone tissue cells. In some embodiments, the plurality of cells comprises patient-derived cells. In some embodiments, the scaffold is adapted for insertion in one well of a multiple well plate. In some embodiments, the scaffold is adapted for insertion in one well of a 96-well plate. In some embodiments, the scaffold is adapted for insertion in one well of a 24-well plate. In some embodiments, the scaffold has an outer region, and inner region, and a core region. In some embodiments, a first portion of the plurality of cells is arrayed in the outer region, a second portion of the plurality of cells is arrayed in the inner portion, and a third portion of the plurality of cells is arrayed in the core region. In such embodiments, the second portion is hypoxic and the third portion is necrotic.

In some embodiments, a platform for modelling cancer is provided. The platform includes a decellularized bone scaffold, an oxygen supply in gaseous communication with the bone scaffold, a vasculature in fluid communication with the bone scaffold, and a mechanical load coupled to the bone scaffold. In some embodiments, the mechanical load is adapted to apply a mechanical stress to the bone scaffold. In some embodiments, the vasculature comprises a nutrient supply.

In some embodiments, a bioreactor is provided. The bioreactor includes a decellularized bone scaffold, an oxygen supply in gaseous communication with the bone scaffold and a vasculature in fluid communication with the bone scaffold. In some embodiments, the bioreactor is adapted to provide a biomimetic microenvironment to the scaffold.

In one embodiment, the engineered human bone scaffold includes the tissue engineered three-dimensional model that recapitulates the osteolytic process. In another embodiment, the engineered human bone scaffold is engineered by co-culturing of osteoblasts and osteoclasts. In an alternate embodiment, the osteoblast is produced by cell differentiation process from mesenchymal stem cells. In another embodiment, the osteoclast is produced by cell differentiation from human monocytes. The human monocytes are isolated from buffy coats.

In one embodiment, the mesenchymal stem cells are human mesenchymal stem cells. In another embodiment, the three-dimensional model recapitulates using an osteolytic process. The osteoblasts and osteoclasts are cell differentiated for 12 days. The Ewing's sarcoma aggregates were infused in the engineered human bone scaffold. The infused Ewing's sarcoma aggregates are cultured for 7 days. In one embodiment, the Ewing's sarcoma aggregates are cultured in the engineered human bone scaffold to form a tumor model. In one embodiment, the three-dimensional model comprises a biomimetic environment for the Ewing's sarcoma tumor cells growth. The three-dimensional model mimics tumor microenvironment.

In another aspect, a tissue engineered three-dimensional model is provided. The tissue engineered three-dimensional model includes a) tumor cells, and b) engineered human bone scaffold. The three-dimensional model consists of tumor microenvironment. In one embodiment, the three-dimensional model comprises a Ewing's sarcoma tumor microenvironment. In another embodiment, the three-dimensional model mimics physical and chemical properties of the tumor microenvironment by collagen 1 (col1) and hyaluronic acid (HA) proteins. In another embodiment, the tumor microenvironment releases tumor exosome. The tumor exosome matches shape, size and cargo of tumor patients. The tumor exosome signals the growth of tumor cells in healthy bone cells.

In another embodiment, the three-dimensional model comprises a breast cancer tumor microenvironment. The model comprises human endothelia cells (EC) and bone marrow-derived mesenchymal stem cells (MSCs) cultured in a decellularized bone matrix disposed in a microfluidic chip configured to expose the cells to fluid flow through the bone matrix. In another embodiment, the model further comprises infused breast cancer cells, wherein the cells are exposed to physiologically relevant flow velocities, oxygen gradients and shear stresses.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part:

FIGS. 15A-C illustrates characterization of TE-ES models according to embodiments of the present disclosure.

DETAILED DESCRIPTION OF EXEMPLARY EMBODIMENTS

Figure 1:
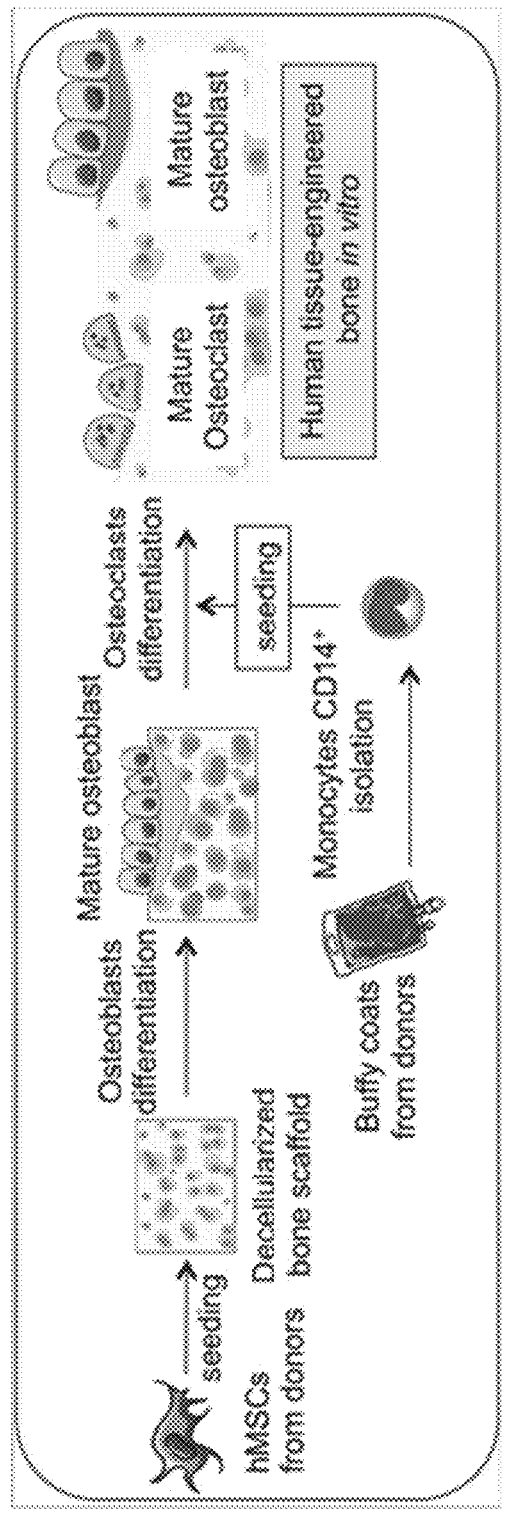
FIG. 1 illustrates human tissue engineered bone in vitro containing osteoblasts and osteoclasts according to embodiments of the present disclosure.

Reference will now be made in detail to exemplary embodiments of the disclosed subject matter, an example of which is illustrated in the accompanying drawings. Methods and corresponding steps of the disclosed subject matter will be described in conjunction with the detailed description of the system.

Improved human preclinical models are needed to better predict patients' responses to anticancer drugs. Increasing the complexity of models may be a successful strategy only if crucial components of a tumor are identified, replicated, and controlled in vitro.

Despite advances in modeling cancer metastasis, the maintenance of vascular networks in vitro still requires continuous use of specialized culture mediums. Under these conditions, cancer cells are forced to grow regardless of the niche signaling.

As mentioned, there remains a need for a new tool to better bioengineered experimental model to which can biomimetic human microenvironment. Embodiments herein achieve this by providing a three-dimensional bone scaffold or bone tissue engineered by co-culturing osteoblasts and osteoclasts that provides a controlled biomimetic environment for Ewing's Sarcoma growth. Using a 3D bone scaffold, with the preserved native biochemical and biophysical composition, supports the formation of stable microvasculature without high concentrations of angiogenic or growth factors commonly needed in vitro.

To address the challenges noted above, the present subject matter provides an advanced platform technology for controllable, quantitative, long-term studies of tissue-engineered tumors, such as prostate cancer and Ewing sarcoma (ES) as clinically significant models. In accordance with the subject matter, a 3D decellularized bone scaffold seeded with cancer cells, such as prostate cancer cells and Ewing's sarcoma cells (patient derived or cell lines) and bone tissue cells is provided. Some genes up-regulated in primary Ewing's sarcoma cells are silenced in existing Ewing's sarcoma cell lines. Thus, the technology of the present disclosure has demonstrated that cancer cells such as prostate cancer and Ewing's sarcoma cell lines cultured in this 3D scaffold re-express the silenced genes, better recapitulating the original in vivo tumor phenotype. Accordingly, the scaffold can be used with cancer cell lines, such as prostate cancer and Ewing's sarcoma, to identify therapeutic targets to slow, stop, and reverse tumor growth and progression as well as predict the efficacy of potential therapeutics. The technology can also be used with patient-derived cancer cells and mesenchymal stem cells for a personalized approach to cancer treatment.

Tumor Bone-Engineered Model

Cell culture and animal models have tremendously advanced our understanding of cancer biology. However both systems have limitations. Herein is described a bioengineered model of human Ewing's sarcoma that mimics the in vivo bone tumor niche with high biological fidelity. In this model, cancer cells that have lost their transcriptional profiles after monolayer culture re-express genes related to focal adhesion and cancer pathways. The bioengineered model recovers the original hypoxic and glycolytic tumor phenotype, and leads to re-expression of angiogenic and vasculogenic mimicry features that favor tumor adaptation. Differentially expressed genes between the monolayer cell culture and tumor environment are potential therapeutic targets that can be explored using the bioengineered tumor model.

Both the two-dimensional (2D) culture and in vivo models of cancer may be used to unravel the complex mechanisms and molecular pathways of cancer pathogenesis. Cancer cells lose many of their relevant properties in 2D culture, due to the lack of the native-like physiological milieu with 3D extracellular matrix (ECM), the other cells and regulatory factors. As a result, 2D cultures are not predictive of antitumoral drug effects in the human being. Animal models have their own limitations in representing human disease, necessitating the use of clinical data. While simple 3D models of cancer, such as tumor spheroids, cell inserts, and cell encapsulation in hydrogels or porous scaffolds are an advance over monolayer cultures, cancer cells still remain deprived of native tumor environments where cancer cell-nonmalignant cell interactions are crucial for tumor biology. Indeed, the microenvironment can both inhibit and facilitate tumor growth and metastatic dissemination to distant organs. Current approaches are far from replicating the native in vivo milieu in which tumors develop, a necessary condition for advancing cancer research and translating novel therapies into clinical practice.

The present disclosure describes a model of human bone cancer (such as prostate cancer and Ewing's sarcoma) engineered by introducing tumor cell spheroids into their resident bone tissue environment that has been formed by culturing human mesenchymal stem cells in decellularized bone matrix. This model allows not only the cross-talk between the cancer cells, but also the interactions of cancer cells with the human bone cells and the mineralized bone matrix. Within such native-like environment, cancer cells (i) re-express focal adhesion and cancer related genes that are highly expressed in tumors but lost in monolayer cultures, (ii) recapitulate the original hypoxic and glycolytic tumor phenotypes, and (iii) acquire angiogenic capacity and vasculogenic mimicry that favor tumor initiation and adaptation. Bioengineered models of human bone cancer can be valuable tools for identifying genes that are differentially expressed between cell lines and tumors, and thus representing potential therapeutic targets.

Tissue-Engineered Model of Ewing's Sarcoma (TE-ES)

Figure 14A:
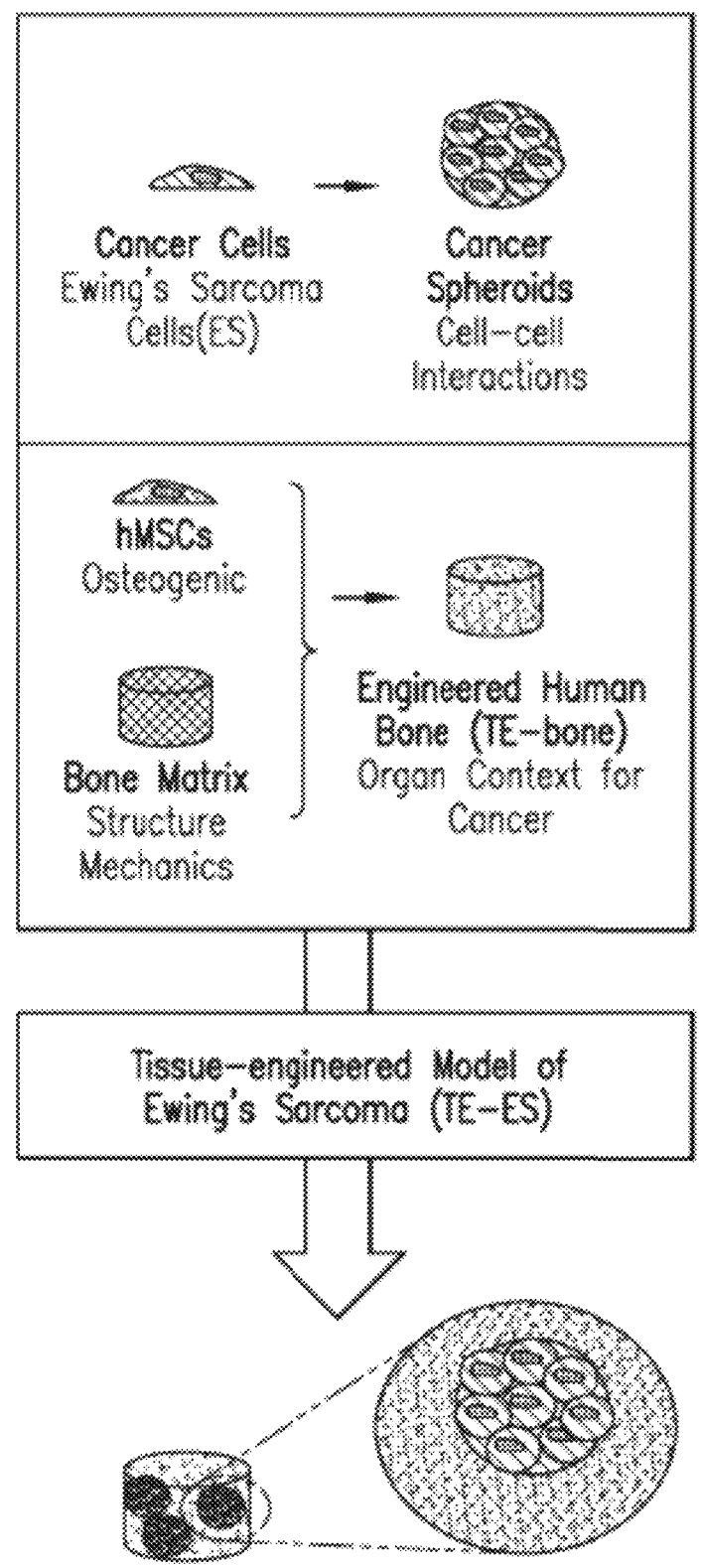
FIGS. 14A-C illustrate tissue-engineered models of Ewing's sarcoma (TE-ES) according to embodiments of the present disclosure.
Figure 14B:
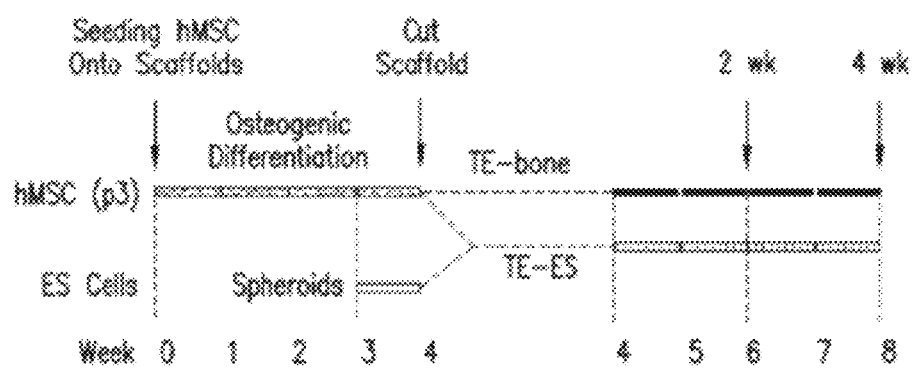
Figure 14C:
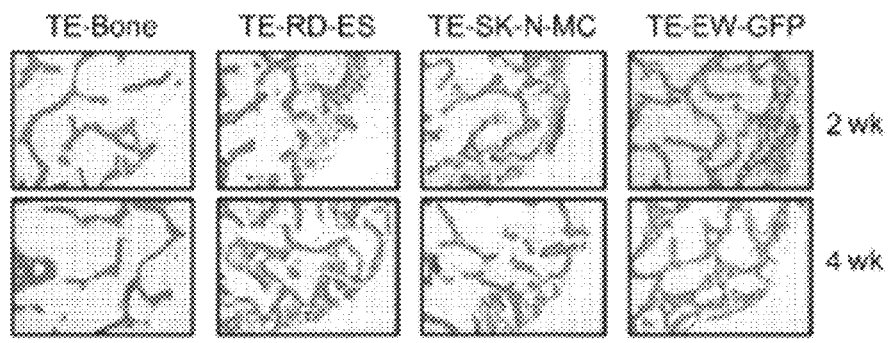

Tissue engineered models of Ewing's sarcoma according to embodiments of the present disclosure (TE-ES) are illustrated. FIG. 14A depicts a methodology used to develop bioengineered models of Ewing's sarcoma tumor. FIG. 14B depicts TE-ES generation. Fully decellularized bone scaffolds (4 mm diameter×4 mm high plugs) were seeded with hMSCs. After 4 weeks of culture in osteogenic differentiation medium, bone constructs were bisected. One half was seeded with Ewing's sarcoma spheroids (3 per construct);

the other half was used as control (TE-bone). Both TE-ES and TE-bone were cultured for 2 or 4 weeks in ES medium. FIG. 14C shows Hematoxylin and Eosin images of TE-bone controls and TE-ES models (TE-RD-ES, TE-SK-N-MC, TE-EW-GFP) at week 2 and 4 after introducing tumor spheroids.

To form the tumor model according to some embodiments, Ewing's sarcoma (ES) spheroids (providing a 3D context for local interactions of cancer cells) were introduced into a human bone niche generated by tissue-engineering technology (TE-bone) (FIG. 14A). TE-bone plugs were cultured for 4 weeks in osteogenic differentiation medium. In parallel, tumor spheroids were cultured in ES medium for one week. TE-bone plugs were bisected through the center, and 3 ES spheroids are introduced into one half of the construct, generating the Tissue-engineered Ewing's Sarcoma (TE-ES) model; the other half of each TE-bone plug can serve as control. TE-ES models and their control counterparts are cultured for an additional 2 or 4 weeks in ES medium (FIG. 14B). Three different TE-ES models are generated, using various ES cell lines (TE-RD-ES, TE-SK-N-MC, TE-EW-GFP) (FIG. 14C).

Bone Niche hMSCs differentiate into osteoblastic lineage and form viable, functional human bone when cultured on 3D scaffolds made of decellularized bone in osteogenic-differentiation medium. According to an embodiment of the present disclosure, the following approach is used to engineer a bone niche (TE-bone) for the tumor model. First, the osteogenic potential of hMSC is tested after three weeks of monolayer culture in osteogenic medium. Positive Alkaline phosphatase and Von Kossa stainings (FIG. 19A-B) and expression of bone markers by qRT-PCR (FIG. 19C) demonstrates bone differentiation capacity of hMSCs. In parallel, $1.5 \times 10^6$ hMSC (passage 3) are cultured in 4 mm×4 mm cylindrical decellularized bone scaffolds for 6 and 8 weeks, in osteogenic differentiation medium, and observed elevated expression levels of bone-related markers (OPN, BSP and OCN) as compared to the differentiation of same cells in monolayer cultures (FIG. 19D). Bone-related protein expression by IHC suggest that TE-bone is properly generated (FIG. 19E). Hypoxia is a pivotal microenvironmental factor for tumor development. Thus, hypoxia is confirmed in the middle of the TE-bone by tissue immunofluorescence of pimonidazole-binding cells (FIG. 19F).

The Ewing's sarcoma family of tumors (ESFT) is characterized by aggressive, undifferentiated, round cells, with strong expression of CD99, affecting mostly children and young adults. ESFT comprises Ewing's sarcoma (ES) that arises in bone, extraosseous ES (EES), peripheral primitive neuroectodermal tumors (pPNET) and Askin's tumors with a neuroectodermal origin. The chromosomal translocation t(11:22)(q24:q212) is the most common mutation (about 85-90% of cases) in ESFT and leads the formation of the EWS/FLI fusion protein which contributes to tumorigenesis in the cells of origin. Analyses of molecular signatures suggest that ESFT originate from mesenchymal and neural crest.

Figure 15B:
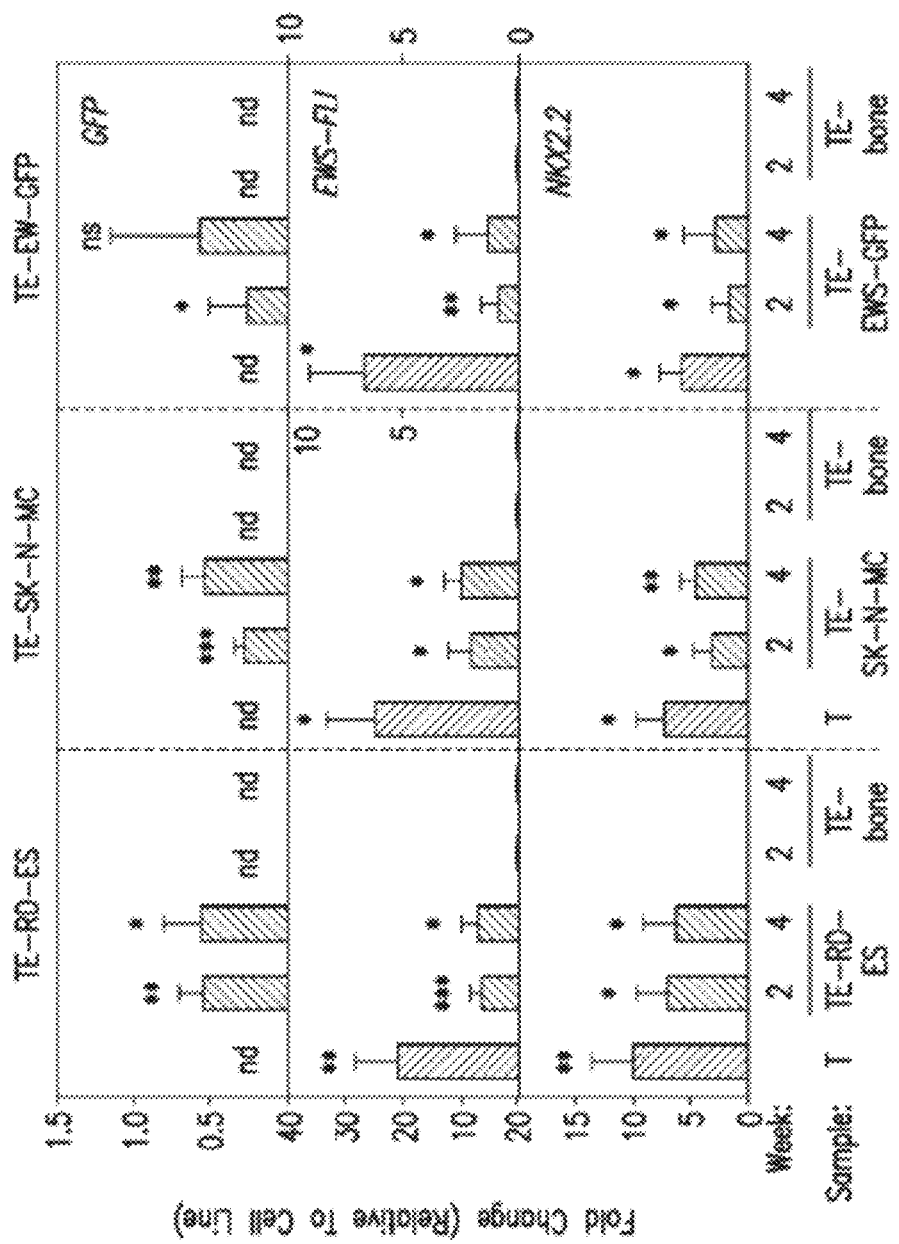
Figure 15C:
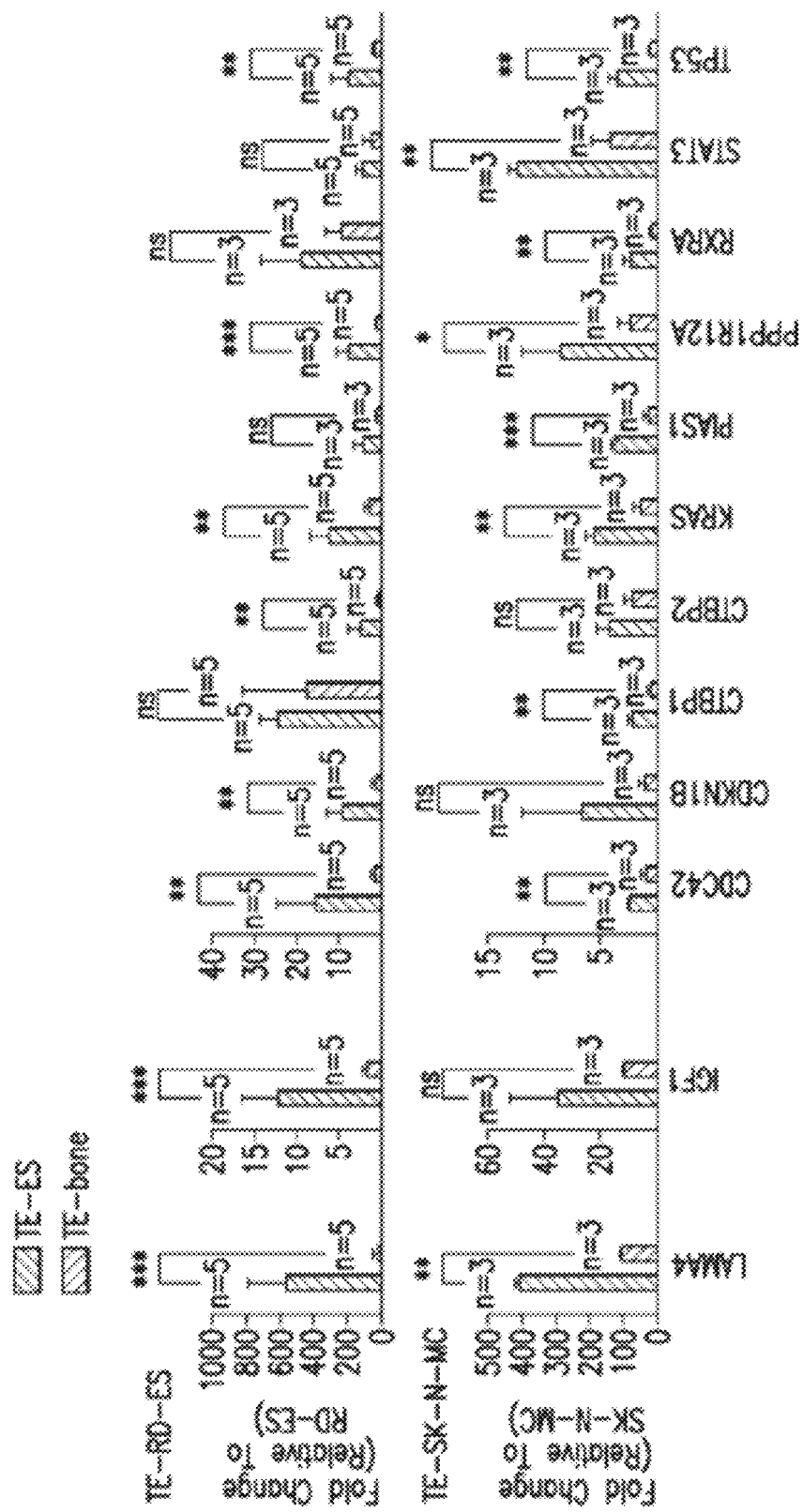

Referring to FIGS. 15A-C, characterization of TE-ES models is depicted. In FIG. 15A, Immunohistochemical staining of TE-bone and TE-ES models for Ewing's sarcoma marker CD99 at weeks 2 and 4 are shown. Insets represent negative controls without primary antibody. Representative images are shown (n=3 per condition). Counterstaining is performed with Hematoxylin QS (blue). FIG. 15B depicts qRT-PCR analysis of GFP, EWS-FLI and NKX2.2. FIG. 15C depicts qRT-PCR analysis of the ES genes expressed in tumors and not in cell lines cultured in 2D. In all cases, fold change is calculated by first normalizing to actin levels in the individual samples and then to the corresponding levels in cells cultured in 2D. Data are shown as Average±SD (n=3-5). Two-tailed Student's t-test was used to determine statistical significance. $*p<0.05$; $p<0.01$; $*p<0.001$; nd, not determined; ns, not significant; T, Ewing's sarcoma tumors.

Figure 20A:
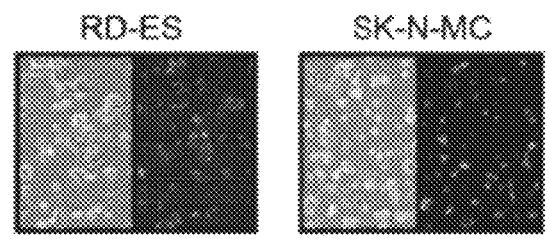
FIGS. 20A-D illustrate characterization of Ewing's sarcoma cell lines according to embodiments of the present disclosure.
Figure 20C:
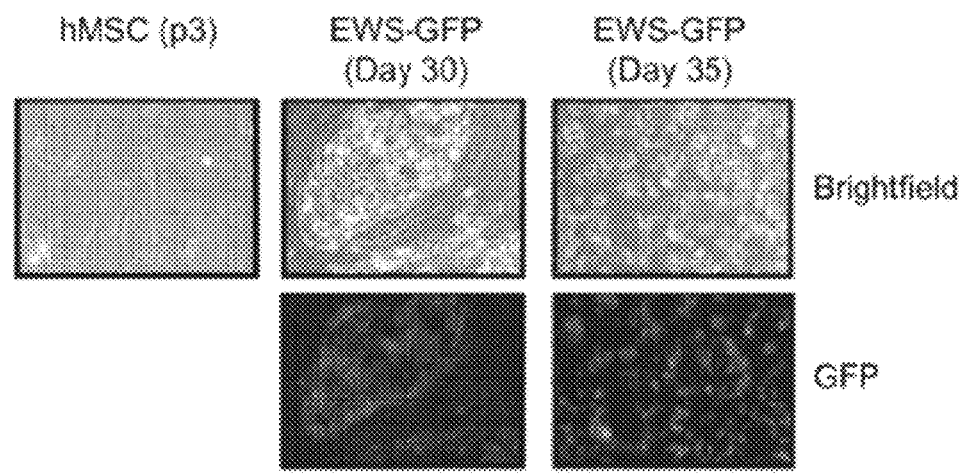
Figure 20B:
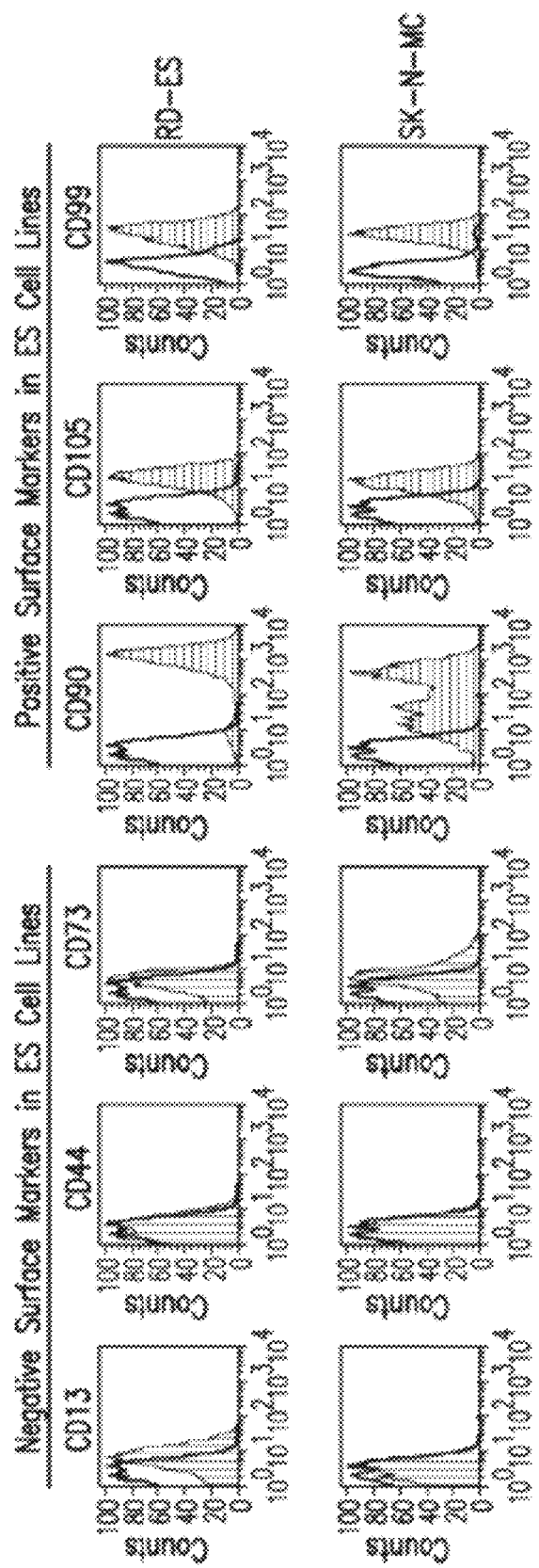
Figure 20D:
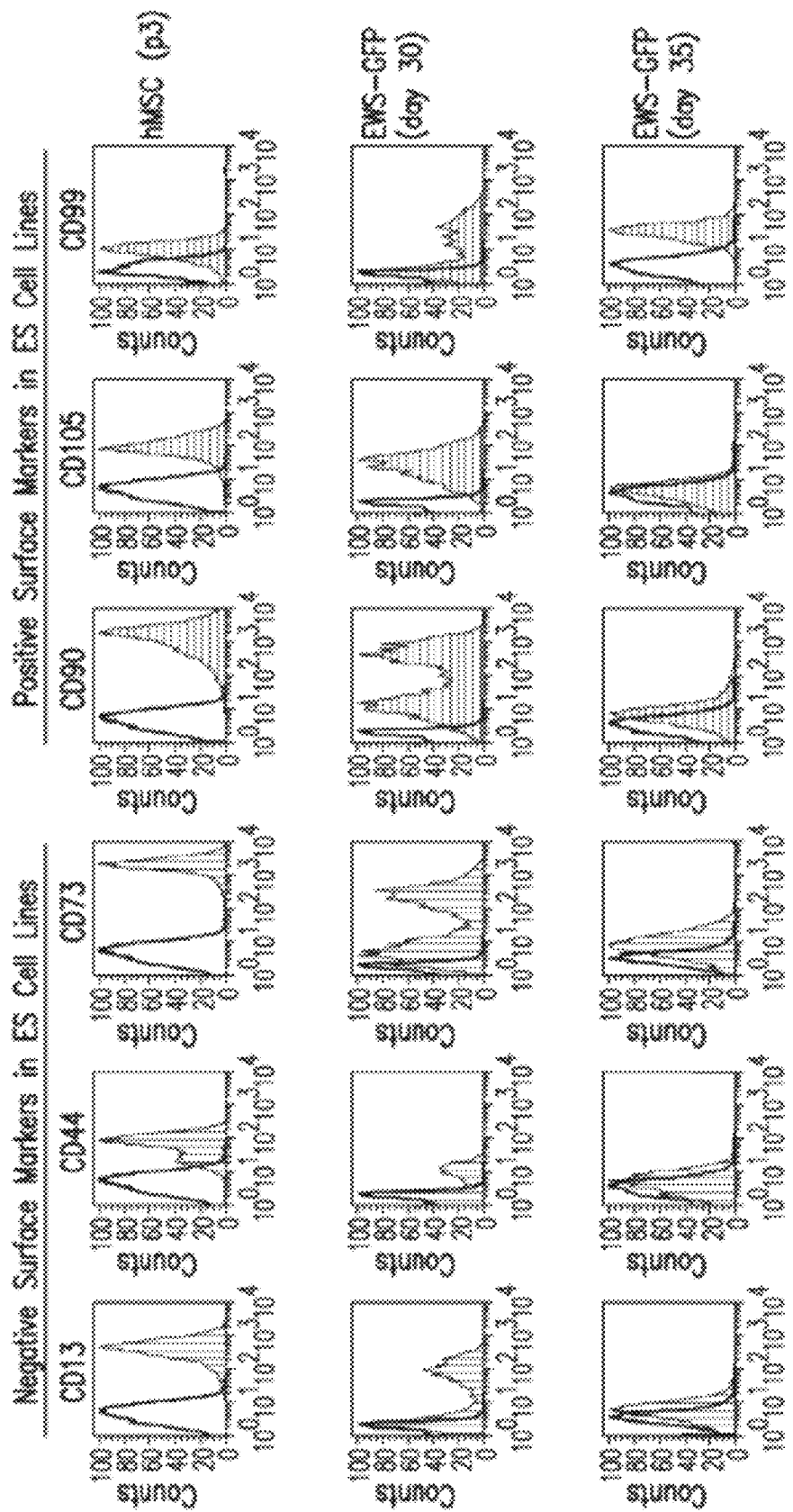

Two Ewing's sarcoma cell lines expressing GFP, RD-ES (primary bone tumor cell line) and SK-N-MC (primary cells originated from an Askin's tumor and metastasizing in the supraorbital area) are used to develop the tumor models (FIG. 20A). Surface markers (characterized by FACS) are CD13, CD44 and CD73 negative and CD90, CD105 and CD99 positive (FIG. 20B). In order to generate in vitro an ES cell line (EW-GFP cell line), a lentiviral plasmid containing the EWS/FLI mutation is introduced into hMSCs (FIG. 20C). Surface proteins expression in EW-GFP cell line (by flow cytometry) is compared to hMSCs, exhibiting high levels of the ES-related marker CD99 and losing CD13, CD44 and CD73 hMSC-specific markers (FIG. 20D).

Re-Expression of Focal Adhesion and Cancer-Related Genes

In order to validate the TE-ES model, histological sections were analyzed by hematoxylin-eosin staining, detecting large areas with small-round cells that were CD99 positive and surrounded by bone cells and ECM (FIG. 15A). GFP levels in TE-ES models and their cell line counterparts cultured in monolayers (by qRT-PCR) confirm expression in both cultures (FIG. 15B), demonstrating ES tissue formation and the presence of ES cells in the bone context. EWS-FLI mRNA and the EWSFLI target NKX2.2 are expressed at low levels in ES cell monolayers compared to native ES tumors from patients (FIG. 15B). Notably, both genes are up-regulated in all three TE-ES models, for all three cell lines described herein, showing a clear effect of the microenvironment in regulating ES gene profile (FIG. 15B).

Significant differences exist in gene expression between tumors from patients and cells cultured in monolayers, due to the flat, unnatural plastic environment. The presence or absence of expression of genes in 44 tumors from patients and 11 cell lines were analyzed by applying the barcode method to the Affymetrix Human Genome U1332 Plus 2 gene expression data of Savola et al.

599 genes are identified that were expressed in tumors but not in cell lines (Table 2). Comparing mRNA expression between the two cell lines (RD-ES and SK-N-MC) and 3 ES tumors by qRT-PCR, upregulation of 24 genes in ES tumors is confirmed. All these genes are related to focal adhesion and pathways in cancer (Table 3; FIGS. 21, 22, 23 and 24). Analysis of these 24 genes in the TE-RD-ES and TE-SK-N-MC models relative to their monolayer counterparts, confirms strong re-expression (fold change >3) for 12 genes (FIG. 15C).

IGF1 is one of the targets found and validated (12.2.+−.4.11 fold change in TE-RD-ES relative to RD-ES cell monolayers; 35.08.+−.16.84 fold change in TE-SKN-MC relative to SK-N-MC monolayers). IGF signal transduction pathway is thought to play a key role in ESFT development and proliferation. These results support the importance of tumor microenvironment for gene expression and suggest that TE-ES models recapitulate, at least in part, ES gene expression signatures.

Recapitulation of the Hypoxic and Glycolytic Tumor Phenotype

At early stages of cancer, tumors are avascular masses where oxygen and nutrients delivery are supplied by diffusion and therefore, growing in central areas is compromised. To maintain energy production, tumor cells respond and adapt to the hypoxic environment by increasing the amount of glycolytic enzymes and glucose transporters, such as GLUT1 and GLUT3, via the hypoxia-inducible factor-1 (HIF1α). Studies using tumor spheroids and tumor microregions in vivo, show an outer viable tumor (with proliferating cells), an inner hypoxic area (with quiescent adapted viable cells) and a central necrotic core where oxygen and glucose levels are critically low. The tumor model provides a native-like niche that mimics tumor heterogeneity in terms of oxygen and nutrients supply, as demonstrated by hypoxia in the center of the tissue constructs, but not in the outer areas (FIG. 19F).

Figure 16A:
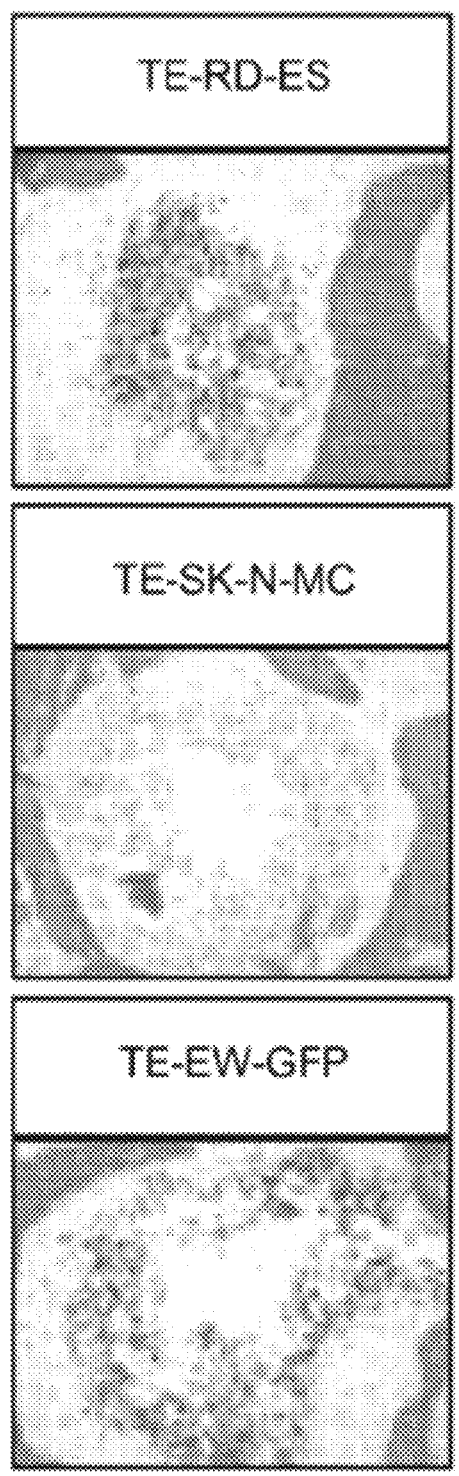
FIGS. 16A-D illustrate expression of hypoxic and glycolytic tumor phenotypes according to embodiments of the present disclosure.
Figure 16B:
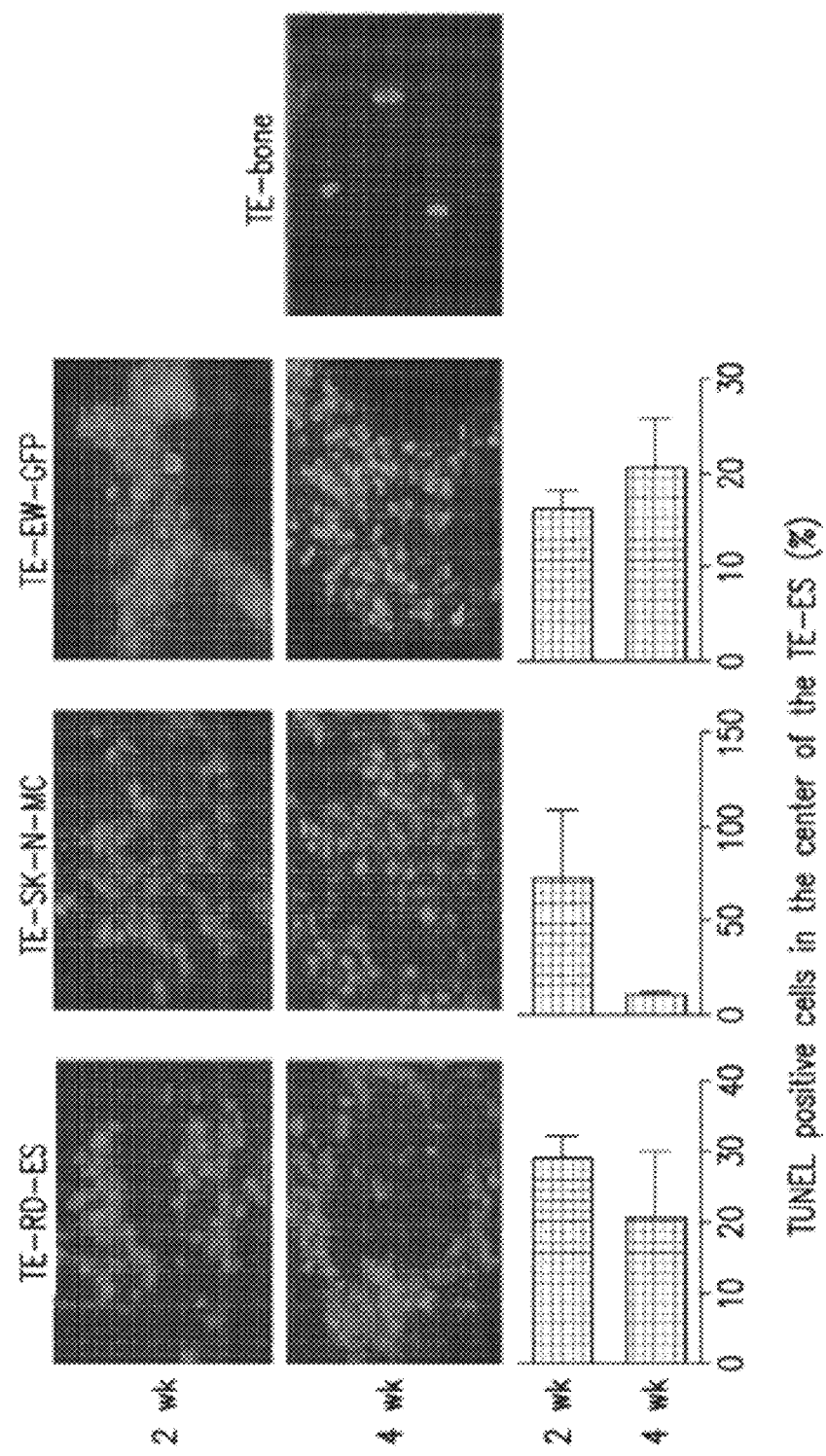
Figure 16C:
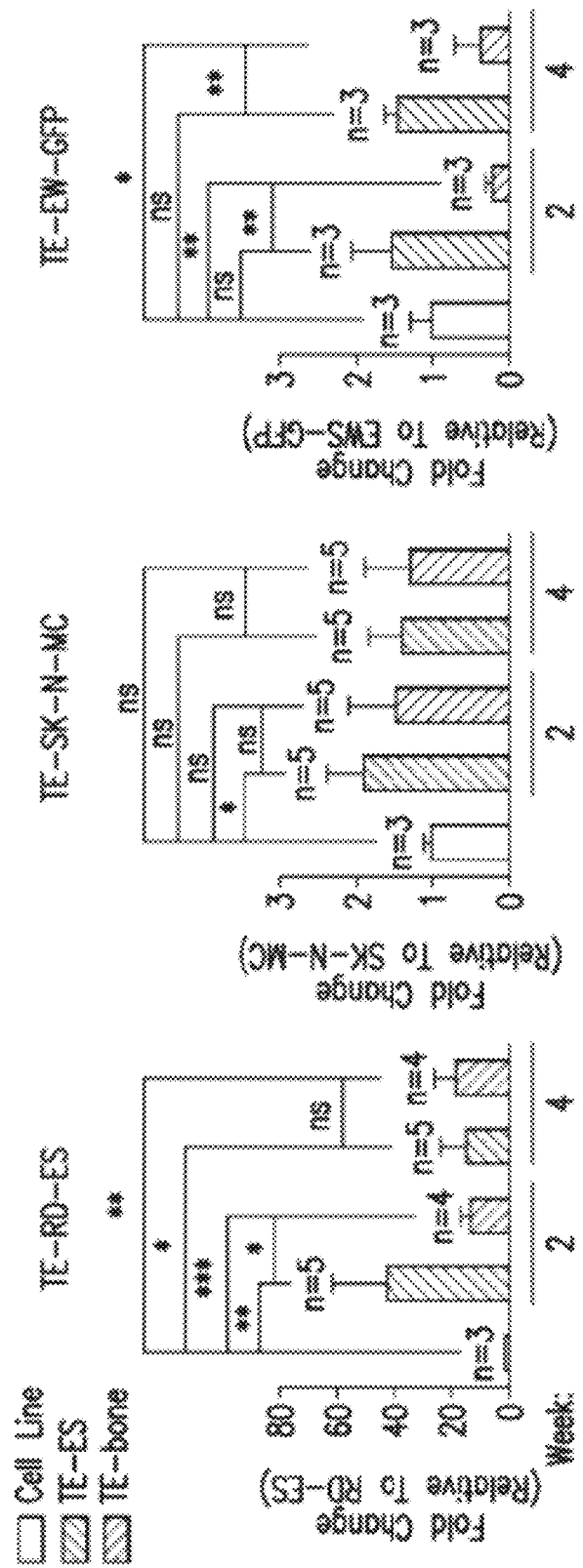

Referring to FIGS. 16A-C, expression of hypoxic and glycolytic tumor phenotypes are depicted. FIG. 16A shows necrotic areas in the inner part of TE-ES models identified by Hematoxylin and Eosin staining of TE-RDES, TE-SK-N-MC and TE-EW-GFP at week 2. Representative images are shown (n=3 per condition). FIG. 16B shows HIF1α mRNA levels in TE-ES models. Upper panel: representative pictures of TUNEL-stained inner areas. Apoptotic cells stain red; cell nuclei were stained by Hoechst 33342. Lower panel: Quantification of TUNEL positive cells in the inner part of the indicated TE-ES models. Fold change is calculated by first normalizing to actin levels in the individual samples and then to the corresponding levels in cells cultured in 2D. Data are shown as Average±SD (n=3-5). Statistical significance is determined by the two-tailed Student's t test. *$p<0.05$; $p<0.01$, *$p<0.001$; ns, not significant (FIG. 16C). TUNEL immunofluorescent staining of TE-ES and TE-bone in the center on the models. FIG. 19D shows Immunohistochemical staining of GLUT-1 in the indicated TE models over time. Counterstain: Hematoxylin QS (blue). Representative images are shown (n=3 per condition).

In order to evaluate whether TE-ES models recapitulate the initial steps of tumor generation, necrotic areas in the core of the tumor models were analyzed and compared the levels of HIF1α and GLUT1 to those in cell monolayers and TE-bone controls. First, focus on the construct interiors revealed necrotic areas similar to those observed in native tumors (FIG. 16A). TUNEL assays after 4 weeks of cultivation revealed higher cell death in the middle of the TE-SK-N-MC tumor model (73±36%) relative to TE-RD-ES (29±3%) and/or TE-EW-GFP (16±2%) (FIG. 16B). These results suggest that RD-ES and EW-GFP cell lines may be better adapted than SK-N-MC cell line to restrictive conditions at the centers of the constructs.

Figure 3A:
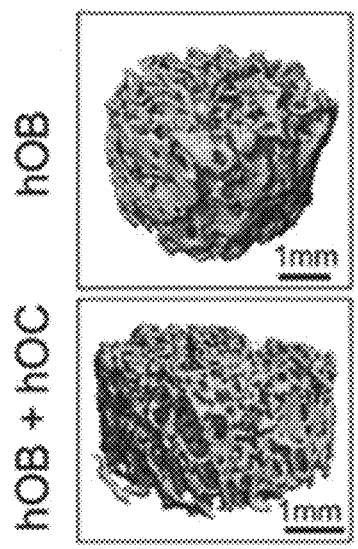
FIGS. 3A-C illustrates evaluation of bone microstructure in the tissue-engineered bone according to embodiments of the present disclosure.
Figure 3B:
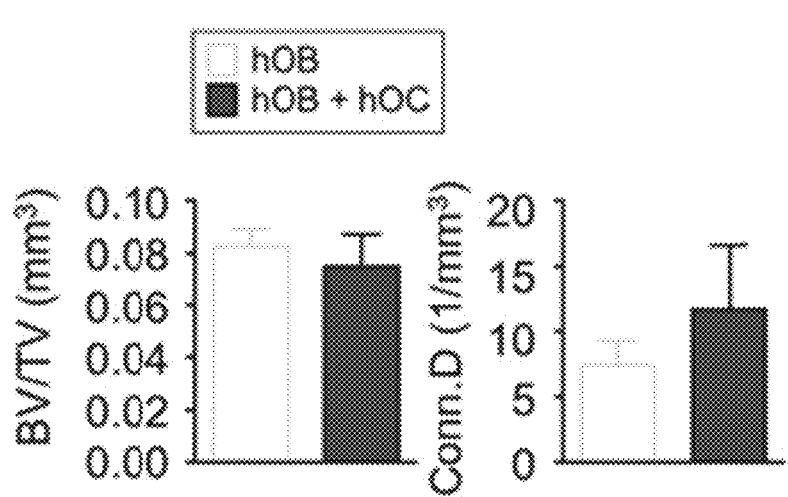
Figure 3C:
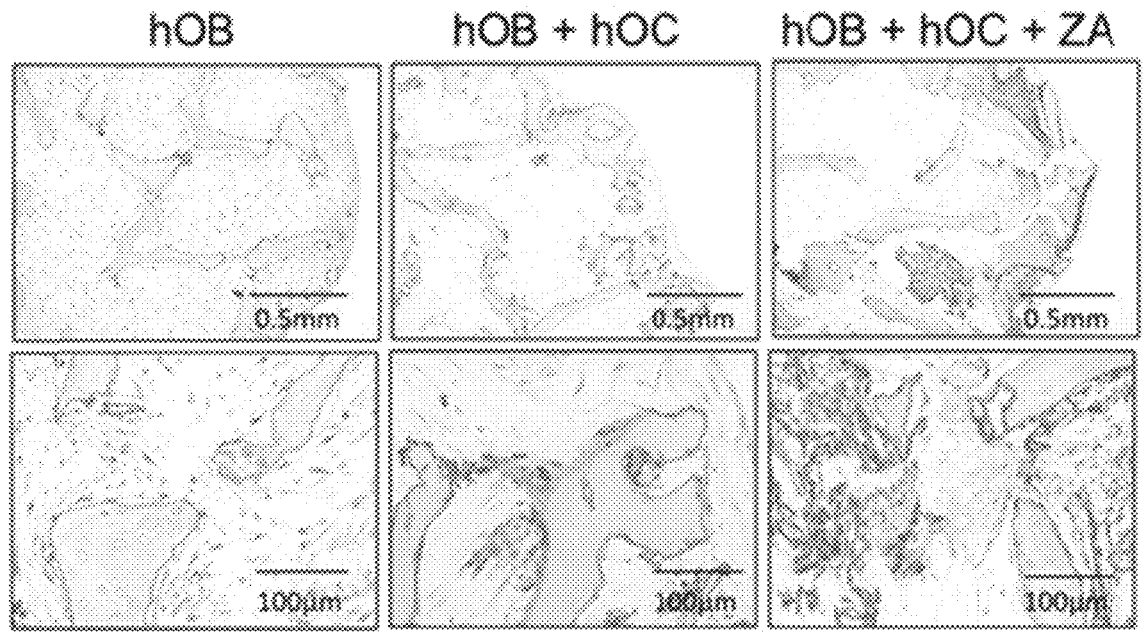

In response to hypoxia (at week 2), transcription levels of HIF1α were 40 times higher in the TE-RD-ES tumor model relatively to the RD-ES cell monolayers, and 30 times higher relatively to TE-bone. HIF1α expression decreased with time in culture, reaching at week 4 levels similar to those in TE-bone (FIG. 16C). Transcriptional expression of HIF1α was not significantly increased by hypoxia in TE-SK-N-MC and TE-EW-GFP models as compared to cell lines (FIG. 3C). Also, the SK-N-MC and EW-GFP cell lines express higher levels of HIF1α than the RD-ES line, and the expression levels in the SK-N-MC cells were comparable to those in TE-bone. These data suggest that tumor cells that have low transcriptional levels of HIF1α (RD-ES line) increase expression in order to adapt to hypoxic environment. In contrast, cell lines expressing high levels of HIF1 (SK-N-MC and EW-GFP) seem to be insensitive to hypoxia, at least at the transcriptional levels. HIF1α thus appears to play a protective role in the adaptation of tumor cells to hypoxia.

Figure 16D:
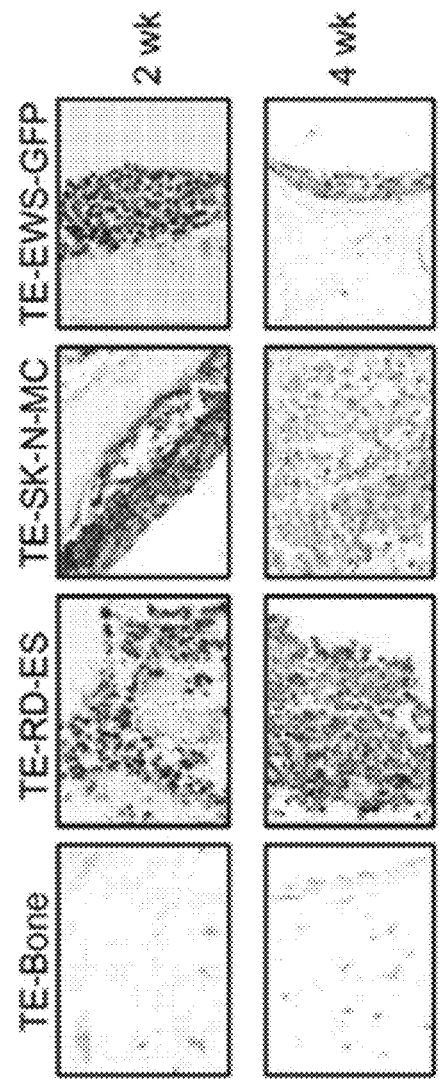

To assess the role of hypoxia in the induction of glycolytic response, the levels of GLUT1 protein in TE-bone and TE-ES models were examined. Very high levels of GLUT1 were observed favoring glucose uptake and tumor survival in inner areas where oxygen and medium supply are compromised (FIG. 16D). GLUT1 was expressed in necrotic areas in the TE-SK-N-MC model.

Taken together, these data demonstrate that the RD-ES cells expressing high levels of HIF1α adapt to hypoxia in the TE bone environment by recapitulating some aspects of hypoxic and glycolytic tumor phenotype, and mimicking inner-necrotic and outersurvival signatures. In comparison, the SK-N-MC and EW-GFP cells expressing low levels of HIF1α show less ability to adapt to hypoxic microenvironment.

Recapitulation of Angiogenic Ability and Vasculogenic Mimicry.

Figure 17A:
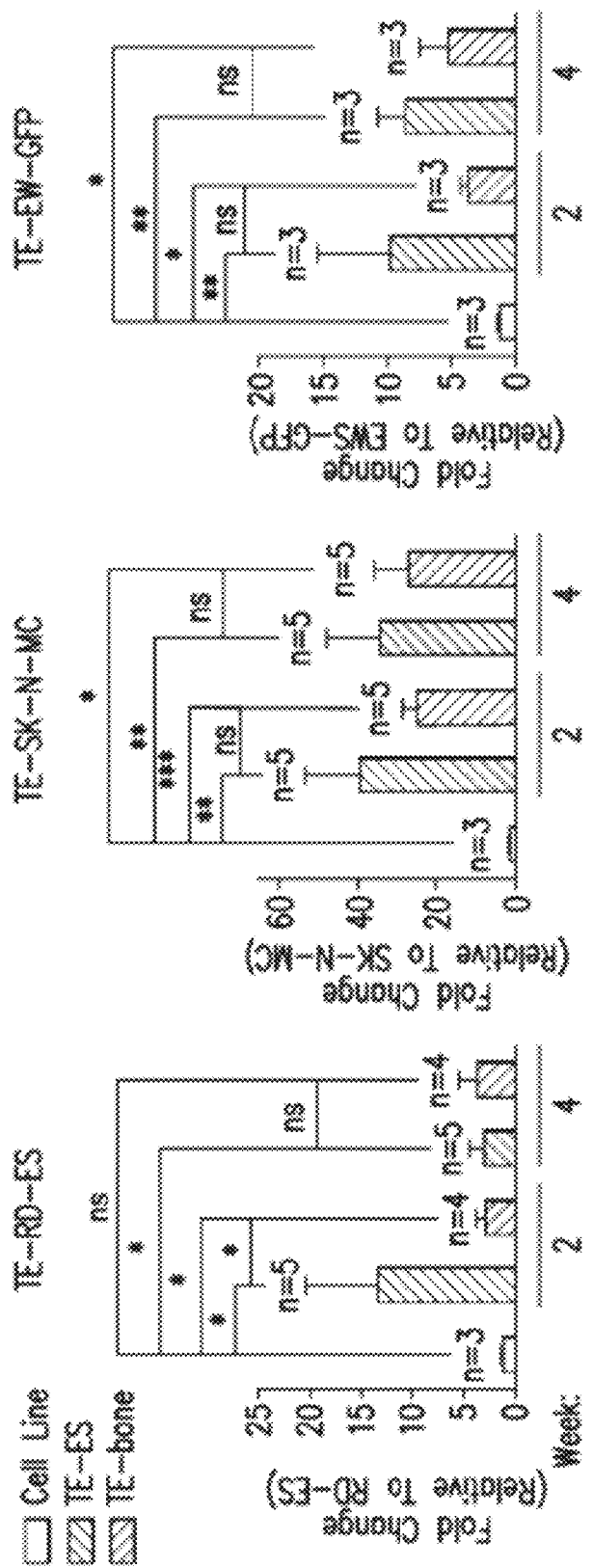
FIGS. 17A-D illustrate angiogenesis and vasculogenic mimicry according to embodiments of the present disclosure.
Figure 17B:
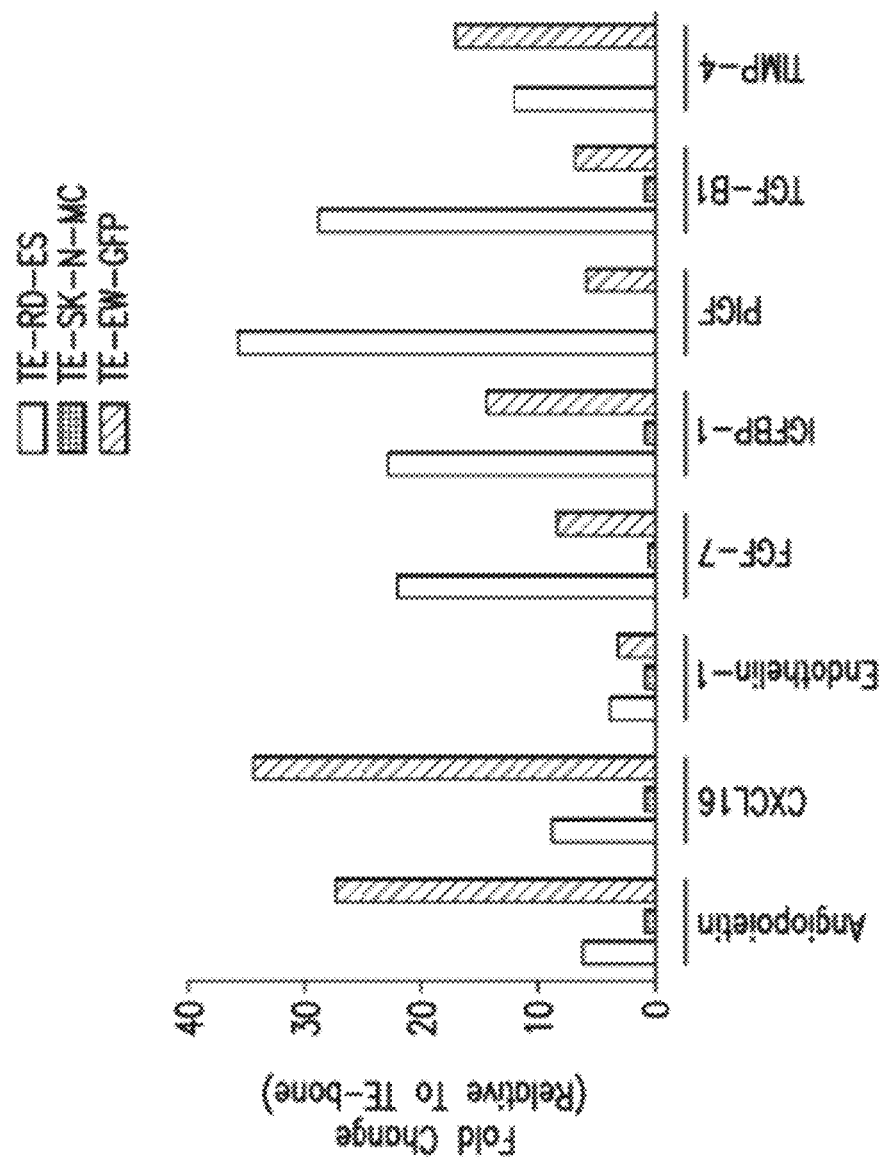
Figure 17C:
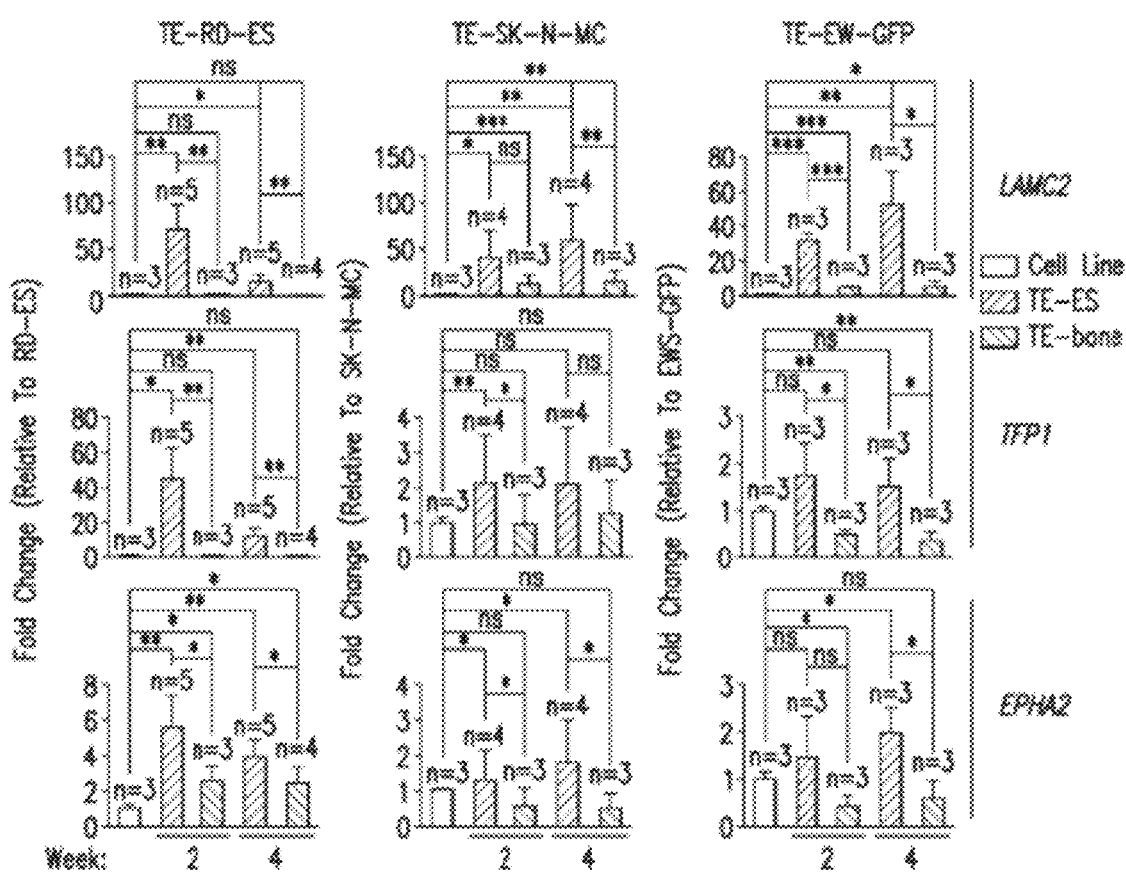
Figure 17D:
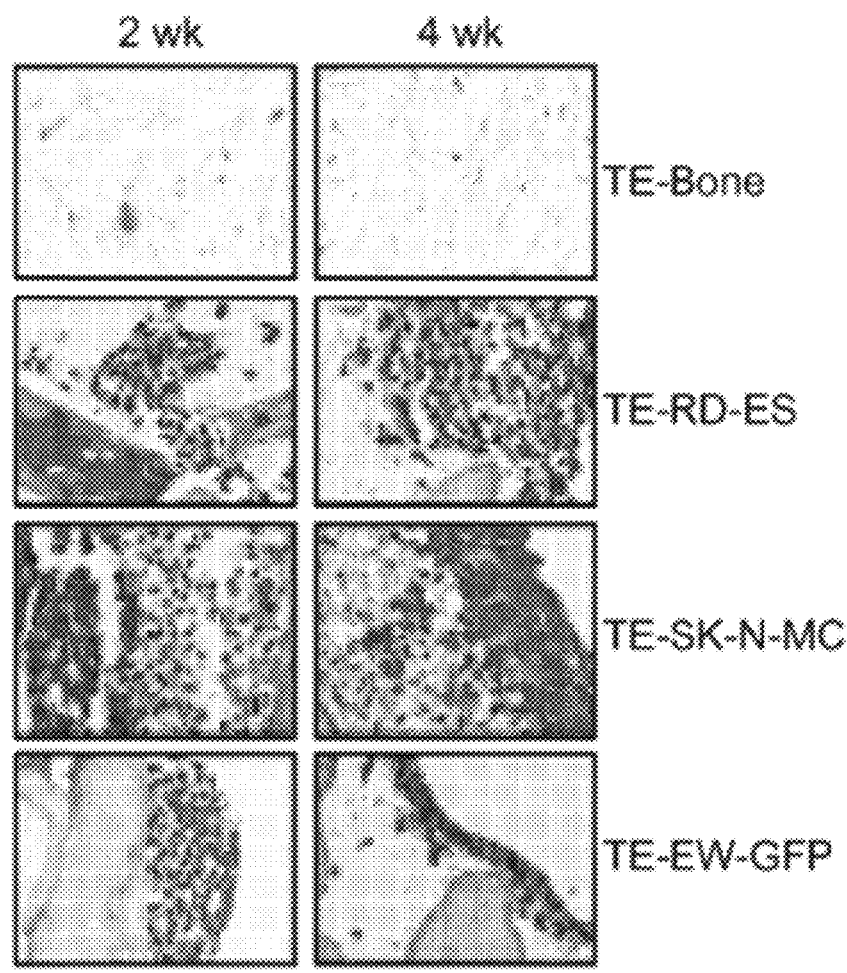
Figure 18A:
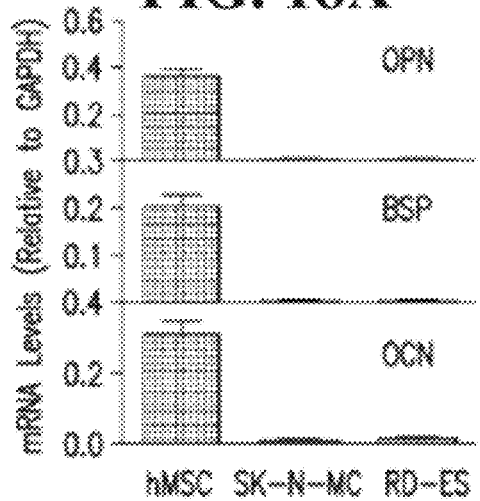
FIGS. 18A-C illustrate re-expression of tumor genes in a 3D tissue-engineered model of Ewing's sarcoma according to embodiments of the present disclosure.
Figure 18B:
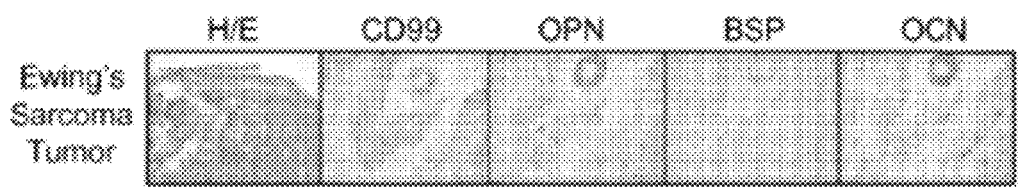
Figure 18C:
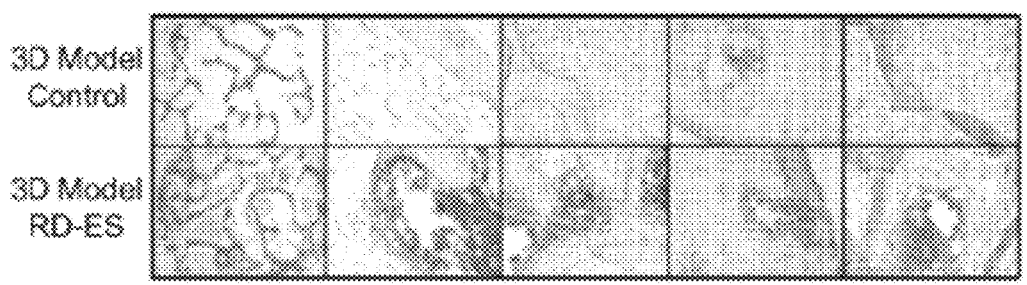

Referring to FIGS. 17A-D, angiogenesis and vasculogenic mimicry are depicted. FIG. 17A shows VEGFa mRNA levels in TEES models. Fold change is calculated by first normalizing to actin levels in the individual samples and then to the corresponding levels in cells cultured in 2D. Data are shown as Average±SD (n=3-5). Two-tailed Student's t-test is used to determine statistical significance. *$p<0.05$; $p<0.01$, *$p<0.001$; ns, not significant. FIG. 17B shows Angiogenesis-related proteins detection in TE-ES culture media. Expression levels of the indicated proteins were assessed by ELISA and compared with expression levels in the TE-bone counterparts. FIG. 17C shows qRT-PCR analysis of vasculogenic mimicry markers. Relative endogenous expression of each gene was normalized to actin and the fold change was obtained normalizing to the levels in corresponding cell lines cultured in 2D. Data are shown as Average±SD (n=3-5). Statistical significance was determined by the two-tailed Student's t test. *$p<0.05$; $p<0.01$, *$p<0.001$; ns, not significant. FIG. 17D shows representative images of PAS-stained sections from TE-bone and TE-ES models at week 2 and 4. Representative images are shown (n=3 per condition).

Tumor cells respond to oxygen and nutrient deprivation by promoting vascularization that maintains tumor growth and survival. Induction of vascular endothelial growth factor (VEGF-a) is an essential feature of tumor angiogenesis that is driven by hypoxia and mediated by HIF1α. To address whether hypoxia modulates angiogenic ability of the tumor, VEGF-a transcriptional levels in TE-ES models were analyze. High induction of VEGF-a in TE-RD-ES were found at week 2 compared to the RD-ES cell line and TE bone (FIG. 17A). Notably, levels decreased by week 4, as observed for HIF1α. In further support of the adaptive advantage of RD-ES cells cultured in TE-bone, VEGF-a mRNA levels were not significant higher in TE-SK-N-MC and TE-EW-GFP tumor models compared to TE-bone controls (FIG. 17A).

Then, angiogenic proteins secreted by TE-ES tumors were identified. By ELISA analysis of 24-hour supernatants, 56 human angiogenesis-related proteins were analyzed at week 2. Due to the differences in growth of different cell lines, it was not possible to directly compare secretion rates. However, these analyses clearly demonstrated that 8 proteins (Angiopoietin, CXCL16, Endothelin-1, FGF-7, IGFBP1-1, PlGF, TGF-B1 and TIMP4) were highly expressed in TE-RD-ES and TE-EW-GFP tumor models compared to TE-bone (fold change >3). In contrast, none of these proteins was detected in the TE-SK-N-MC tumor model. These results confirm that the SK-N-MC cells failed to induce essential adaptive elements to survive and proliferate in TE-bone (FIG. 17B). Interestingly, Endothelin-1 is implicated in ES proliferation and invasion while IGFBP1-1 prolongs the half-life of IGF-1, a well-known target gene of EWS-FLI and TGF-β1. These observations are consistent with previous studies, validating the current system.

Finally, vasculogenic mimicry (VM) was evaluated in TE-ES models. Native ES is featured by the presence of blood lakes and PAS positive cells expressing endothelium-associated genes. This property is known as VM and is stimulated by hypoxia. Thus, VM can provide functional perfusion channels composed only of tumor cells. The endothelium-associated genes (LAMC2, TFPI1 and EPHA2) were highly expressed in the TE-RD-ES at weeks 2 and 4 (FIG. 17C), confirming VM in the TE-RDES model.

Consistent with all other data, cells in the SK-N-MC model re-expressed VM genes as levels lower than those measured for the TE-RD-ES model. However, these expression levels were significantly upregulated at week 2 for TFP1 ($p<0.01$) and EPHA2 ($p<0.05$) and at week 4 for LAMC2 ($p<0.01$) and EPHA2 ($p<0.05$) as compared to SK-N-MC and TE-bone (FIG. 17C). Moreover, the TE-EW-GFP model expressed high levels of LAMC2, TFPI1 and EPHA2 at week 2 and 4 as compared to TE-bone (FIG. 17C). Tissue sections stained with PAS revealed positive areas in all the TE-ES models (except in TE-EW-GFP at week 2), as compared to negative-PAS TE-bone (FIG. 17D). Taken together, these results confirm that RD-ES cell line has higher capability to adapt to TE-bone than the SK-N-MC line.

According to various embodiments of the present disclosure, human tumor models predictive of native tumors in vitro are provided. Spheroids of tumor cells and porous scaffolds capture 3D aspects with control of oxygen, tension, and pH. Cancer is a complex disease where interactions between tumor cells and non-neoplastic cells play an important role in carcinogenesis. Herein, various embodiments provide models of human tumors, by incorporating Ewing's sarcoma cell spheroids into a bioengineered tridimensional bone niche, and thus enabling multiple interactions of tumor cells with other tumor cells, bone tissue matrix and bone cells.

Tumor cell lines cultured in 2D lose their transcriptional profiles and downregulate many genes implicated in cell-cell and cell-ECM interactions, such as focal adhesion genes. Gene expression profiles of cell lines cultured in monolayers are compared with native tumors, with focus on differentially expressed focal adhesion genes and cancer pathways. The induction of 12 genes in both TE-RD-ES and TE-SK-N-MC models evidence a major role of microenvironment in the acquirement of tumor expression profile. Models according to the present disclosure can thus be used for characterization of differentially expressed genes and help identify new tumor targets. As discussed above, induction of CDC42 and PPP1R12A is observed, both of which are related to Rho family of GTPases. Inhibition of some Rho pathway members through therapeutic compounds is applied in preclinical studies suggesting that CDC42 and PPP1R12A are potential candidates for ES therapy.

The bone niche has an important role in acquiring ESFT features to tumor cells, such as hypoxic and glycolytic phenotypes, angiogenesis potential and vasculogenic mimicry. The three ES cell lines discussed herein exhibit different behaviors in the bioengineered tumor model of the present disclosure. The primary bone tumor RD-ES cell line mimics ESFT signature, the in vitro-generated EWS-GFP cell line only in part and the metastatic SK-N-MC cell line was not able to recapitulate many of the tumor characteristics. These differences correlate to the expression levels of HIF1α (low in RD-ES cells, and high in SK-N-MC and EW-GFP cells), suggesting that HIF1α plays a protective role in the adaptation of tumor cells to hypoxia.

According to various embodiments of the present disclosure, tumor cells were studied within the 3D niche engineered to mimic the native host tissue. In various embodiments, the inclusion of stromal cells is provided, and tumor microvasculature and fine-tuned control of oxygen and nutrients are provided through the use of perfusion bioreactors.

A three-dimensional tumor model was built, with generated TE-bone containing mature osteoblasts and mature osteoclasts, differentiated for 12 days. FIG. 1 shows an overall approach to build a human tissue-engineered bone in vitro containing osteoblasts and osteoclasts. hMSC isolated from bone marrow aspirates are seeded within a decellularized bovine bone scaffold and differentiated toward mature osteoblasts. Then, monocytes CD14+ isolated from buffy coats from human blood are cocultured with osteoblasts and differentiated into mature osteoclasts.

Figure 2A:
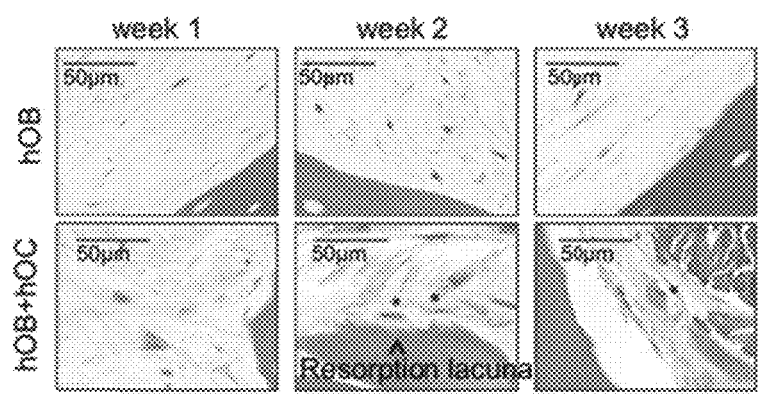
FIGS. 2A-F illustrate aspects of the characterization of osteoclasts within a tissue-engineered bone including osteoblasts according to embodiments of the present disclosure.
Figure 2B:
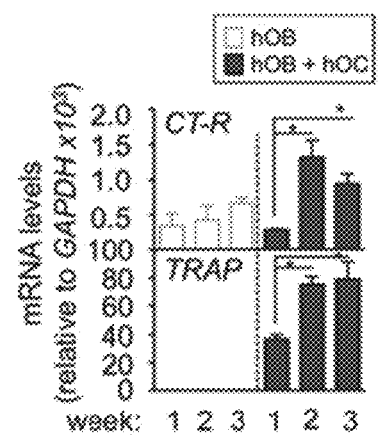
Figure 2C:
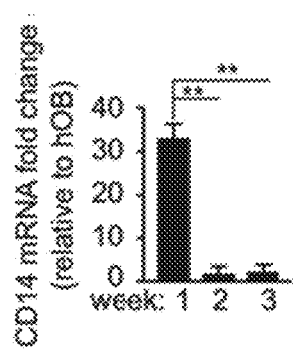

To evaluate osteoclast differentiation and activity, we analyzed the level of mRNA expression of calcitonin receptor and TRAP, and the genes expressed in osteoclasts and involved in cell differentiation in both types of constructs (hOB; hOB+hOC). FIG. 2A-F show aspects of the characterization of osteoclasts within a tissue-engineered bone containing osteoblasts. FIG. 2A shows Hematoxylin and Eosin staining detail of TE-bone showing activity (resorption lacunae) and typical morphology of mature osteoclasts at week 2 and 3 respectively, after seeding and differentiation of osteoclasts precursors. FIG. 2B shows the analysis of mRNA levels of osteoclasts markers by quantitative real-time PCR at week 1, 2 and 3 of monocytes CD14+ maturation. Comparison of TE-bone made with osteoblasts only (hOB) and TE-bone containing both osteoblasts and osteoclasts (hOB+hOC) is shown. Relative endogenous expression of osteoclasts markers was normalized to GAPDH levels. Error bars represent standard deviation of relative expression. FIG. 2C shows mRNA levels of CD14 relative to TE-bone hOB at the indicated time points. Relative endogenous expression of CD14 was normalized to GAPDH and error bars represent standard deviations of relative expression. Consistent with morphological studies, we observed an increase in calcitonin receptor and TRAP expression at week 2 (FIG. 2B). As expected, and consistent with the lifespan of human osteoclasts, calcitonin receptor (CT-R) mRNA levels showed a trend of decrease at week 3 (FIG. 2B). In parallel with the increasing expression of osteoclast markers, we observed significantly decreased levels of the monocyte marker CD14 at mRNA levels at week 2 and 3 (FIG. 2C).

Figure 2D:
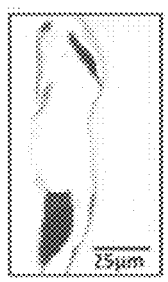
Figure 2E:
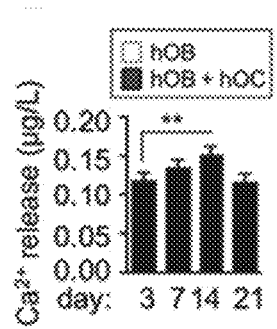
Figure 2F:
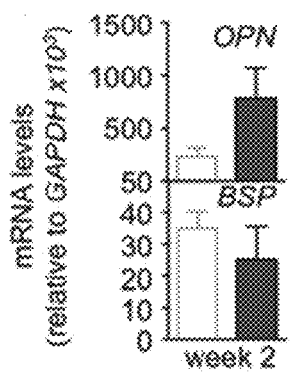

We assessed osteoclast activation by TRAP staining and calcium release to confirm the presence of TRAP+ cells at week 2 (FIGS. 2D and E). FIG. 2D shows TRAP staining of osteoclasts in co-culture with osteoblasts within the TE-bone model at week 3 of monocytes CD14+ differentiation. FIG. 2E shows calcium release levels from the TE-bone hOB+ hOC at indicated time points. The highest levels of $Ca^{2+}$ release activity were recorded at week 2 (FIG. 2E), suggesting 2 weeks as the most suitable time point for osteoclast studies in the 3D construct. FIG. 2F shows expression levels of osteoblasts markers by qRT-PCR in both TE-bone models at week 2 of monocytes CD14+ differentiation. mRNA levels of osteoblasts markers were normalized to GAPDH levels. Error bars represent standard deviation of relative expression. Statistical significance was determined by the two-tailed Student's t test; *p<0.05; p<0.01; *p<0.001. The mRNA levels of expression of osteoblast markers, OPN and BSP increased by week 2, as determined by qRT-PCR (FIG. 2F). OPN expression was not restricted to osteoblasts, as both osteoblasts and osteoclasts are capable of synthesizing OPN. These data confirm the presence of osteoclasts in coculture with osteoblasts in the bone tissue construct.

At least three weeks of cultivation is necessary for hMSC to differentiate into osteoblasts has been demonstrated. Differentiation protocol showed expression of high levels of osteoblast markers. CD14+ monocytes were co-cultured with the bone engineered from osteoblasts only for 1, 2 or 3 weeks in osteoclastogenic differentiation medium. Osteoclasts at week 2 were identified by morphological analysis, expression of osteoclasts markers and activity assays that confirmed physiological bone remodeling in vitro. The average lifespan of human osteoclasts is about 2-4 weeks, at week 2 the maximum peak of activity and after that, a slightly decreased activity in all the readouts was observed.

Then, we studied the noncellular bone compartment by assessing the bone microstructure with and without osteoclasts by microcomputed tomography (mCT) scans, to obtain quantitative bone structural parameters. FIGS. 3A-3C show aspects of the evaluation of bone microstructure in the TE bone. FIG. 3A shows representative three-dimensional architecture of engineered bone made with osteoblasts only (hOB) or both cell types (hOB+hOC) obtained by mCT imaging (n=3). We observed no differences in bone volume density (BV/TV) between the groups, suggesting a balance between bone production and bone resorption. A number of studies have demonstrated a direct relationship between osteoclast activity and bone remodeling and an increase in connectivity density. FIG. 3B shows plots of bone volume fraction (BV/TV) and connectivity density (Conn D) from microcomputed tomography (mCT) images of the two experimental groups (n=3). Importantly, and as expected, the Conn D was slightly higher in the group with osteoclasts (FIG. 3B). These data suggest that osteoclasts are metabolically active and capable of resorbing bone. We also analyzed the nonmineralized extracellular matrix component of the bone. We focused on BSP, as an important marker related to bone turnover that can be detected in serum, which also enhances osteoclast-mediated bone resorption. We also investigated the effects of a therapeutic reagent zoledronic acid (ZA) that has demonstrated efficacy in patients. ZA is a bisphosphonate commonly used to treat osteoclast-mediated bone loss in people with osteoporosis. The mechanism of action of ZA consists of inducing apoptosis in osteoclasts and inhibiting osteoclast-mediated bone resorption. To determine whether osteoblasts are still capable of producing matrix after coculture with osteoclasts, we inhibited osteoclasts with ZA (20 mM for 2 days), and evaluated BSP distribution by immunohistochemistry FIG. 3C shows immunohistochemical staining of BSP in engineered bone made with osteoblasts only (hOB) or both bone cell types (osteoblasts and osteoclasts; hOB+hOC) untreated and treated with zoledronic acid (ZA). Magnified views are shown in the bottom panels. Interestingly, we found differences in BSP protein distribution between both groups by immunohistochemistry. The group with only osteoblasts exhibited uniform distribution of BSP, in contrast to mosaic-patterned patches of BSP in the group with osteoclasts, consistent with bone remodeling in vitro. We observed a partial recovery of uniform BSP distribution in tissue constructs and, quite surprisingly, large patches of strong BSP staining after ZA treatment. This result confirms that osteoblasts are active and producing new matrix, which recapitulates in vitro the drug function observed in clinic. The response of tissue-engineered (TE) bone to ZA treatment was similar to those observed in animal models and patients, which reinforced the biomimetic value of the bone-engineered constructs comprising both osteoblasts and osteoclasts.

After 12 days of osteoclast differentiation, Ewing's sarcoma aggregates (cultured for 1 week to allow aggregate formation) were infused into the tissue-engineered bone, and the three-dimensional tumor model was maintained for one additional week in order to secure the activity of the osteoclasts. Living tissue-engineered bone niche provided a biomimetic and controlled environment for recapitulating ES growth and development was observed. ES cells cultured in this niche recapitulated lytic lesions found in patient's tumors (i.e. loss of BSP, decreased Bone Volume Density and Connectivity Density). Additionally, ZA, which modulates bone metabolism and has demonstrated some efficacy in Ewing's sarcoma patients, had effects in the tissue-engineered model that was comparable to those observed in animal studies.

Figure 4A:
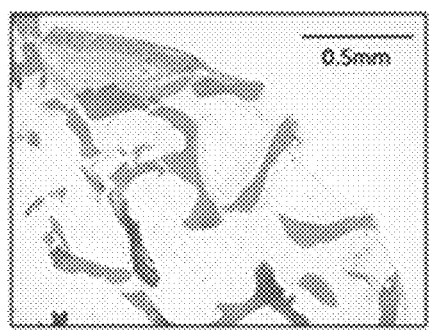
FIGS. 4A-C illustrates generation and characterization of the tissue-engineered model of Ewing's sarcoma according to embodiments of the present disclosure.
Figure 4B:
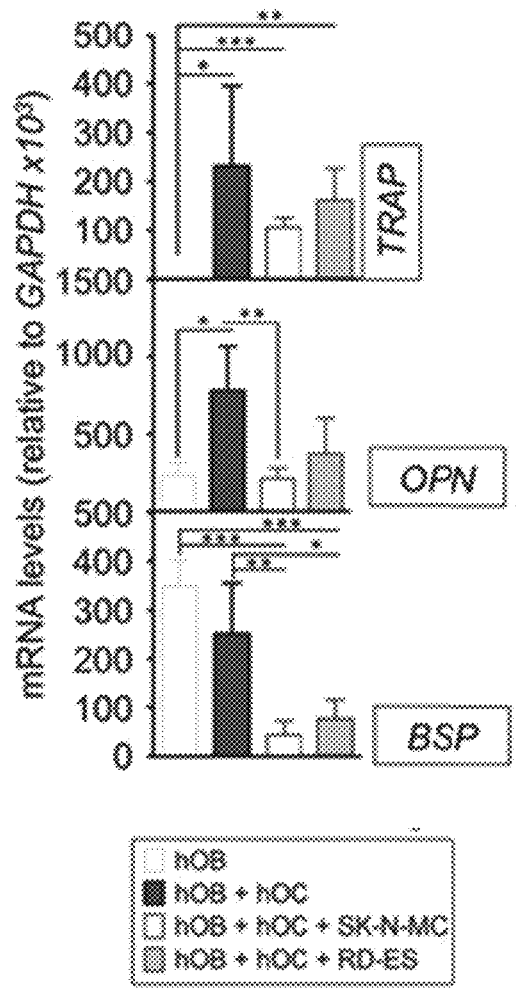
Figure 4C:
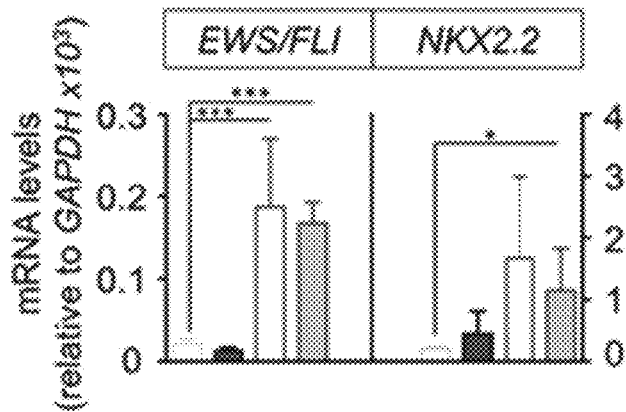

Two different Ewing's sarcoma models were generated: type 1 (using SK-N-MC cell line) and type 2 (using RD-ES cell line). FIG. 4A-C show aspects of the generation and characterization of the TE model of ES. FIG. 4A shows Hematoxylin and Eosin staining of the TE model of ES. Dash lined area demarks the tumor mass within the bone niche. FIG. 4B shows mRNA levels determined by qRT-PCR of ES markers, EWS/FLI, and NKX2.2, from the tissue-engineered bone with only osteoblasts (hOB), osteoblasts co-cultured with osteoclasts (hOB-hOC), and osteoblasts, osteoclasts, and ES cells (hOB-hOC+SK-N-MC cell line or RD-ES cell line). mRNA levels of indicated genes were normalized to GAPDH. Error bars represent standard deviation of relative expression. FIG. 4C shows qRT-PCR assay for the mRNA levels of TRAP, OPN, and BSP from the indicated experimental groups. mRNA levels of indicated genes were normalized to GAPDH. Error bars represent standard deviation of relative expression. Confirmation of the presence of cancer cells in the tumor model was done by morphological studies (as shown in FIG. 4A) and by evaluating the expression levels of EWS/FLI and NKX2.2 genes that are specifically expressed at high levels in Ewing's sarcoma (as shown in FIG. 4B). Additionally, decreases in BSP levels in the tumor model relatively to the corresponding bone constructs were observed (as shown in FIG. 4C).

Figure 5A:
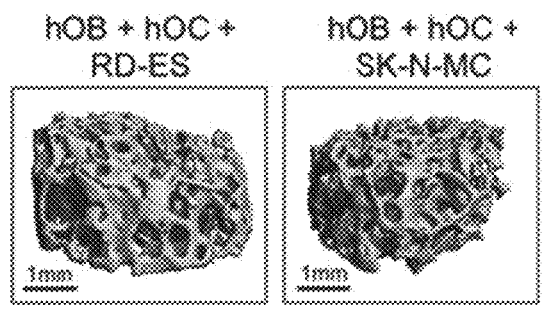
FIGS. 5A-C illustrates analysis of bone microstructure and zoledronic acid effects in the tissue-engineered model of Ewing's sarcoma according to embodiments of the present disclosure.
Figure 5B:
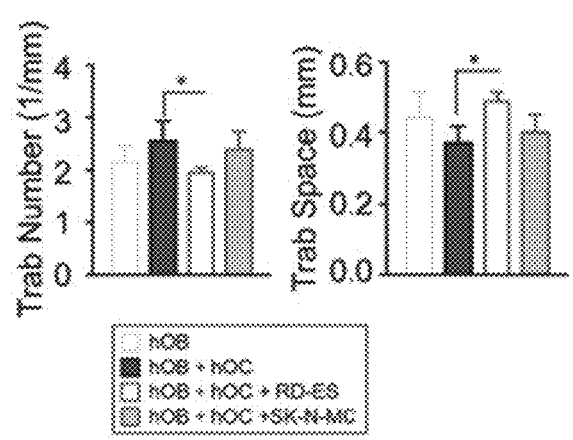
Figure 5C:
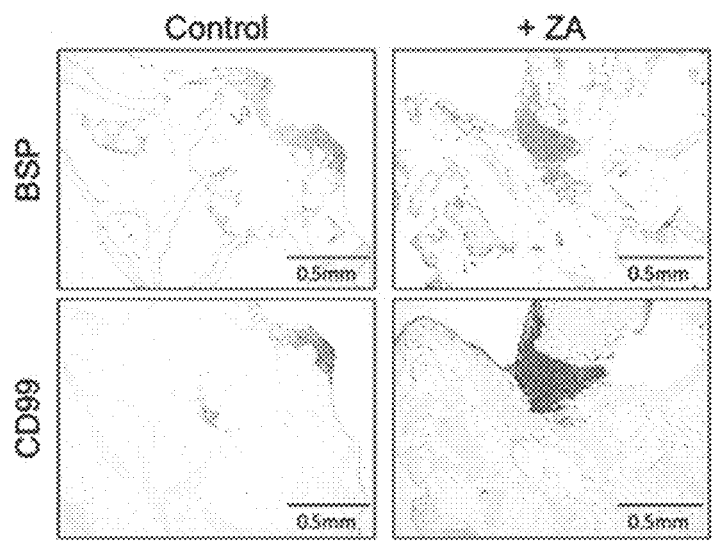
Figure 6A:
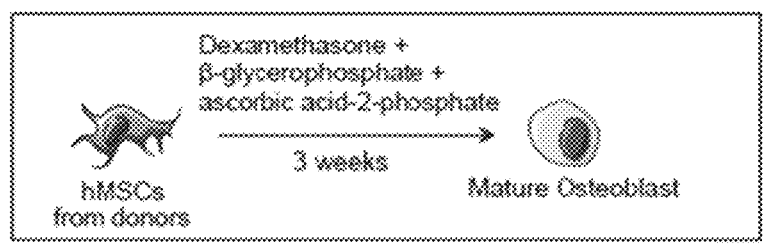
FIGS. 6A-C illustrates differentiation of human mesenchymal stem cells according to embodiments of the present disclosure.
Figure 6B:
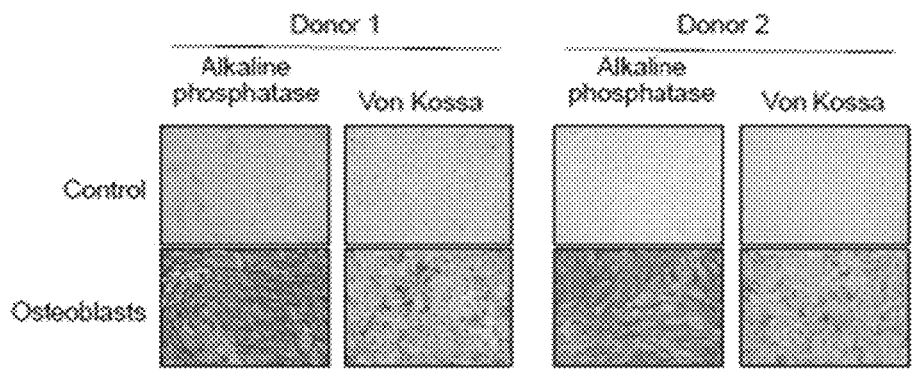
Figure 6C:
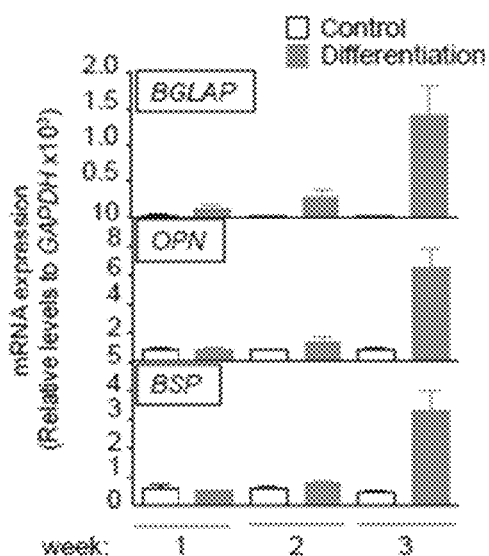

Interactions between cancer cells and bone cells orchestrate a vicious cycle in which tumor cells induce osteoclast activation and osteoblasts inhibition, resulting in bone resorption and osteolysis. FIG. 5A-C shows aspects of the analysis of bone micro-structure and zoledronic acid effects in the TE model of ES. To evaluate the possible effect of Ewing's sarcoma cells on bone resorption, CT scans of the tumor models with RD-ES and SK-N-MC cells were performed (as shown in FIG. 5A). FIG. 5A shows representative mCT scans of TE models of ES containing osteooblasts (hOB) and osteoclasts (hOC) in coculture with the indicated ES cells (SK-N-MC and RD-ES) (n=3 per group). FIG. 5B shows structural parameters from the indicated experimental groups measured with mCT analyses and depicted as histograms (n=3 per group). Consistent with the previous studies in animal models of bone osteolytic tumors, a marked decrease in Bone Volume Density per unit Tissue Volume (BV/TV) in the constructs with Ewing's sarcoma cells was observed. The same tendency was observed for the Connectivity Density (Conn. D) parameter. Conversely, an increase for trabecular space values was found (FIG. 5B). These results suggest that Ewing' sarcoma cells induce bone resorption and osteoclast activation. Calcium release in tumor model supernatants was quantified, but we did not observe any difference compared to the bone construct with osteoclasts.

For further characterization, bone sialoprotein (BSP) distribution in the tumor model was examined by immunohistochemistry. FIG. 5C shows images of representative immuno-histochemical staining for BSP and CD99 in the TE models of ES (SK-N-MC cell line) that was untreated (control) or treated with +ZA. CD99-positive regions correspond to SK-N-MC cells. Counterstaining was performed with Hematoxylin QS (blue) (n=3 per group). Bone extracellular matrix lacking BSP was observed, while BSP co-localized with the CD99 Ewing's sarcoma marker (as shown in FIG. 5C). The capability of Ewing's sarcoma cells to produce BSP in a 3D environment was reported. Thus, BSP observed (as shown in FIG. 5C) could be secreted by Ewing's sarcoma cells, and not by the osteoblasts. This result reinforces the idea of Ewing's sarcoma cell-mediated bone matrix degradation. Zoledronic acid (ZA) has been shown to target both osteoclasts and Ewing's sarcoma cells. To determine whether cancer cells inhibit the ability of osteoblasts to produce BSP, tumor model was treated with ZA (20 μL or 2 days). BSP was detectable in the whole construct after treatment that suggests re-activation of osteoblasts (as shown in FIG. 5C), recapitulating the effects observed in mice models.

Tissue-engineered models of human tumors are now designed to conform to the three R's: Reduction, Refinement and Replacement. The three-dimensional models of ES can faithfully recapitulate the osteolytic process observed in the patients' bones. While animal models have limitations, they display a range of complexity associated with systemic factors that tissue-engineered systems still lack. A challenging and desirable goal is to engineer a bone niche that can maintain osteoclast and osteoblast precursors in undifferentiated state, in order to maintain active osteolysis and self-renewal over long periods of time. A less biomimetic but perhaps more feasible option is to introduce medium perfusion into the system, and to infuse bone precursors at timed intervals. The described three-dimensional model has high transformative potential, as the three-dimensional model enables critical advances in tumor modeling under conditions predictive of human physiology.

In alternate embodiment, the three-dimensional tissue-engineered model described above is for studying tumor exosomes, designed to mimic the native tumor microenvironment. As a clinically relevant example, Ewing's sarcoma (ES) is selected, a solid tumor with aggressive biologic behavior, that affects children and young adults, and is associated with frequent metastases and poor prognosis. ES is characterized by chromosomal rearrangements of the EWSRJ (22q12) gene with one of the members of the ETS family of transcription factors: the FLI1 gene (11q24) in 85% of cases. Expression of EWSRI-FLI1 fusion protein has been the main approach to study the development of ES. Recent studies also demonstrated the presence of EWSR1-FLI1 mRNA in ES-derived exosomes.

Human mesenchymal stem cells (hMSC) were the only cell type found to provide an appropriate cellular context for EWSRI-FLI1 expression, supporting the notion that Ewing's sarcoma is derived from hMSCs. Surprisingly, hMSCs were unable to form tumors in immunocompromised mice. The studies show that EWSRI-FLI1 is necessary to activate the oncogenic program, but not sufficient for oncogenic transformation of hMSCs. Therefore, recent research has focused on downstream transcriptional targets such as EZH2. EWSRI-FL11 was shown to bind to the EZH2 promoter and to induce EZH2 expression in Ewing's sarcoma in vivo and hMSCs in vitro. The EZH2 methyltransferase is a major component of the polycomb repressive complex 2 (PRC2) that is related to transcriptional repression of tumor suppressors such as p4ARF and p16INK4a. EZH2 is involved in the maintenance of cell pluripotency and oncogenic transformation of Ewing's sarcoma cells. Additionally, expression of EZH2 correlates with poor prognosis in several tumor types including ES. Thus far, the presence of EZH2 in ES-derived exosomes has not been documented.

Figure 10A:
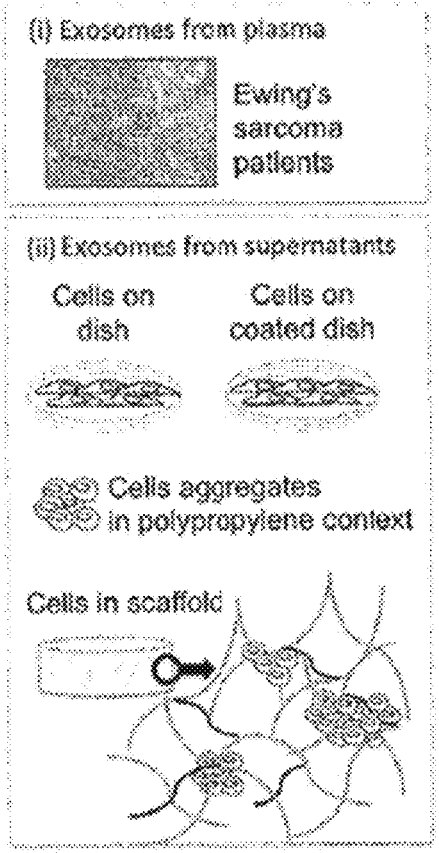
FIGS. 10A-F illustrates Ewing's sarcoma type 1 model in a 3-dimensional Collagen 1-Hyaluronic acid scaffold.

The effects of the microenvironment on tumor-derived exosomes, and the effects of exosomes on cell populations in the bone niche are studied and ES cells are cultured in 3-dimensional biomaterial scaffolds designed to mimic the biological and mechanical properties of ES. The size distributions and EZH2 mRNA cargo are analyzed and compared in exosomes from the plasma of patients and culture medium from monolayers (in culture dishes with different matrix coatings), cell aggregates (in polypropylene), and 3D tissue-engineered tumors (in scaffolds resembling native tumor matrix) as shown in FIG. 10A, the transfer of EZH2 mRNA from tumor-secreted exosomes to the mesenchymal stem cells is investigated, osteoblasts and osteoclasts of the ES bone niche.

Human mesenchymal stem cells (hMSCs): unprocessed human bone marrow aspirates were purchased from Lonza. Aspirates from two different donors: donor 1 (code 26737) and donor 2 (code 26798). Human mesenchymal stem cells (hMSCs) were isolated from these aspirates, characterized and prepared as in our previous studies.

Derivation of osteoblasts from hMSCs: Cell culture and differentiation into osteoblasts were carried out as per protocol. Briefly, hMSC were cultured in expansion medium (DMEM supplemented with 10% (v/v) Hyclone FBS, 1% penicillin/streptomycin and 1 ng/mL of basic fibroblast growth factorb, bFGF). Differentiation into osteoblasts was performed by culturing hMSC in osteoblast differentiation medium (DMEM supplemented with 10% v/v Hyclone FBS and 1% penicillin/streptomycin, 1 NM dexamethasone, 10 mM β-glycerophosphate, 50 NM ascorbic acid-2-phosphate) for 3 weeks. Due to the highly osteogenic nature of the mineralized bone scaffolds used to culture the cells, the supplementation of BMP-2 was not necessary. hMSC and osteoblasts were cultured at 37° C. in a humidified incubator at 5% $CO_2$.

Isolation of monocytes: Peripheral blood mononuclear cells (PBMC) were isolated from buffy coats of human blood (fully de-identified samples obtained from the New York Blood Center) by density gradient centrifugation with Ficoll-paque PLUS (17-1440-02, GE Healthcare). Monocytes were derived from the PBMC preparations by immunomagnetic isolation (The big easy EasySep Magnet, #180001, Stem Cell Technologies) using a negative selection (EasySep Human Monocyte Isolation Kit #19359, Stem Cell Technologies), following the manufacturer's protocol. Then, $8\times10^6$ monocytes were cultured on 25 $cm^2$ ultra-low attachment flasks (Corning #3815) with 10 mL of maintenance medium: RPMI 1640 (ATCC, 30-2001) supplemented with 10% heat inactivated human serum (Corning #35-060), 1% penicillin/streptomycin, 20 ng/ml Recombinant Human M-CSF (Prepotech #300-25) during 2 days at 37° C. in a humidified incubator at 5% $CO_2$.

Derivation of osteoclasts from human monocytes: Human CD14+ monocytes were incubated with differentiation medium consisting of Minimum Essential Medium Eagle Alpha modification (α-MEM, Sigma, M4526) supplemented with 10% (v/v) heat inactivated Hyclone FBS, 1% penicillin/streptomycin, L-Glutamine (Gibco #25030-081), 20 ng/ml Recombinant Human M-CSF (Prepotech #300-25) and 40 ng/ml Recombinant Human sRANK Ligand (Prepotech #310-01). Cytokines were replenished every 3 days. Cells were maintained at 37° C. in a humidified incubator at 5% $CO_2$.

Resorption pit assay: Human CD14+ monocytes were plated into 24-well osteo assay plate (100,000 cells per well) (Corning, #3987) and cultured either in complete osteoclast differentiation medium, or without sRANKL as a control for cell differentiation. At different time points, 10% bleach solution was added to each well and cells were incubated for 10 minutes at room temperature. Then, wells were washed 3 times with distilled water and air dried overnight. Resorption pits were visualized at 10× magnification and a blue filter was used to improve the quality of the image.

Engineered bone tissue containing osteoblasts and osteoclasts: Scaffolds (4 mm diameter×4 mm high plugs) were prepared from decellularized bovine bone. hMSC ($1.5 \times 10^6$ per scaffold) were seeded into each scaffold and cultured with osteoblasts differentiation medium for 3 weeks, with a complete medium change twice a week. The scaffolds were then incubated in osteoclasts differentiation medium without cytokines (M-CSF and sRANK Lingand) for 1 hour and bisected. One half of the tissue construct was placed into a 4 mm×4 mm (inner diameter×height) PDMS ring and cultured with the addition of 500,000 osteoclasts in 10 µl of osteoclast differentiation medium for 30 minutes at 37° C. in a humidified incubator at 5% $CO_2$. The scaffolds were flipped and seeded again with 500,000 osteoclasts in 10 µl of osteoclast differentiation medium for 30 minutes at 37° C. in a humidified incubator at 5% $CO_2$.

The resulting scaffolds were placed into low attachment six well plates (1 construct per well) containing 5 ml of osteoclast differentiation medium. Medium was changed twice a week. This group was termed hOB+hOC. The other half of each tissue scaffolds that contained only osteoblasts was termed the hOB group, and cultured with osteoclast differentiation medium without cytokines.

Tissue engineered tumor model: Tumor cells were introduced into the osteoblast-osteoclast bone niche using methods from our previous studies. Aggregates of Ewing's sarcoma cells (RD-ES or SK-NMC cell lines) containing $0.3 \times 10^6$ cells were injected into the tissue constructs (3 aggregates per construct) and the resulting cancer cell-bone constructs were cultured for 1 week in osteoclast differentiation medium without supplemental cytokines. This group was termed hOB+hOC+RD-ES or hOB+hOC+SK-N-MC, depending on the Ewing's sarcoma cell line used for model generation. Bone tissue constructs (hOB+hOC) without cancer cells were used as a control.

Immunohistochemistry stainings were performed using primary antibodies specific to CD99 (dilution 1:500; Signet antibodies, SIG-3620) and bone sialoprotein (dilution 1:500, Abcam, ab33022), and developed using the Vector Elite ABC kit (Vector Laboratories), following manufacturer instructions. Briefly, sections were blocked with serum for 30 minutes and incubated with the primary antibody overnight at 4° C. After washing with PBS, samples were incubated with secondary antibodies and developed (Vector Laboratories). Negative controls were prepared by omitting the primary antibody step. Alkaline phosphatase and von Kossa stainings were performed as previously described. Tartrate-resistant Acidic Phosphatase (TRAP) staining was performed using the K-assay (Kamiya Biomedical Company #KY-008).

Monocytes (300,000 per well in 6-well plates) were cultured in complete osteoclast differentiation medium, or without sRANKL as a control for differentiation. At timed intervals (1, 2 and 3 weeks), culture medium was removed and cells were fixed and stained for TRAP, by following the manufacturer's protocol.

Tissue-engineered bone constructs were fixed in 10% formalin, decalcified in 12.5% EDTA, embedded in paraffin, sectioned to 4 µm, stained for TRAP according to the manufacturer's instructions, and counterstained with Hematoxylin QS (Vector Labs).

Calcium release analysis: Supernatants of culture medium were sampled (1 mL per sample), snap frozen in liquid nitrogen and stored at −80° C. The $Ca^{2+}$ concentrations were analyzed using the $Ca^{2+}$ Detection Kit (Abcam, ab102505) following the manufacturer protocol. Briefly, supernatants were centrifuged for 2-5 minutes at 4° C. at top speed using a cold microcentrifuge to remove any insoluble material. Supernatants were collected and transferred to clean tubes. 90 µL of the chromogenic reagent were added to each sample. The chromogenic complex formed between calcium ions and o-cresolphthalein was measured using a microplate reader at OD=575 nm. The measured absorbance values for each standard were plotted as a function of the final concentration of calcium. Finally, the calcium concentrations in the samples were calculated from the standard curve.

Micro-Computed Tomography (NCT): Samples were scanned and analyzed using a Scanco VivaCT 40 micro-computed tomography system (Scanco Medical, Basserdorf, Switzerland). Scans were performed using 55 kVp, 109 µA, and 200 ms integration time, and resulted in images with 21 pm isotropic voxel size. Reconstructed images were smoothed using a Gaussian filter (sigma 0.8, support 1), segmented using a global threshold of 30% maximum gray-scale value, and processed using the standard trabecular morphometry evaluation.

Collection of the tissue samples from patients: Fully de-identified Ewing's sarcoma tumors were obtained from the Columbia University Tissue Bank, on an IRB-approved protocol. Frozen tissue samples from three different patients were cut into sets of contiguous sections for mechanical, histological, and immunohistochemical studies.

Fully de-identified blood plasma samples from Ewing's sarcoma patients for exosome isolation and characterization were collected in Dr. Moore's laboratory on an IRB-approved protocol at Memorial Sloan-Kettering Cancer Centre (New York, USA).

Scaffold preparation: Highly porous scaffolds were produced from Col 1-HA solutions by freeze-drying. A 1% (wt/v) solution was prepared from low molecular weight (10-20 kDa) or high molecular weight (500 kDa) Sodium Hyaluronate (HA, Lifecore, US) in distilled water. Four parts of Collagen 1 solution (8-11 mg/ml in 0.02 N acetic acid, Corning, US) were mixed with one part of HA solution (4:1). After mixing, 200 µl of the solution was spread over an 8 mm×5.5 mm mold, frozen at −40° C. for 4 hours, and sublimed at −40° C. overnight under a vacuum of <100 mTorr. Lyophilized collagen-HA scaffolds were cross-linked with a water-soluble carbodiimide using a previously described method. The scaffolds were immersed in 95% ethanol solution containing 33 mM EDC (Sigma-Aldrich Co. Ltd., UK) and 6 mM NHS (Sigma-Aldrich Co. Ltd., UK) for 4 h at 25° C. After crosslinking, the scaffolds were washed thoroughly in distilled water (5 min×5 times), refrozen and re-lyophilized at the same freeze-drying cycle as specified above.

Preparation of matrix-coated plates: Three different types of solutions were prepared for coating culture plates. For collagen-coated plates, a solution of collagen 1 (8-10 mg/mL, BD™) was diluted in distilled water (4:1 dilution ratio). For HA coated plates, a suspension of HA (1% weight) was prepared from the low molecular weight sodium hyaluronate (10-20 kDa, Lifecore Biomedical) in distilled water. For Col 1/HA coated plates, the above solutions of collagen 1 and HA were mixed in the 4:1 ratio of Col 1: HA. 2 mL of each of the three above solutions were added into each well of a 6-well plate, and left for 1 hour at room temperature in a sterile hood. The remaining unattached solutions were carefully aspirated. Each well was plated with $0.3\times10^6$ SK-N-MC cells.

Culture of cells in aggregates and in 3D scaffolds. Ewing's sarcoma cell line SK-N-MC (HTB-IO) was purchased from the American Type Culture Collection (ATCC) and cultured according to the manufacturer's specifications, in ATCC-formulated Eagle's Minimum Essential Medium (EMEM) supplemented with 10% (v/v) Hyclone FBS and 1% penicillin/streptomycin. To form tumor cell aggregates, $0.3\times10^6$ SK-N-MC cells were centrifuged in 15 mL Falcon tubes, 5 minutes at 1200 rpm, with 4 mL of medium and cultured for 7 days at 37° C. in a humidified incubator at 5% $CO_2$.

To seed 3D Collagen 1-HA scaffolds, single-cell suspension of SK-N-MC cells was adjusted to the cell concentration of $1\times10^6$ cells/mL in a 50 ml Falcon tube. A total of 15 scaffolds were added to 30 mL of cell suspension, and the Falcon was set onto a rotary platform for 3 hours at 37° C./5% $CO_2$. Cell seeded scaffolds were then transferred to non-treated wells in 12-multiwell plates (Nunc) and cultured in 2 mL of medium at 37° C./5% $CO_2$. Cell numbers and were determined by Quant-iT PicoGreen dsDNA Assay Kit (Life technologies) according to the manufacturer's instructions.

Mechanical testing: The mechanical properties of native Ewing's sarcoma tumors collected from the patients at the Memorial Sloan-Kettering Cancer Centre (New York, USA) were measured using a previously established protocol. Briefly, the Young's modulus was determined under unconfined compression in phosphate-buffered saline (PBS) at room temperature. An initial tare load of 0.2 N was applied, and followed by a series of stress-relaxation steps, where specimens were compressed at a ramp velocity of 1% per second up to the 10% strain, and maintained at each position for 1,800 s. The Young's modulus was calculated from the equilibrium force measured at the 10% strain.

Scanning Electron Microscopy (SEM): The morphology of the bioengineered tumors was examined by SEM. Samples were washed twice in PBS and fixed in 4% paraformaldheyde in PBS (Santa Cruz, US) for 1 hour. Fixed specimens underwent a graded dehydration series of ethanol (70, 85, 95, 100% for 5 min each) and hexamethyldisilazane drying for 15 min (HMDS, Sigma). Samples were dried overnight in the fume hood, sputter-coated with gold and palladium, and imaged using SEM (Hitachi S-4700).

Fluid uptake by the Scaffolds: Dried samples were weighed (Wd) and immersed in distilled water at 37° C. for different periods of time (2 hours, 3, 7 and 10 days). At each time point, specimens were removed from distilled water and the ability of the scaffold structure to absorb water was measured using a previously described method. At each time point, the samples were removed from water and weighed (Ww). The water uptake was calculated as: Fluid uptake (%)=(Ww−Wd)/Wd×100. Each sample was measured in triplicate.

Scaffold degradation: Dried samples were weighed (Wd) and immersed in distilled water at 37° C. in a humid atmosphere for timed intervals (2 hours, 3, 7 and 10 days). At each time point, specimens were removed from distilled water, air-dried for 24 hand weighed (Wa). The weight loss was calculated as: Weight loss (%)=(Wd−Wa)/Wd×100. Each sample was measured in triplicate.

Histology and immunohistochemistry (IHC): Frozen sections of the native Ewing's sarcoma tumors and bioengineered tumors were fixed in pre-cooled acetone (−20° C.) for 10 minutes. Sections were washed with PBS and treated with 0.3% $H_2O_2$ solution in PBS at room temperature for 10 min to block endogenous peroxidase activity, and incubated with a blocking buffer from Vectastain Elite ABC Kit (Vector Labs), according to the manufacturer's instructions. Then, sections were stained for CD99 (dilution 1:500; Signet antibodies, SIG~3620) and Collagen 1 (dilution 1:500; Abcam, ab34710). Slides were counterstained with Hematoxylin QS (Vector Labs). For the hyaluronan acid binding protein (HABP) staining, the sections were blocked using 1% BSA in HBSS at room temperature for 30 min, and incubated with a biotinylated HABP antibody (dilution 1:100; Millipore #385911). A Streptavidin Alexa fluor 488 conjugate (dilution 1:500; Molecular Probes) was used as the secondary antibody.

Live-Dead assay: At timed intervals (day 3 and day 7), Bioengineered tumor models were incubated in EMEM medium containing 2 μM Calcein and 4 μM of ethidium homodimer-I for 30 min at 37° C., 5% $CO_2$, as indicated by the manufacturer's protocol (UVEIDEAD® Viability/Cytotoxicity Kit, Molecular Probes). Samples were imaged with a fluorescence microscope (Olympus IX81 light microscope, Center Valley Pa.).

Exosome isolation and size analysis: Cells cultured in monolayers, aggregates and 3D scaffolds were washed with PBS twice and cultured in EMEM supplemented with 10% (v/v) Exosome-depleted FBS (SBI) and 1% penicillin/streptomycin for 12 h. The supernatants were collected and exosomes were isolated from cell culture media using the total exosome isolation kit (Invitrogen), according to the manufacturer's protocol. Exosomes from plasma samples were also isolated using the total exosome isolation kit (Invitrogen). The size distributions of exosomes were determined by Nanoparticle Tracking Analysis (NTA) using the Nanosight machine.

Genomics Analysis: Overexpression of EZH2 in Ewing's sarcoma tumors at mRNA levels were compared using the R2 Genomics Analysis and Visualization Platform (http://r2.amc.nl.) The R2 platform is an online genomics analysis tool that can analyze a large collection of public data. We selected EZH2 as gene of interest to generate a MegaSampler using the following dataset:

Tumor Ewing Sarcoma-Francesconi (37 samples). Source: GEO 10: gse34620 Dataset Date: 2000-01-01. Pubmed link: 22327514. A genome-wide association study of at least 401 French ES patients compared to either 684 French or 3668 US self-described Caucasian controls consistently revealed candidate loci at chromosomes 1 and 10 (p<10-6).

Tumor Ewing Sarcoma-Delattre (117 samples). Source: GEO 10: gse 12102 Dataset Date: 2008-06-15. Pubmed link: 22327514. Available tracks in R2: group (CAT) [ews metastasis tumor (metastasis) ews primary tumor (no evidence of disease) ews primary tumor (relapse)].

Healthy: Normal Various —Roth— (353 samples). Source: GEO 10: GSE3526 Dataset Date: 2006-03-30. Pubmed link: 16572319. Normal human tissue samples from ten post-mortem donors were processed to generate total RNA, which was subsequently analyzed for gene expression using Affymetrix U133 plus 2.0 arrays. Donor information: Donor 1-25 year old male; Donor 2-38 year old male; Donor 3-39 year old female; Donor 4-30 year old male; Donor 5-35 year old male; Donor 6-52 year old male; Donor 7-50 year old female; Donor 8-48 year old female; Donor 9-53 year old female; Donor 10-23 year old female.

RNA quality: Total RNA quality and size distribution from cells and exosomes were determined by electropherograms from the Bioanalyzer 2100 using the RNA Pico Chip kit (Agilent Technologies).

Western blot: Cells were lysed in R1PA buffer containing protease inhibitors (Sigma-Aldrich, P8340) and exosomes extracts were obtained using the total Exosome RNA & Protein Isolation Kit (ThermoFisher Scientific) following the manufacturer's instructions. Cell preparations were centrifugated at 12,000 g for 10 min and supernatants containing soluble proteins were collected for analysis. 20 µg of cells and exosomes extracts were loaded on 4-12% gradient Bis-Tris gels (BioRad), transferred to a nitrocellulose membrane and incubated with antibodies against EZH2 (1:500; Millipore 07-689), Calnexin (1:500; Santa Cruz, sc-11397, CD8) (1:500; Santa Cruz, sc-7637) at 4 degrees overnight and GAPDH (1:5000; Invitrogen 437000) at room temperature for one hour.

For detection, membranes were incubated with a secondary antibody anti-rabbit or anti-mouse conjugated with Alexa Fluor 680 dye (1:5000; ThermoFisher Scientific) at room temperature for one hour and imaged on Licor Odyssey scanner.

Exosome-mediated transfer of RNA: SKNMC cells were cultured on Col 1-HA scaffolds for 7 days in ATCC-formulated Eagle's Minimum Essential Medium (EMEM) supplemented with 10% (v/v) Hyclone FBS and 1% penicillin/streptomycin. For exosome isolation, cells were cultured with 10% Exosome-depleted FBS (SBI) and 1% penicillin/streptomycin for 12 h. Supernatants were harvested and exosomes were isolated. To measure protein concentration (by Bradford assay), the concentration of protein was adjusted to about 0.1 µg/µL in PBS, and the samples were diluted 1:50 (20 µl in 1 ml of PBS) for NTA analysis. The same volumes, dilutions and the same camera shutter were used to obtain similar concentrations of particles for measuring size distributions in cell monolayer and TE-Tumors. 10 µg of exosomes protein were labeled with SYTO RNA Select green fluorescent (Invitrogen) during 30 min at 37° C./5% $CO_2$ at a final dye concentration of 10 µM. Exosome Spin Columns (MW 3000) were used to remove unincorporated dye from exosome labeling. The same volume of PBS without exosomes was also treated with SYTO RNA and exosome spin columns to serve as a control. Cells (5,000 cells/well) were seeded in an 8-well chamber slide the day before the exosome-mediated transferring assay. 10 µg of labeled exosomes in PBS, or same volume of PBS control, were incubated with hMSC passage 3, human osteoblasts or human osteoclasts during 2 h at 37° C./5% $CO_2$. Cells were fixed for 20 minutes with 4% PFA in PBS and mounting with Vectashield-DAPI.

Figure 7A:
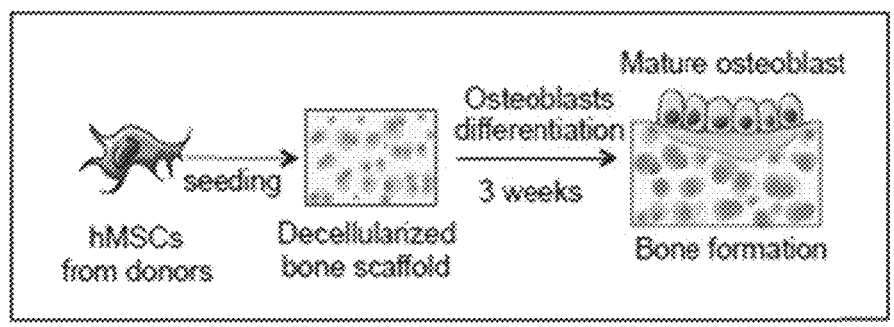
FIGS. 7A-C illustrates differentiation of human mesenchymal stem cells to osteoblasts in scaffold according to embodiments of the present disclosure.
Figure 7B:
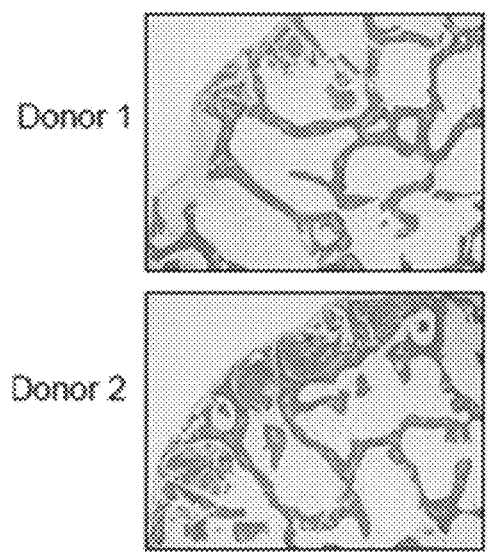
Figure 7C:
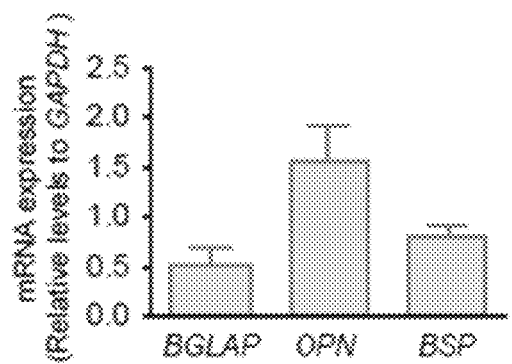
Figure 8A:
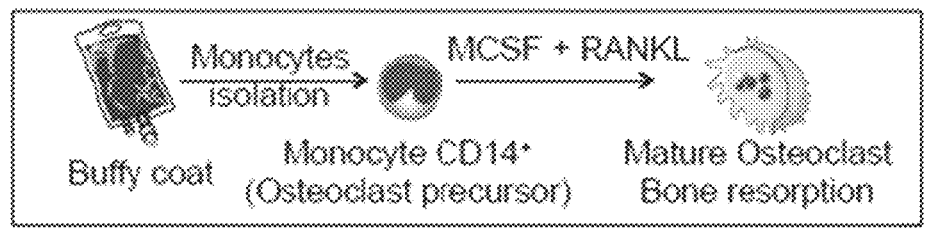
FIGS. 8A-F illustrates differentiation of human monocytes to osteoclasts in monolayer according to embodiments of the present disclosure.

Derivation of bone cell precursors: According to the embodiment for derivation of bone precursor human mesenchymal stem cells (hMSC) were used to differentiate into osteoblasts, hMSCs from various sources have been used to engineer bone. The decellularized bone scaffold preserved not only the structural and mechanical features of the original bone, but also maintained its inorganic mineral phase and many of the growth factors. Notably, owing to the highly osteogenic properties of these scaffolds, the supplementation of BMP-2 during bone tissue engineering is not necessary.

hMSC are used as a source of osteoblasts for engineering bone in vitro. The ability of hMSC (from two different donors) to differentiate into osteoblasts, both in cell monolayers and in decellularized bone scaffolds, was confirmed (as shown in FIGS. 7A and 8A). hMSC from both donors were positive for Alkaline phosphatase and Von Kossa after 3 weeks of differentiation in monolayer culture (as shown in FIG. 7B). Increased expression of bone markers (BGLAP, OPN and BSP) was observed by qRT-PCR, relatively to the hMSC cultured in expansion medium (FIG. 7C). Then bone containing only osteoblasts (TE-hOB) was engineered, by culturing hMSC in decellularized bone scaffolds using osteogenic medium, for 3 weeks (FIG. 8A). The ability to generate hMSC-derived osteoblasts and form new bone matrix (by histology, FIG. 8B) and expression of bone markers (by qRT-PCR, FIG. 8C) was confirmed.

The capability of osteoclast precursors (CD14+ monocytes) to differentiate into mature osteoclasts (as shown in FIG. 8A) was assessed and identified based on their unique morphology and function. Osteoclasts are large, multinucleated and polarized cells with the nuclei localized toward the apical membrane and a ruffled border membrane. These cells are specialized in bone resorption that proceeds with degradation of organic matrix and demineralization of the mineral matrix in specific regions known as "resorption lacunae", and inducing increases in local concentrations of calcium and phosphate. Activated osteoclasts resorb bone by lowering the pH in the resorption lacunae, following secretion of acidic hydrolases such as cathepsin K and the tartrate-resistant acid phosphatase (TRAP), and express considerable levels of calcitonin receptor.

Figure 8B:
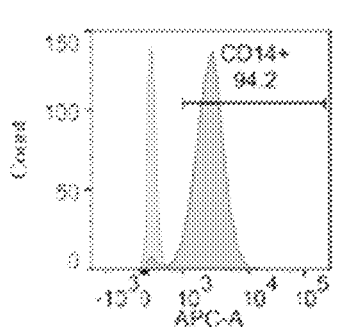
Figure 8D:
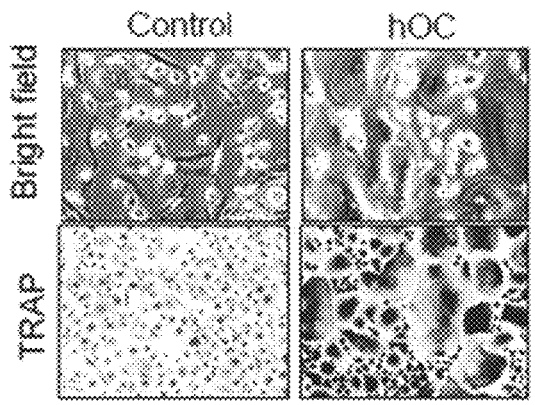
Figure 8C:
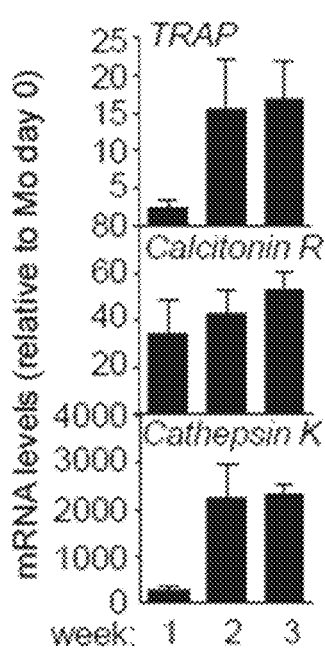
Figure 8E:
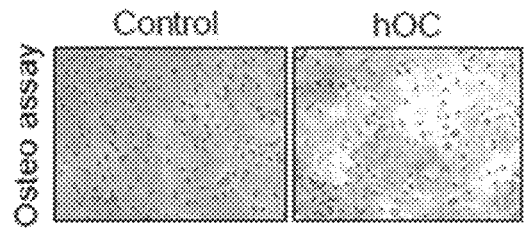
Figure 8F:
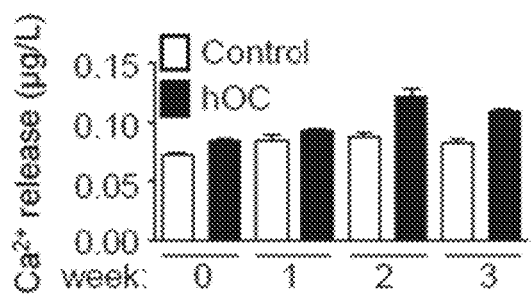
Figure 9A:
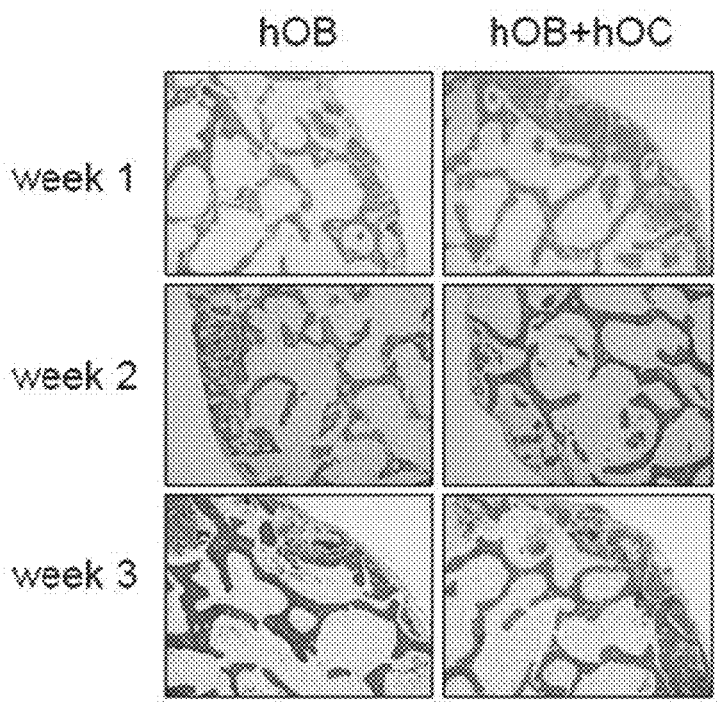
FIGS. 9A-C illustrates differentiation of human monocytes to osteoclasts in co-culture with human osteoblasts in bone scaffold according to embodiments of the present disclosure.
Figure 9B:
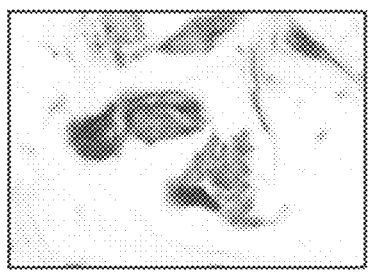
Figure 9C:
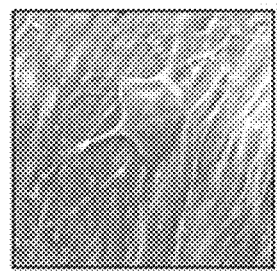

Osteoclasts were derived from human monocytes isolated from buffy coats, and tested for purity. On average, the enrichment of CD14+ monocytes was 94%, as determined by flow cytometry analysis (as shown in FIG. 8B). The purified monocytes were cultured for up to 3 weeks in monolayer in the presence of RANKL to induce osteoclastic lineage differentiation. By week 1, the osteoclasts markers TRAP, calcitonin receptor and cathepsin K were expressed (FIG. 8C), and this expression reached the maximum level at week 3. Morphology, differentiation and multi-nuclearity of osteoclasts by TRAP staining was evaluated (FIG. 8D). Osteoclast activation and functionality were evaluated (as shown in FIG. 8E), and the calcium release over time was compared to the undifferentiated cell control (as shown in FIG. 8F).

Figure 10B:
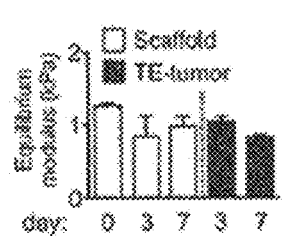
Figure 10C:
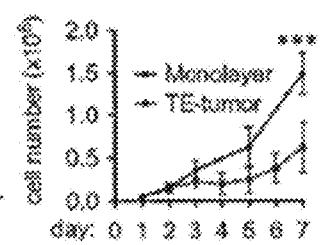

Bioengineered tumor model: Native Ewing's sarcoma (ES) is a pediatric tumor rich in collagen 1 (col 1) and hyaluronic acid (HA) proteins (as shown in FIG. 10A), and soft tissue matrix characterized by an equilibrium modulus of ~2 kPa (as shown in FIG. 10B). In order to mimic the composition and mechanical properties of the ES extracellular matrix, we used purified preparations of natural col 1 and HA (low molecular weight, LMW; high molecular weight, HMW) with a stiffness matching that of the native tumor (as shown in FIG. 10B). Two types of 3D porous scaffolds (Col1-HA LMW; Col1-HA HMW) were made by freeze-drying of Col 1/HA solutions, and cross-linking with 1-ethyl-3-(3-dimethylaminopropyl)-carbodiimide hydrochloride, EDC, in the presence of N-hydroxysuccinimide, NHS (as shown in FIG. 10C).

Figure 10D:
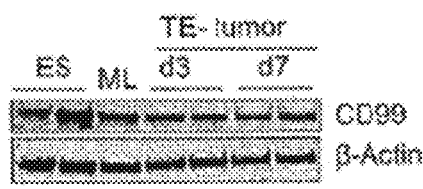

The swelling behavior, measured by the liquid uptake, was similar for the two porous scaffolds, and in agreement with the previous studies. The rate of degradation was much slower for Col 1-Ha LMW than Col 1-Ha HMW scaffolds, presumably due to the higher density of chemical cross-links (as shown in FIG. 10D). These results demonstrated that the Col 1-Ha LMW scaffold was suitable for supporting the in vitro culture of tumor cells. In previous studies, LMW HA was shown to play a role in tumor progression in a number of cancers. Therefore, we selected the Col 1-Ha LMW scaffold as an appropriate biomimetic environment for culturing ES cells.

To bioengineer the most common ES tumor type, SK-N-MC cell lines (type 1 rearrangement) were cultured in Col 1-Ha LMW scaffolds. Mechanical properties of the TE-tumor did not change over time (as shown in FIG. 10B), and the model was stable over one week of culture. The proliferation of ES cells cultured within the TE-tumor model was slower than when the same cells were cultured in monolayer (as shown in FIG. 10C), consistent with the known lower rates of cell proliferation in native tumors compared to cancer cells cultured in monolayers. Live-dead analysis demonstrated uniform distribution of cells throughout the scaffolds at day 3 and day 7, and showed that most of the cells were viable after 7 days of culture (as shown in FIG. 11).

Figure 10E:
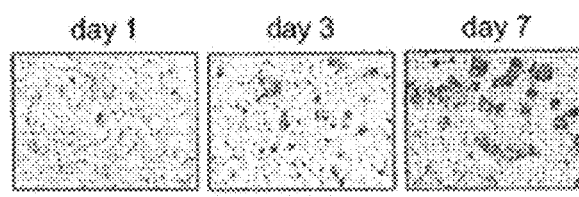
Figure 10F:

Notably, the levels of expression of CD99 in the TE tumor model were comparable to those measured in the samples of patients' tumors (as shown in FIG. 10D). These data show that cell culture on Col 1/HA scaffolds does not modify the levels of this important membrane protein that is highly expressed in most cases of Ewing's sarcoma and maintains them at levels similar to those in tumors from patients. The cells cultured in the TE-tumor model formed small avascular aggregates that increased in size over time, mimicking the initiation of native tumor formation (as shown in FIGS. 10E-F).

Figure 13A:
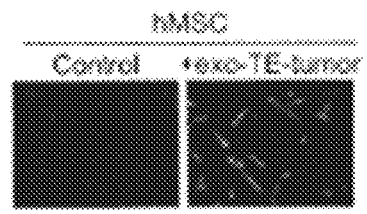
FIGS. 13A-F illustrates exosome-mediated transfer of EZH2 mRNA.

Evaluation of the purity of exosomes preparations: In order to check the purity of the exosome preparations, we performed two sets of analysis consisting in protein composition and total RNA profiles. Toward this end, first we analyzed the levels of the CD81 (exosomal marker) and calnexin (only detectable in cellular and apoptotic bodies extracts), in monolayer and the TE tumor model at day 3 and day 7 (as shown in FIG. 13A). GAPDH levels were determined to address the possibility of using GAPDH as a loading control of the technique. Absence of calnexin was confirmed in the extracellular preparations. This suggests that there is no cellular or apoptotic bodies' contamination in the exosomes preparations. CD81 was detectable in exosomes preparations from cells in monolayer but not from TE-tumors preparations. GAPDH levels were similar between samples that points GAPDH as a good loading control.

Figure 12A:
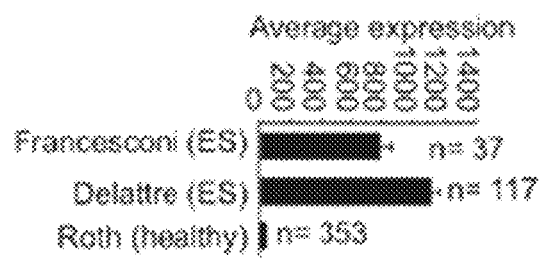
FIGS. 12A-E illustrates effects of engineered microenvironment on exosome cargo.
Figure 12B:
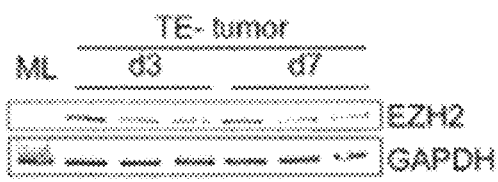

Then, the quality of the exosomes isolation was analyzed by analyzing RNA profiles from cells and exosomes preparations from cells in monolayer and TE-tumor at day 7, using the Bioanalyzer 2100 (as shown in FIG. 12B). As expected, electropherograms showed different RNA size distributions between samples. The RNA profile from cells revealed two dominant peaks, corresponding to the ribosomal RNA (rRNA) subunits 18S and 28S. Both peaks are also observed in RNA profiles from preparations of apoptotic bodies. The RNA profile from extracellular vesicles lacked both rRNA peaks and showed and enrichment in small RNAs, accordingly with the literature.

Figure 11A:
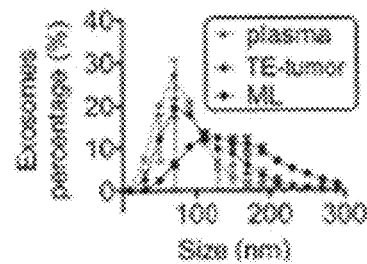
FIGS. 11A-F illustrates recapitulation of exosomes' size in the bioengineered tumors.

Exosome size: Using the Nanoparticle Tracking Analysis (NTA), the size distributions of exosomes released into the culture media from the bioengineered tumor and from cell monolayers, were determined and compared to the size distributions of exosomes secreted into the blood plasma of ES patients. The sizes of exosomes isolated from human plasma (average mean±SD: 88.7±22 nm; average mode±SD: 70.0±20 nm, n=7 patients, as shown in FIG. 11A) were consistent with the previously reported data, and significantly smaller than the exosomes from monolayer cultures of ES cells (average mean±SD: 149.2±19 nm; average mode±SD=103.3±23 nm, n=3,**p<0.01; as shown in FIG. 11A). In addition, the numbers of particles per unit protein were not statistically different for cell monolayers and tissue engineered tumors (as shown in FIG. 13). Notably, the sizes of exosomes released from tumor models (average mean±SD: 113.4±10 nm, average mode±SD: 76.7, ±10.3 n=6; as shown in FIG. 11A) were indistinguishable from those in the patients' plasma. These data suggest that the 3-dimensionality or composition of the scaffold (or both of these factors) regulate the exosomes to reach their native size. To distinguish the relative contributions of the matrix 3-dimensionality and composition, we investigated the sizes of exosomes in multiple model systems.

Figure 11B:
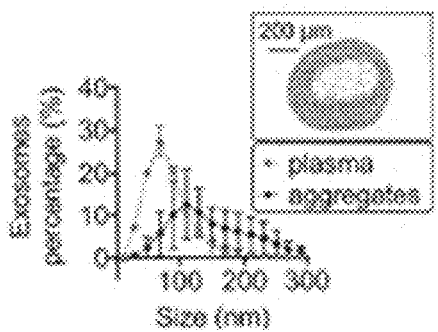
Figure 11C:
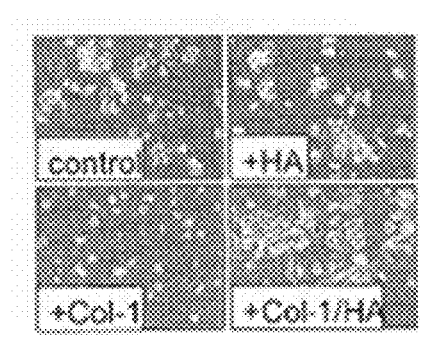
Figure 11E:
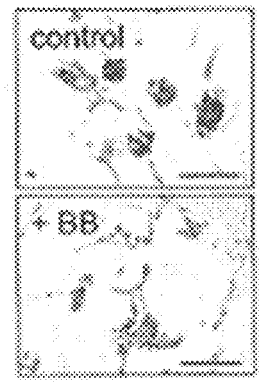
Figure 11D:
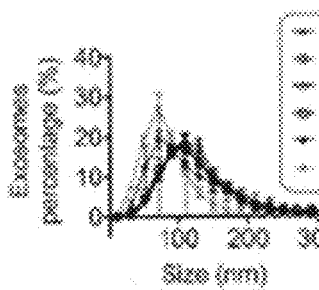

To evaluate the role of 3-dimensionality, we generated ES cell aggregates in a generic polypropylene context, in the range of sizes that we have observed for bioengineered tumors at day 7 (as shown in FIG. 11B). Neither the average mean nor the mode size of exosomes isolated from these aggregates recapitulated the values found in the patients' plasma (as shown in FIG. 11B). Mimicking the tumor size and morphology using 3D models without a biomimetic context was thus not sufficient to recapitulate the native exosome size. To evaluate the role of matrix composition, we cultured ES cells in monolayers formed on polystyrene dishes coated with different extracellular matrix proteins (HA LMW, Col 1, Col 1-HA LMW, as shown in FIG. 11C). It was observed that there was no difference in the mean size or mode of exosomes secreted by the ES cells cultured on uncoated polystyrene dishes and on dishes coated with the proteins used for fabricating the scaffolds (as shown in FIG. 11D). These results indicate that mimicking the native matrix composition without providing the native stiffness and 3D context was also not sufficient for reproducing the native size of exosomes. Providing both the 3-dimensionality of cell culture and the composition or extracellular matrix found in ES was necessary for recapitulating the exosome size.

Figure 11F:
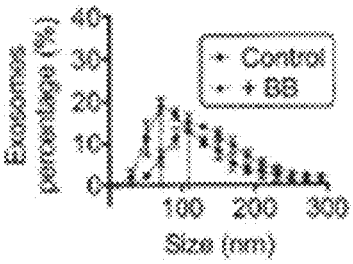

To probe a possible mechanism underlying the observed effects of the tumor environment on exosome size, we modified the tension forces within the cells. To this end, we maintained the 3-dimensionality, composition and stiffness of the microenvironment at levels comparable to the native tumor matrix, while eliminating tension-dependent changes in cell shape by using Blebbistatin, a well-known selective inhibitor of non-muscle myosin n. Cell morphology in blebbistatin-treated samples was different from untreated controls (as shown in FIG. 11E), with a partial disassembly of cell aggregates (as shown in FIG. 11E) and a shift of the exosome size distribution curve to higher values (as shown in FIG. 11F) when tensional forces within the cells were modified in a 3D setting.

Figures 12C, 12D:
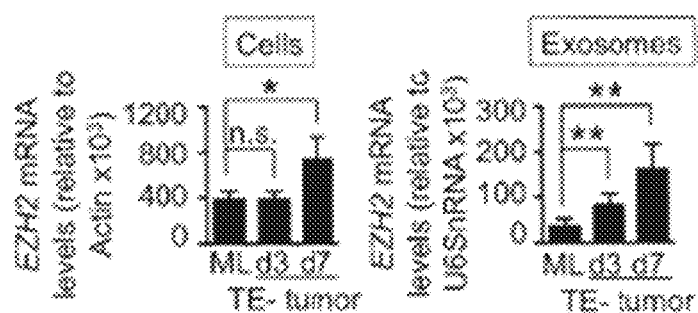
Figure 12E:
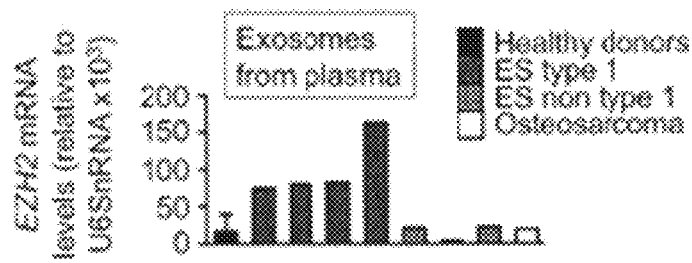

Exosome cargo: Based on these findings, it was hypothesized that the exosome size is not the only property controlled by the microenvironment, and that their cargo is also a subject to regulation. To test this hypothesis, we analyzed the exosomal mRNA cargo and focused on EZH2, one of the most important mediators of Ewing's sarcoma tumor growth and progression. First, it was confirmed that over expression of EZH2 in ES tumors at mRNA levels using the R2 Genomics Analysis and Visualization Platform (http://r2.amc.nl), by comparing the gene profiles for ES tumors (arrays from Francesconi n=37, and Delattre; n=117) and healthy tissues (array from Roth n=353) (as shown in FIG. 12A). EZH2 overexpression in ES tumors by Immunohistochemistry was checked and EZH2 protein was almost undetectable by Western blot in ES cells cultured in monolayers (as shown in FIG. 12B), which also expressed low levels of EZH2 mRNA by qRT-PCR (as shown in FIG. 12C). However, EZH2 mRNA and EZH2 protein increased in TE-tumors, both at the protein level (as shown in FIG. 12B) and at the mRNA level (as shown in FIG. 12C). These data supported the notion that a native-like environment can modulate cancer biology and mimic, at least in part, the properties of real tumors. Exosomes released from the ES cells cultured in monolayers and bioengineered tumors were isolated and high levels of EZH2 mRNA in exosomes from TE-tumors, both at day 3 and day 7 was found, when compared to monolayers (as shown in FIG. 12D). Importantly, the measured levels of EZH2 in bioengineered tumors corresponded to those in the blood plasma of ES patients. EZH2 mRNA was detected in exosomes from Ewing's sarcoma type-I plasma (n=4), but not in plasma of healthy donors (n=4), non-type 1 patients (n=3) or an osteosarcoma patient (n=1) (as shown in FIG. 12E).

Figure 13B:
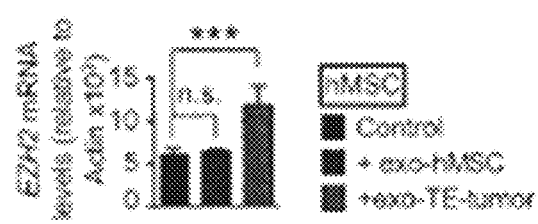
Figure 13C:
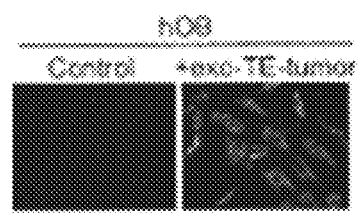
Figure 13D:
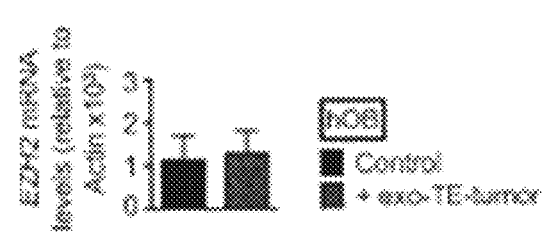
Figure 13E:
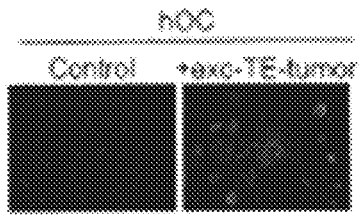
Figure 13F:
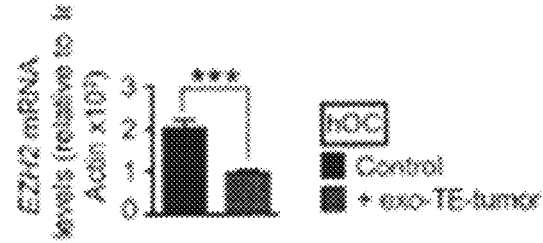

Transfer of exosome cargo: Because EZH2 induces an aberrant phenotype of Ewing's sarcoma in vivo and also affects the hMSCs cultured in vitro, Exosomes containing EZH2 mRNA can transfer their cargo to the cells hMSCs normally present in the bone niche were investigated. Labeled exosomes derived from the TE-tumor (Exo-TE-tumor) with the green RNA-selective nucleic acid stain SYTO RNA Select at day 7, the time point at which we observed high levels of EZH2 mRNA in these exosomes. The exosomes from the TE-tumors were taken up by bone marrow derived hMSCs, after 12 hours of incubation compared to the technical control (PBS treated with SYTO RNASelect) (as shown in FIG. 13A). Significant increases in EZH2 mRNA levels were detected in hMSC treated with exosomes from TE-tumors, when compared with untreated hMSCs or hMSCs treated with hMSC-derived exosomes (as shown in FIG. 13B). Finally, we analyzed the effects of exosomes secreted by bioengineered tumors on human osteoblasts (hOB) and human osteoclasts (hOC). Labeled exosomes from TE-tumors were taken up by both hOB (4C) and hOC (as shown in FIG. 13E). However, this uptake had no effect on EZH2 mRNA levels in hOB (as shown in FIG. 13D), and resulted in down-regulation of EZH2 in hOC (as shown in FIG. 13F). These data confirm that EZH2 mRNA-loaded exosomes can be transferred in vitro from cancer cells to cell populations from the bone niche, with different effects on hMSC (upregulation of EZH2), hOC (downregulation of EZH2) and hOB.

EXAMPLES

Native Tumors

Ewing's sarcoma tumors were obtained from a Tissue Bank. The samples were fully de-identified. Three different frozen tissue samples were cut in sets of 6 contiguous 10 µm-thick sections and homogenized in Trizol (Life technologies) for RNA extraction and subsequent gene expression analysis.

Cell Culture

All cells were cultured at 37° C. in a humidified incubator at 5% $CO_2$, unless noted otherwise.

Cancer cell lines: Ewing's sarcoma cell lines SK-N-MC (HTB-10) and RD-ES (HTB-166) were purchased from the American Type Culture Collection (ATCC) and cultured according to the manufacturer's specifications. RD-ES cells were cultured in ATCC282 formulated RPMI-1640 Medium (RPMI) and SK-N-MC cells were cultured in ATCC283 formulated Eagle's Minimum Essential Medium (EMEM). Both media were supplemented with 10% (v/v) Hyclone FBS and 1% penicillin/streptomycin. Cells were cultured at 37° C. in a humidified incubator at 5% $CO_2$.

U2OS osteosarcoma cell line and HEK293T cell line were provided and cultured in Dulbecco's Modified Eagle Medium (DMEM) supplemented with 10% (v/v) Hyclone FBS and 1% penicillin/streptomycin).

Tumor aggregates: Tumor aggregates were prepared by using aliquots of 300,000 Ewing's sarcoma cells, which were centrifuged in 15 ml Falcon tubes (5 minutes at 12,000 rpm), and cultured in 4 mL of osteoclast differentiation medium without cytokines: Minimum Essential Medium Eagle Alpha modification, consisting of α-MEM (Sigma, M4526) supplemented with 10% (v/v) heat inactivated Hyclone FBS, 1% penicillin/streptomycin and L-Glutamine (Gibco #25030-081) for 1 week.

The cultivation, seeding and osteogenic differentiation of Human Mesenchymal Stem Cells (hMSC) were performed. Briefly, hMSC were cultured in basic medium (DMEM supplemented with 10% (v/v) Hyclone FBS and 1% penicillin/streptomycin) for maintenance and expansion, followed by osteogenic medium (basic medium supplemented with 1 µM dexamethasone, 10 mM β-glycerophosphate, 50 .mu.M ascorbic acid-2-phosphate) for osteogenic differentiation. Due to the highly osteogenic properties of the mineralized bone scaffolds used to culture the cells, the supplementation of MBP-2 was not necessary.

Retroviral and Lentiviral Transductions: Retroviral transductions were performed using a GFP retroviral vector (pBabe-Puro-GFP). Lentiviral transductions were performed. EWS-FLI-GFP expression vector was provided.

Tumor Cell Spheroids: To form tumor cell spheroids, $0.3 \times 10^6$ Ewing's sarcoma cells were centrifuged in 15 mL Falcon tubes, 5 minutes at 1200 rpm, with 4 mL of medium and cultured for one week at 37° C. in a humidified incubator at 5% $CO_2$.

Tissue engineered model of tumor cell culture scaffolds (4 mm diameter×4 mm high plugs) were prepared from fully decellularized bone. The scaffolds were seeded with $1.5 \times 10^6$ hMSCs (passage 3) and cultured in 6 mL of osteogenic medium for 4 weeks. Medium was changed biweekly. After 4 weeks, the scaffolds were bisected; one half was seeded with Ewing's sarcoma cells (3 spheroids per scaffold) (TE-ES) and the other half was used as a control (TE-bone).

Three tumor models were formed using the three tumor cell lines. For each tumor, TE bone was used as a control. TE-RD model (and their counterpart TE-bone controls) were cultured in RPMI medium. TE-SK-N-MC model (and their counterpart TE-bone controls) were cultured in EMEM. TE-EWS-GFP model (and their counterpart TE-bone controls) were cultured in DMEM.

All culture media were supplemented with 10% (v/v) Hyclone FBS and 1% penicillin/streptomycin. TE-ES and TE-bone models were cultured at 37° C. in a humidified incubator at 5% $CO_2$ for 2 and 4 weeks.

Cytometry: Surface markers analysis by FACS was carried out. hMSC and ES cell lines (RD-ES, SK-N-MC and EWS-GFP) were harvested, centrifugated and incubated at 4° C. for 1 hour with fluorochrome conjugated antibodies APC Mouse anti-human CD13 (BD Pharmingen, 557454), APC Mouse anti-human CD44 (BD Pharmingen, 560532), APC Mouse anti-human CD73 (BD Pharmingen, 560847), database (http://pga.mgh.harvard.edu/primerbankL). GFP primers were selected. Other qRT-PCR primer sequences were obtained from the PrimerBank data base (http://pga.mgh.harvard.edu/primerbank/):

TABLE 1

| Gene Description | PrimerBank ID |
| --- | --- |
| beta actin (Actin) | 4501885a1 |
| EWS-FLI1 fusion isoform type 8 (EWS-FLI) | 633772a1 |
| Homo sapiens calcitonin receptor (CALCR) | 260064026c1 |
| Homo sapiens acid phosphatase 5, tartrate resistant (TRAP) | 161377452c1 |
| Homo sapiens secreted phosphoprotein 1 (OPN) | 38146097b1 |
| Homo sapiens integrin-binding sialoprotein (BSP) | 167466186b1 |
| Homo sapiens NK2 homeobox 2 (NKX2-2) | 32307133b1 |
| Homo sapiens tumor protein p53 (TP53) | 371502118c1 |
| ACTN4 Homo sapiens actinin, a 4 (ACTN4) | 316660986c2 |
| CCND2 Homo sapiens cyclin D2 (CCND2) | 209969683c1 |
| COL1A2 Homo sapiens collagen, type I, α2 (COL1A2) | 48762933c3 |
| COL3A1 Homo sapiens collagen, type III, α1 (COL3A1) | 110224482c2 |
| Homo sapiens collagen, type VI, a1 (COL6A1) | 87196338c2 |
| COL6A2 Homo sapiens collagen, type VI, α2 (COL6A2) | 115527065c1 |
| COL6A3 Homo sapiens collagen, type VI, α3 (COL6A3) | 240255534c1 |
| FLNB Homo sapiens filamin B, β (FLNB) | 256222414c2 |
| MYLK Homo sapiens myosin light chain kinase (MYLK) | 116008189c1 |
| Homo sapiens 3-phosphoinositide dependent protein kinase-1 (PDPK1) | 60498971c1 |
| Homo sapiens protein phosphatase 1, regulatory subunit 12A (PPP1R12A) | 219842213c1 |
| Homo sapiens insulin-like growth factor 1 (somatomedin C) (IGF1) | 163659898c1 |
| VCL Homo sapiens vinculin (VCL) | 50593538c1 |
| CDKN1B Homo sapiens cyclin-dependent kinase inhibitor 1B (p27, Kip1) (CDKN1B) | 207113192c3 |
| Homo sapiens C-terminal binding protein 1 (CTBP1) | 61743966c2 |
| CTBP2 Homo sapiens C-terminal binding protein 2 (CTBP2) | 145580576c1 |
| ETS1 Homo sapiens v-ets erythroblastosis virus E26 oncogene homolog 1 (avian) (ETS1) | 219689117c1 |
| c-K-ras2 protein isoform a (KRAS) | 15718763a1 |
| PIAS1 Homo sapiens protein inhibitor of activated STAT, 1 (PIAS1) | 7706636c2 |
| Homo sapiens retinoid X receptor, alpha (RXRA) | 207028087c3 |
| Homo sapiens signal transducer and activator of transcription 3 (STAT3) | 47080104c1 |
| Homo sapiens cell division cycle 42 (GTP binding protein, 25 kDa) (CDC42) | 89903014c1 |
| Homo sapiens collagen, type IV, .alpha.2 (COL4A2) | 116256353c1 |
| Homo sapiens catenin (cadherin-associated protein), β1, 88 kDa (CTNNB1) | 148233337c2 |
| Homo sapiens jun proto-oncogene (JUN) | 44890066c1 |
| laminin a 4 chain (LAMA4) | 4504949a2 |
| Homo sapiens laminin, β1 (LAMB1) | 167614503c1 |
| Homo sapiens laminin, γ1 (formerly LAMB2) (LAMC1) | 145309325c3 |
| Homo sapiens phosphoinositide-3-kinase, regulatory subunit 1 (a) (PIK3R1) | 335057530c3 |
| Homo sapiens phosphatase and tensin homolog (PTEN) | 110224474c2 |
| Homo sapiens hypoxia inducible factor 1, α subunit (HIF1A) | 194473734c1 |
| Homo sapiens vascular endothelial growth factor A (VEGFA) | NM_001101 |
| Homo sapiens EPH receptor A2 (EPHA2) | 296010835c1 |
| Homo sapiens tissue factor pathway inhibitor (TFPI) | 98991770c1 |
| Homo sapiens laminin, γ2 (LAMC2) | 157419139c1 |

APC Mouse anti-human CD90 (BD Pharmingen, 559869) and APC Mouse anti-human CD105 (BD Pharmingen, 562408). Negative control cells were stained with APC mouse IgG1, k isotype control, Clone MOPC-21 (BD Pharmingen, 555751). CD99 expression was assessed incubating cells with CD99 primary antibody (Signet antibodies, SIG-3620). FACS data were analyzed using FlowJo software version 7.6 (Tree Star Inc., Ashland, Oreg., USA). Quantitative Real-Time PCR (qRT-PCR).

Total RNA from cells was obtained using Trizol (Life Technologies) and total RNA from exosomes was obtained using the Total Exosome RNA & Protein Isolation Kit (ThermoFisher scientific) following the manufacturer's instructions. RNA preparations (2 µg) were treated with "Ready-to-go you-prime first-strand beads" (GE Healthcare) to generate cDNA. Quantitative real-time PCR was performed using DNA Master SYBR Green I mix (Applied Biosystems). mRNA expression levels were quantified applying the ΔCt method, Δ Ct=(Ct of gene of interest-Ct of Actin). EZH2 primers were obtained from the PrimerBank Microarray data analysis. Expression of genes in native Ewing's Sarcoma tumors and cell lines was studied in 11 cell lines and 44 tumors by applying the barcode method to the Affymetrix Human Genome U1332 Plus 2 gene expression data. A probeset was considered expressed in cell lines/tumors only if detected in all cell lines/tumors. Where a gene had multiple probesets, the gene was only counted once. Genes expressed in cell lines, but not tumors, or in tumors, but not cell lines, were identified from the asymmetric difference of both sets.

Histology and Immunohistochemistry

Histology and immunohistochemistry: Tumor tissue constructs and all controls were fixed in 10% formalin for 24 h and then decalcified with Immunocal (StatLab Corp., McKinney, Tex.) for 2 days. Samples were dehydrated in graded ethanol washes, and embedded in paraffin. Serial sections (3 µm thick) were prepared for histology and stained with hematoxylin and eosin (H/E).

TE-ES and TE-bone models were fixed in 10% formalin, embedded in paraffin, sectioned at 4 µm and stained with hematoxylin and eosin (H/E). The sections were then stained for CD99 (dilution 1:500; Signet antibodies, SIG-3620) and GLUT1 (dilution 1:500; Abcam, ab652) as previously described, and counterstained with Hematoxylin QS (Vector Labs). For PAS staining, periodic acid-Schiff (PAS) (from Sigma-Aldrich) was used according to the manufacturer's instructions.

hMSC (passage 3) were plated in 24 well plates ($1 \times 10^4$ cells/cm$^2$) and cultured for 3 weeks in either basic medium or osteogenic medium. At weeks 1, 2 and 3 osteogenic differentiation was analyzed by alkaline phosphatase activity (Sigma-Aldrich, St Louis, Mo., USA), following the manufacturer's instructions and by von Kossa staining Sections were incubated with 1% $AgNO_3$ solution in water and exposed to a 60 W light for 1 hour.

Hypoxyprobe™-1 (pimonidazole) Kit for the Detection of Tissue Hypoxia (Chemicon International, Inc., Temecula, Calif., USA) was used to detect hypoxia in TE-bone according to the manufacturer's instructions. Preparations were mounted with vectashield and Nuclei were counterstained with DAPI (Vector Labs, H-1200).

TUNEL assay. Apoptotic cells were detected by an in situ cell death detection kit, TMR red (Roche Applied Science, Mannheim, Germany), according to the manufacturer's instructions. The assay measures DNA fragmentation by immunofluorescence using TUNEL (terminal deoxynucleotidyl transferase-mediated dUTP nick end-labeling) method at the single cell level. One hundred cells per field (n=3) in the center of the TEES model (n=3) were counted to quantify the percentage of apoptotic cells. Nuclei were stained with Hoechst 33342 (Molecular probes).

Enzyme-Linked Immunoabsorbent Assay (ELISA)

24-hour supernatants from TE-ES and TE-bone controls were analyzed to detect angiogenic proteins, using a Proteome Profiler Human Angiogenesis Array Kit (R&D Systems, ARY007) according to the manufacturer's instructions.

Figure 19A:
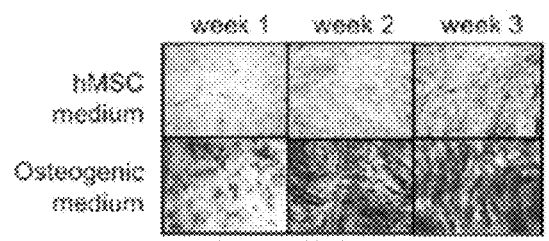
FIGS. 19A-F illustrate generation and characterization of TE-bone according to embodiments of the present disclosure.
Figure 19B:
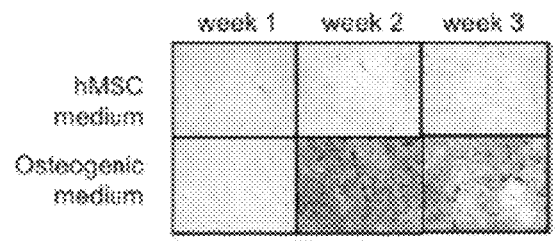
Figure 19C:
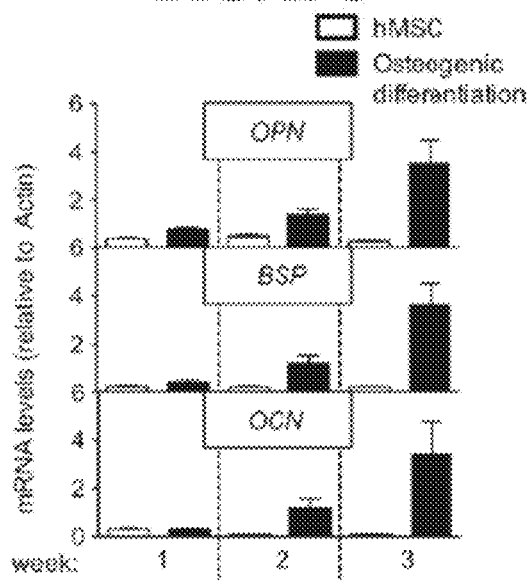
Figure 19D:
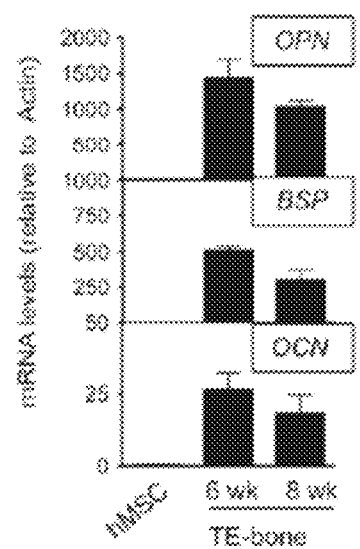
Figure 19E:
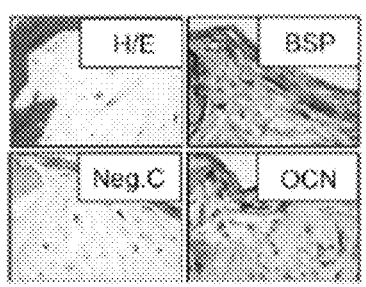
Figure 19F:
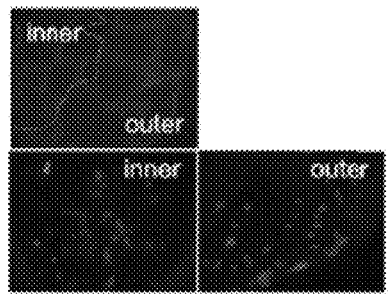

Aspects of the generation and characterization of TE-bone are illustrated in FIGS. 19A-F. In FIG. 19A Osteogenic differentiation evidenced by Alkaline phosphatase staining hMSCs in monolayer were cultured in hMSC medium or osteogenic medium for 3 weeks. Alkaline phosphatase staining was performed at week 1, 2 and 3. Differentiated stem cells positive for alkaline phosphatase were stained blue. Images are representative of n=3 samples per condition. FIG. 19B shows Mineral deposition analysis by the von Kossa method. hMSC were cultured as specified in FIG. 19A. Black stained phosphate deposits demonstrated osteogenic differentiation of hMSC. Images are representative of n=3 samples per condition. FIG. 19C shows qRT-PCR analysis of bone genes during osteogenic differentiation in monolayer. mRNA levels of Osteopontin (OPN), Bone Sialoprotein (BSP), and Osteocalcin (OCN) in hMSC cultured in monolayer in hMSC medium or osteogenic differentiation medium were assessed to demonstrate osteogenic induction and bone differentiation. Data are shown as Average±SD (n=3). FIG. 19D shows qRT-PCR analysis of bone genes during osteogenic differentiation in scaffold. mRNA levels of Osteopontin (OPN), Bone Sialoprotein (BSP), and Osteocalcin (OCN) in hMSC cultured in a bone scaffold for 6 and 8 weeks in osteogenic differentiation medium were assessed and compared to hMSC at t=0. FIG. 19E shows Bone-related protein expression analysis by IHC in TE-bone at week 8. Counterstaining was performed with hematoxylin QS (blue). Representative images are shown (n=3); H/E, Hematoxylin and Eosin. FIG. 19F shows Hypoxia analysis of TE-bone by tissue immunofluorescence of pimonidazole-binding cells (green). Nuclei were stained with DAPI. Representative images are shown (n=3 per condition).

Referring to FIGS. 20A-D, characterization of Ewing's sarcoma cell lines is illustrated. FIG. 20A shows Morphology of the ES cell lines RD-ES and SK-N-MC. Left panel: brightfield images showing typical small round cell morphology. Right panel: GFP expression images by fluorescence microscopy. RD-ES and SK-N-MC were stably transduced with pBabe-GFP retroviral vector as described in supplementary methods. FIG. 20B shows FACS analysis of negative and positive surface markers in Ewing's sarcoma cells. FIG. 20C shows Top panels: brightfield images of hMSC (passage 3) and transduced with EWS-GFP vector at day 30 (without passage) and day 35 (passage 2). Low panels: GFP expression images at day 30 and 35 post-transduction. FIG. 20D shows analysis of hMSC and ES surface markers in EW-GFP cell line. hMSC were CD13, CD44, CD90 and CD105 positive and expressed low levels of the ES-specific CD99 marker. EWS-GFP at day 35 lost hMSC surface proteins, acquiring ES surface markers and expressing high levels of CD99.

Tables 2 and 3 illustrate genes differentially expressed in Ewing's sarcoma tumors and cell lines. Table 2: Number of genes expressed in ESFT and in cell lines. Table 3: Focal adhesion genes and related to pathways in cancer genes expressed in ESFT but not in cell lines.

TABLE 2

| Condition | Number of genes |
| --- | --- |
| Genes expressed in cell-lines | 2977 |
| Genes expressed in tumors | 2430 |
| Genes expressed in cell-lines but not tumors | 1312 |
| Genes expressed in tumors not cell-lines | 599 |

TABLE 3

| | |
| --- | --- |
| Focal adhesion: | ACTN4, CCND2, COL1A2, COL3A1, COL6A1, COL6A2, COL6A3, FLNB, MYLK, PDPK1, PPP1R12A, IGF1, VCL |
| Pathways in cancer: | CDKN1B, CTBP1, CTBP2, ETS1, KRAS, PIAS1, RXRA, STAT3, TP53 |
| Both: | CDC42, COL4A1, COL4A2, CTNNB1, FN1, JUN, LAMA4, LAMB1, LAMBC1, PIK3R1, PTEN |

Figure 21:
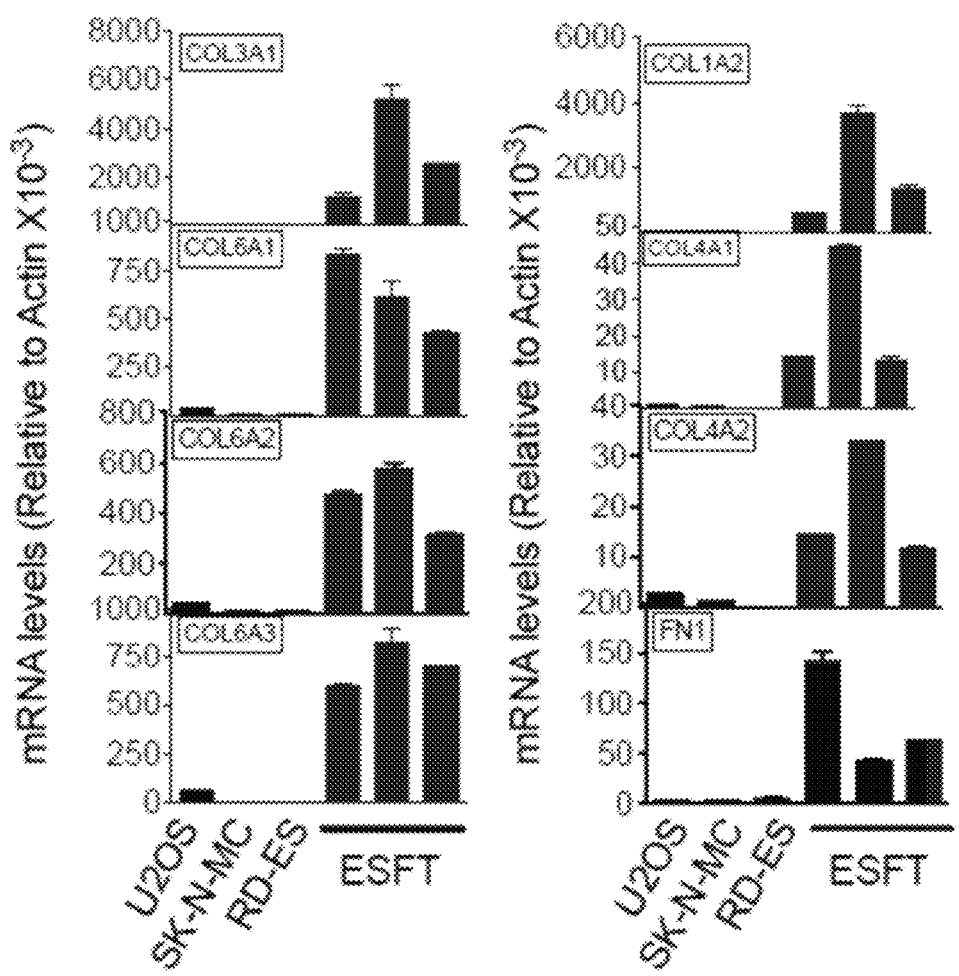
FIG. 21 illustrates focal adhesion genes and cancer genes expressed in Ewing's sarcoma tumors and bone but not in cell lines according to embodiments of the present disclosure.

Referring to FIG. 21, focal adhesion genes and cancer genes expressed in Ewing's sarcoma tumors and bone but not in cell lines are illustrated. qRT-PCR data are shown for two Ewing's sarcoma cell lines (RD-ES and SK-N-MC), three Ewing sarcoma tumors (ESFT) and one osteosarcoma cell line unrelated to ESFT, as control of bone tumor cell line. Relative endogenous expression of each gene was normalized to actin (Average±SD, n=3).

Figure 22:
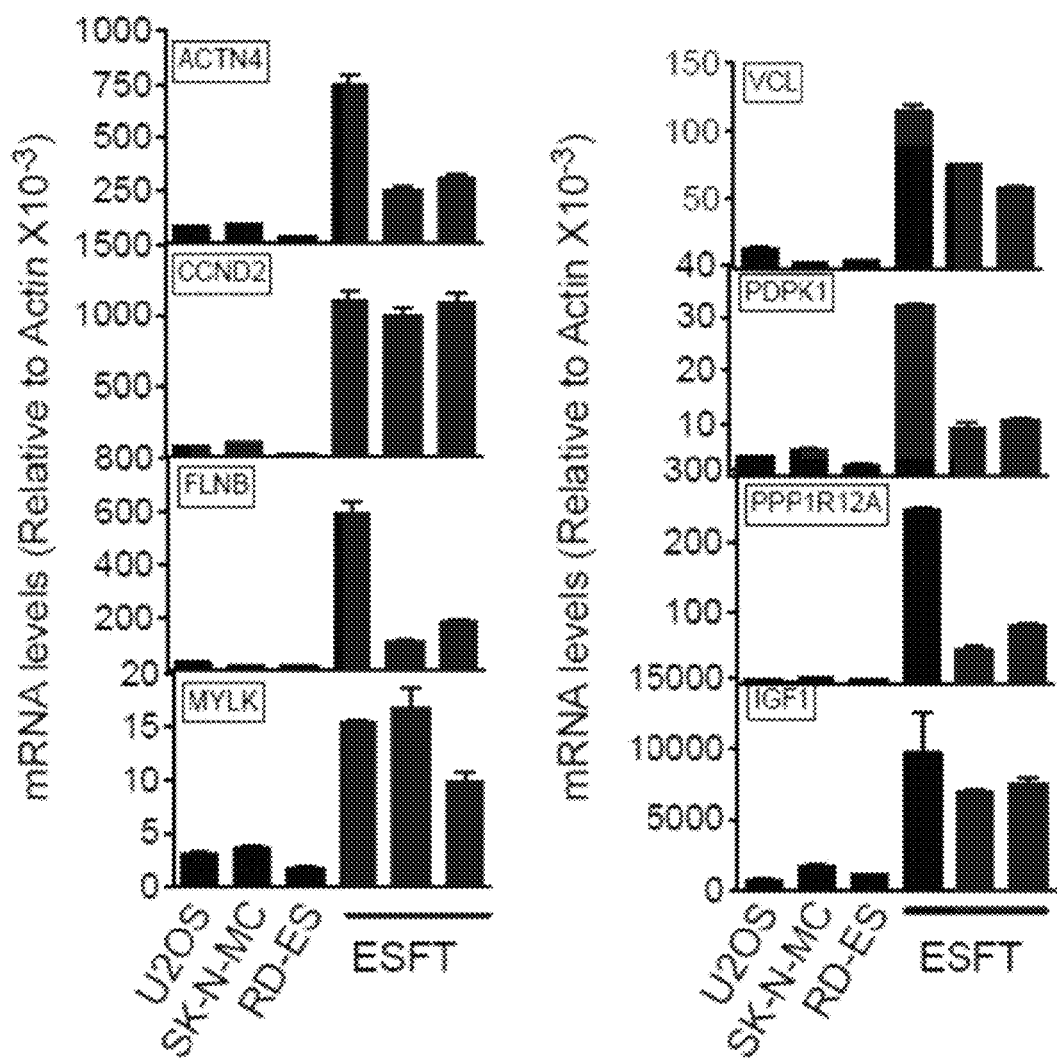
FIG. 22 illustrates focal adhesion genes differentially expressed in Ewing's sarcoma tumors and tumor cell lines according to embodiments of the present disclosure.

Referring to FIG. 22, focal adhesion genes differentially expressed in Ewing sarcoma tumors and cell lines are illustrated. qRT-PCR analysis of focal adhesion genes expressed in Ewing sarcoma tumors ESFT but not in cell lines. Data are shown for two Ewing's sarcoma cell lines (RD-ES and SK-N-MC), three Ewing sarcoma tumors (ESFT) and one osteosarcoma cell line as control of bone tumor cell line but unrelated to ESFT. Relative endogenous expression of each gene was normalized to actin (Average±SD, n=3).

Figure 23:
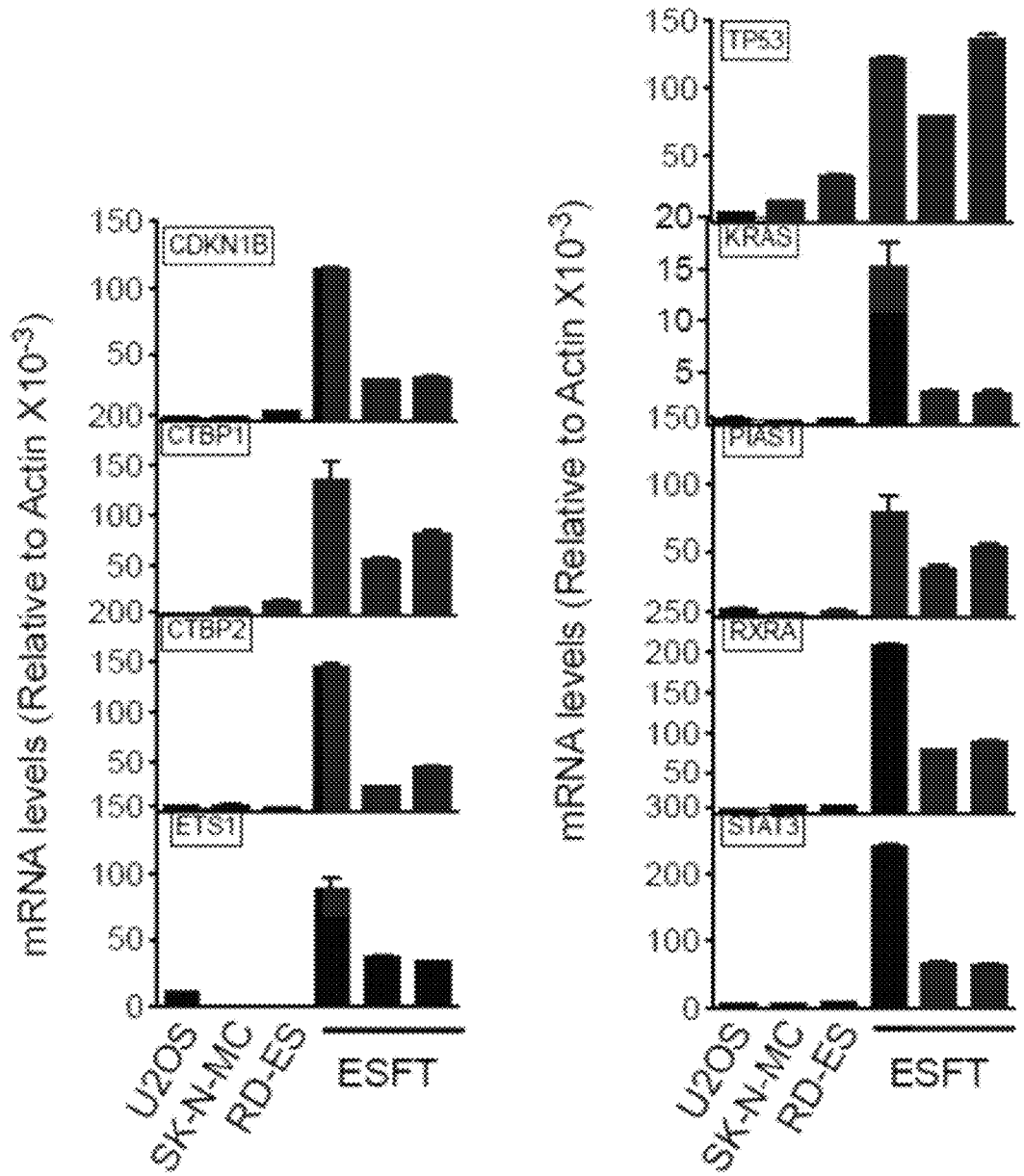
FIG. 23 illustrates cancer related genes differentially expressed in Ewing's sarcoma tumors and tumor cell lines according to embodiments of the present disclosure.

Referring to FIG. 23, cancer related genes differentially expressed in Ewing sarcoma tumors and cell lines are illustrated. qRT-PCR analysis of cancer related genes expressed in Ewing sarcoma tumors (ESFT) but not in cell lines. Data are shown for two Ewing's sarcoma cell lines (RD-ES and SK-N-MC), three tumors (ESFT) and one osteosarcoma cell line unrelated to ESFT as control of bone tumor cell line. Relative endogenous expression of each gene was normalized to actin (Average±SD, n=3).

Figure 24:
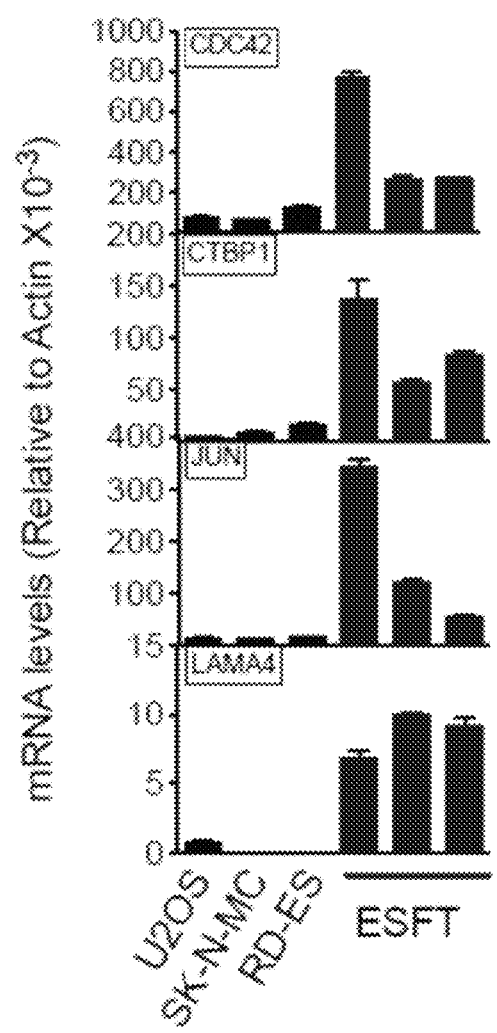
FIG. 24 illustrates focal adhesion and cancer genes differentially expressed in Ewing's sarcoma tumors and cell lines according to embodiments of the present disclosure.
Figure 24:
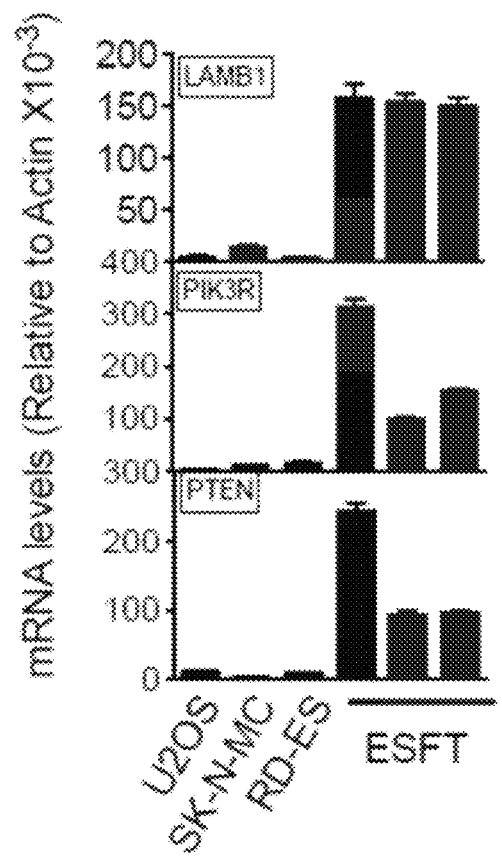

Referring to FIG. 24, focal adhesion and Cancer related genes differentially expressed in Ewing sarcoma tumors and cell lines are illustrated. qRT-PCR analysis of cancer related genes expressed in ESFT but not in cell lines. Data are shown for two Ewing's sarcoma cell lines (RD-ES and SK-N-MC), three tumors (ESFT) and one osteosarcoma cell line unrelated to ESFT as control of bone tumor cell line. Relative endogenous expression of each gene was normalized to actin (Average±SD, n=3).

Bioengineered Metastatic Tumors Using Mouse Models of Prostate Cancer

The predominant site of human prostate cancer metastasis is bone. Bone metastasis is the most frequent cause of death from prostate cancer. Genetically engineered mouse (GEM) models enable studies of metastasis in the native physiological milieu, and are suitable to model progression from tumorigenesis to metastasis. However, GEM models only rarely metastasize to bone, and fail to recapitulate the heterogeneity of human cancer phenotypes. In fact, a GEM model of fully penetrant metastatic prostate cancer displays metastases to many soft tissue sites but rarely if ever to bone. However, cells derived from this mouse model (i.e., NPK cells) readily form tumors when injected into the tibia.

The present disclosure combines generating mouse models of prostate cancer with tissue-engineering techniques, to evaluate prostate cancer metastasis in human bone context. The early metastasis tumor model can be evaluated by comparing to colonization of human or mouse prostate cancer cells injected through blood circulation into host mice that have been grafted with human or mouse bone. The advanced metastasis model can be evaluated by comparing to tumors formed by injecting human or mouse cancer cell aggregates directly into the grafted human or mouse bone. The host mice for these analyses can be non-obese diabetic/severe combined immunodeficient (NOD/SCID) mice engrafted with human bone.

Figure 25A:
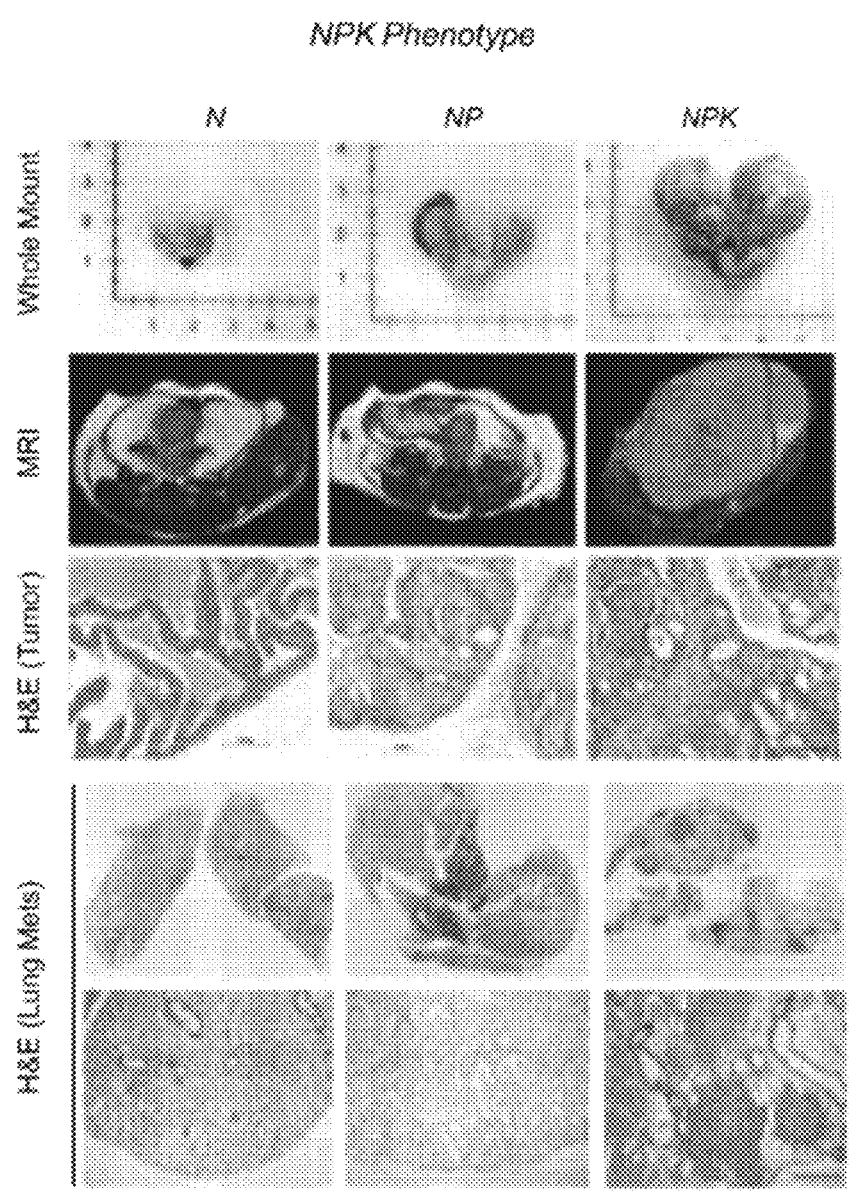
FIGS. 25A-C illustrates an NPK mouse model according to embodiments of the present disclosure.

A series of GEM models are provided that display a range of prostate cancer phenotypes and share conserved molecular pathways deregulated in human prostate cancer and particularly activation of PI3-kinase and MAP kinase signaling pathways. In particular, while NP (Nkx3.1 Cre-ERT2/+; Ptenflox/flox) tumors do not metastasize, NPK (Nkx3.1CreERT2/+; Ptenflox/flox; KrasLSL-G12D/+) tumors metastasize with nearly 100% penetrance to lymph nodes and soft tissues, most frequently to lungs and liver (FIGS. 25A-B), but not into the mouse bone. However, when implanted directly into the bone of host mice, the bone is rapidly colonized by the mouse tumor cells.

Figure 25B:
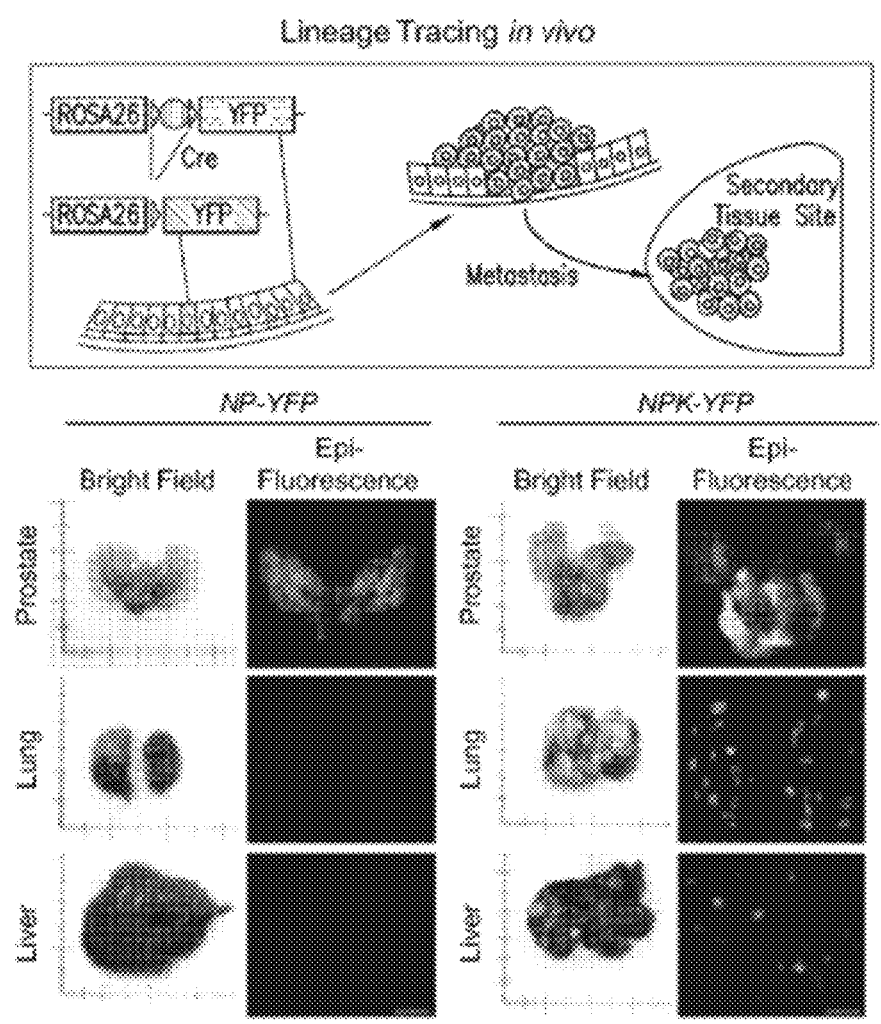
Figure 25C:
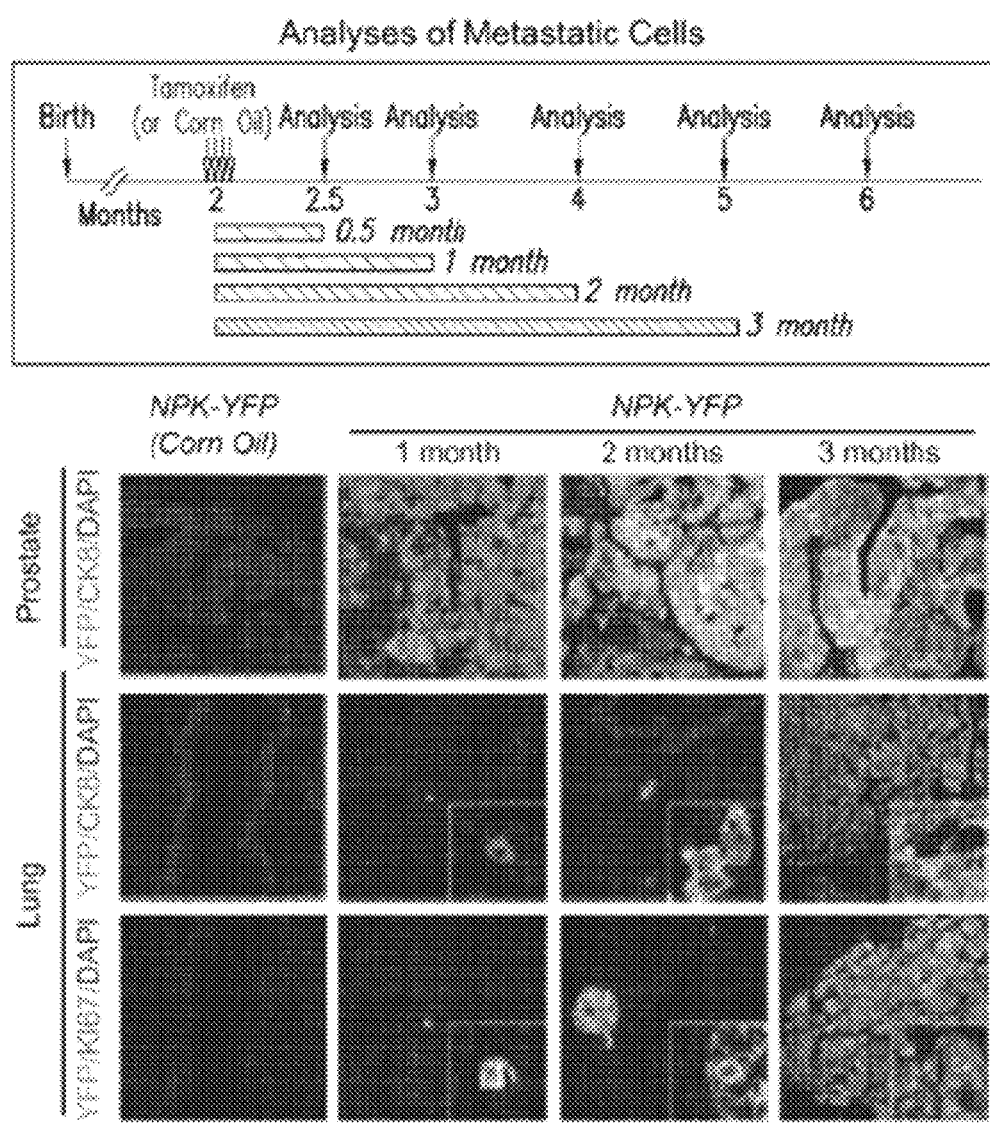

Lineage-tracing experiments using a Cre reporter allele R26R-YFP that indelibly marks prostate tumor cells, shows prominent YFP fluorescence in prostate tumors, lungs and livers from NPK mice that display metastases, but not in lungs or livers from NP mice that do not display metastases (FIG. 25B). Lineage-tracing is used to delineate the temporal and spatial relationship of tumors, disseminated cells, and metastases in the NPK mice, to observe a clear temporal delay in the appearance of metastasis which appear at 2-3 months relative to primary tumors which appear after only 1 month.

Metastasis Assay for Prostate Cancer Using the Bone-Engineered System

By using both human (PC3—highly metastatic and 22Rv1—non-metastatic) and mouse (NP-non metastatic, NPK-highly metastatic) prostate cancer cells, prostate cancer metastasis can be studied in a tissue- and species-specific manner, to determine whether the mouse bone provides the permissive microenvironment for prostate cancer metastasis as does human bone. These studies can be performed with both human and mouse prostate cancer cells. It is distinguishable whether preferential homing of human prostate cancer to bone (which cannot be readily recapitulated in mouse models) reflects a property of the primary tumor cells (human versus mouse) or whether tumor cells have a selective preference for human bone regardless of whether they are derived from mice or man.

To follow the cells in vivo the human PC3 and 22Rv1 cells are transduced with retroviral particles to stably express a dual luciferase-RFP reporter using a pMXs-IRES-Luc-RFP retroviral vector (Abate-Shen lab). Mouse NP and NPK cells are derived from mice already carrying a lineage tracing allele based on the expression of the YFP protein under the control of the R26r promoter. These cells are transduced to stably express a luciferase reporter by removing the RFP cassette. First, human pre-vascularized engineered bone (4×4 mm discs) is generated by sequential culture of hMSCs and HUVECs in bone scaffolds. After 4 weeks, engineered bone is implanted subcutaneously in male NOG/SCID mice for 10 days, a period that is sufficient to allow bone vascularization. Ten days post-implantation, $2.5 \times 10^5$ PC3 or NPK cells are injected into the tail vein with the luciferase-marked human or mouse prostate cancer cells, as above, and the mice are monitored twice a week for tumor formation in distant organs including the bone, using a Xenogen IVIS imaging system 15 minutes after intraperitoneal injection of 1.5 mg D-Luciferin. This model is compared to an early metastasis model. In separate animals, not implanted with human bone, human PC3 and mouse NPK cells transduced with luciferase reporter will be injected ($10^5$ cells per mouse) directly into the mouse tibia, to be compared with the advanced metastasis model. Second, $10^5$ cells are implanted orthotopically into the mouse prostate and monitored over a period of 3 months for dissemination to distant organs, and into the implanted engineered bones (human and mouse). This assay provides the most stringent conditions for recapitulating almost entirely the initial steps of local invasion and extravasation.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A tissue engineered three-dimensional model, comprising:
a three-dimensional bone scaffold seeded with Ewing's sarcoma (ES) tumor cells and cultured osteoblasts, wherein the tissue engineered three-dimensional model exhibits re-expression of at least one of focal adhesion genes, cancer-related genes or both.

2. The three-dimensional model of claim 1, wherein the osteoblasts are produced by a cell differentiation process from mesenchymal stem cells.

3. The three-dimensional model of claim 2, wherein the cell line is SK-N-MC cell line.

4. The three-dimensional model of claim 2, wherein the cell line is RD-ES cell line.

5. The three-dimensional model of claim 1, wherein the Ewing's sarcoma tumor cells are spheroids.

6. The three-dimensional model of claim 1, wherein the three-dimensional model further comprises collagen 1 (col 1) and hyaluronic acid (HA) proteins.

7. The three-dimensional model of claim 1, wherein the three-dimensional bone scaffold comprises a decellularized bone matrix scaffold comprising a plurality of perfusion channels.

8. The three-dimensional model of claim 7, wherein the three-dimensional bone scaffold has an outer region, an inner region, and a central core region.

9. The three-dimensional model of claim 8, wherein the central core region includes Ewing's sarcoma spheroids in a necrotic micro-region, and the inner region includes Ewing's sarcoma spheroids in a hypoxic micro-region.

10. The three-dimensional model of claim 9, wherein the outer region is neither hypoxic nor necrotic.

11. The three-dimensional model of claim 7, further comprising
an oxygen supply in gaseous communication with the bone scaffold; and
a vasculature in fluid communication with the bone scaffold.

12. The three-dimensional model of claim 7 further comprising a mechanical load coupled to the bone scaffold.

13. The three-dimensional model of claim 7, wherein Ewing's sarcoma cells are aggregated in a plurality of tumor spheroids.

14. The three-dimensional model of claim 1, wherein the model recapitulates the osteolytic process observed in bones of a human and is predictive of native tumors in vitro.

15. The three-dimensional model of claim 1, wherein focal adhesion genes are expressed in Ewing sarcoma tumors.

16. The three-dimensional model of claim 1, wherein the re-expressed focal adhesion genes include at least one of: ACTN4, CCND2, COL1A2, COL3A1, COL6A1, COL6A2, COL6A3, FLNB, MYLK, PDPK1, PPP1R12A, IGF1, VCL.

17. The three-dimensional model of claim 1, wherein the re-expressed cancer include at least one of: CDKN1B, CTBP1, CTBP2, ETS1, KRAS, PIAS1, RXRA, STAT3, TP53.

18. The three-dimensional model of claim 1, wherein the tissue engineered three-dimensional model exhibits re-expression of angiogenesis and vasculogenic mimicry features favoring tumor adaptation.

19. The three-dimensional model of claim 1, wherein the Ewing's sarcoma cells are patient derived cells.

20. The three-dimensional model of claim 1, wherein the scaffold is fully decellularized bone prior to seeding with Ewing's sarcoma cells.

* * * * *

UNITED STATES PATENT AND TRADEMARK OFFICE
CERTIFICATE OF CORRECTION

PATENT NO. : 10,883,083 B2
APPLICATION NO. : 16/016101
DATED : January 5, 2021
INVENTOR(S) : Gordana Vunjak-Novakovic and Aranzazu Villasante It is certified that error appears in the above-identified patent and that said Letters Patent is hereby corrected as shown below:

In the Specification

Column 1, Lines 23-25, please replace:
"This invention was made with government support under grants EB002520 and EB17103 awarded by the NIH. The government has certain rights in the invention."

With:
--This invention was made with government support under CA183684, EB017103, and EB002520 awarded by the National Institutes of Health. The government has certain rights in the invention.--

Signed and Sealed this
Ninth Day of July, 2024

Katherine Kelly Vidal
*Director of the United States Patent and Trademark Office*